US012243646B1

United States Patent
Paul, Jr. et al.

(10) Patent No.: US 12,243,646 B1
(45) Date of Patent: Mar. 4, 2025

(54) SYSTEMS AND METHODS FOR IMPROVING RETRIEVAL-AUGMENTED GENERATION IN CLINICAL DECISION SUPPORT

(71) Applicant: Glass Health Inc., San Francisco, CA (US)

(72) Inventors: Dereck William Paul, Jr., Tiburon, CA (US); Graham Ramsey, San Francisco, CA (US)

(73) Assignee: Glass Health Inc., San Francisco, CA (US)

( * ) Notice: Subject to any disclaimer, the term of this patent is extended or adjusted under 35 U.S.C. 154(b) by 0 days.

(21) Appl. No.: 18/659,846

(22) Filed: May 9, 2024

Related U.S. Application Data

(60) Provisional application No. 63/554,881, filed on Feb. 16, 2024.

(51) Int. Cl.
| | |
|---|---|
| *G06N 20/00* | (2019.01) |
| *G10L 15/26* | (2006.01) |
| *G16H 15/00* | (2018.01) |
| *G16H 20/00* | (2018.01) |
| *G16H 50/20* | (2018.01) |

(52) U.S. Cl.
CPC ............ *G16H 50/20* (2018.01); *G10L 15/26* (2013.01); *G16H 15/00* (2018.01); *G16H 20/00* (2018.01)

(58) Field of Classification Search
CPC ........ G16H 50/20; G16H 15/00; G16H 20/00; G10L 15/26
See application file for complete search history.

(56) References Cited

U.S. PATENT DOCUMENTS

| | | | |
|---|---|---|---|
| 2014/0288964 A1* | 9/2014 | Zillner | G16H 50/20 |
| | | | 705/3 |
| 2021/0343411 A1* | 11/2021 | Zhang | G06N 5/045 |
| 2024/0145057 A1* | 5/2024 | Afrasiabi | G06N 20/00 |

OTHER PUBLICATIONS

ACR Appropriateness Criteria®. Retrieved from Internet URL: https://www.acr.org/Clinical-Resources/ACR-Appropriateness-Criteria. pp. 1-4. [retrieved on Oct. 16, 2023]. Retrieved from the Internet on May 19, 2024.
AI-Powered Clinical Decision Support. [Website] Glass Health. Retrieved from Internet URL: https://glass.health/. pp. 1-6. [retrieved on Oct. 16, 2023]. Retrieved from the Internet on May 19, 2024.
Chen, Lingjiao et al. How is ChatGPT's behavior changing over time?. arXiv: pp. 1-26 (2023) Retrieved from Internet on May 19, 2024 URL: https://doi.org/10.48550/arXiv.2307.09009.
Dale, Robert. GPT-3: What's it Good For?. Natural Language Engineering vol. 27,1: pp. 113-118 (2021).

(Continued)

*Primary Examiner* — Maroun P Kanaan
(74) *Attorney, Agent, or Firm* — WILSON SONSINI GOODRICH & ROSATI

(57) ABSTRACT

Described are systems and methods for artificial intelligence (AI)-based clinical decision support. Systems can include a platform configured with a user input processing module, a context matching module, a retrieval-augmented generation (RAG) module, and an output generation module. Outputs of the platform can include a differential diagnosis, an assessment and treatment plan, or a clinical reference. The platform can further include an AI-copilot module and an AI-notebook module.

21 Claims, 34 Drawing Sheets

(56) References Cited

OTHER PUBLICATIONS

GPT-4. Published online Mar. 14, 2023. Retrieved from Internet URL: https://openai.com/index/gpt-4-research/. pp. 1-19. [retrieved on Oct. 16, 2023]. Retrieved from the Internet on May 19, 2024.
Hosny, Ahmed et al. Artificial Intelligence In Radiology. Nature Reviews Cancer vol. 18,8: pp. 500-510 (2018).
Hunter, John D et al. Matplotlib: A 2D Graphics Environment. Computing in Science & Engineering vol. 9,3: pp. 90-95 (2007).
Kjelle, Elin et al. Characterizing And Quantifying Low-value Diagnostic Imaging Internationally: A Scoping Review. BMC Medical Imaging vol. 22,1: 73, pp. 1-28 (2022).
Nazario-Johnson, Lleayem et al. Use of Large Language Models to Predict Neuroimaging. Journal of the American College of Radiology vol. 20,10: pp. 1004-1009 (2023).
Pedersen, Mangor et al. Artificial Intelligence For Clinical Decision Support In Neurology. Brain Communications vol. 2,2: pp. 1-11 (2020).
Ramgopal, Sriram et al. Artificial Intelligence-Based Clinical Decision Support In Pediatrics. Pediatric Research vol. 93,2: pp. 334-341 (2023). Published online Jul. 29, 2022.
Rao, Arya et al. Evaluating GPT as an Adjunct for Radiologic Decision Making: GPT-4 Versus GPT-3.5 in a Breast Imaging Pilot. Journal of the American College of Radiology vol. 20,10: pp. 990-997 (2023).
Saporta, Adriel et al. Benchmarking Saliency Methods For Chest X-ray Interpretation. Nature Machine Intelligence vol. 4: pp. 867-878 (2022).
Sun, Chi et al. How to Fine-Tune BERT for Text Classification? ArXiv, 2019, /abs/1905.05583. Published on Feb. 5, 2020. Retrieved from the Internet URL:https://arxiv.org/abs/1905.05583 Retrieved on May 20, 2024.
Varney, Elliot T et al. The Potential for Using ChatGPT to Improve Imaging Appropriateness. Journal of the American College of Radiology vol. 20,10: pp. 988-989 (2023).
Vaswani, Ashish et al. Attention is All you Need. Advances in Neural Information Processing Systems, Proceedings of the 31st International Conference on Neural Information Processing Systems vol. 30: pp. 1-11 (2017).
Virtanen, Pauli et al. SciPy 1.0: Fundamental Algorithms For Scientific Computing In Python. Nature Methods vol. 17,3: pp. 261-272 (2020).
White, Jules et al. A Prompt Pattern Catalog to Enhance Prompt Engineering with ChatGPT. arXiv: pp. 1-19 (2023) Retrieved from Internet URL: https://doi.org/10.48550/arXiv.2302.11382.
Young, Albert T et al. AI in Dermatology. AI in Clinical Medicine: A Practical Guide for Healthcare Professionals, First Edition, John Wiley & Sons, Ltd: pp. 165-175 (2023).
Zaki, Hossam A et al. The Application of (LLMs) Large Language Models for Radiologic Decision Making. Journal of the American College of Radiology vol. S1546-1440,24: pp. 1-21 (2024).
Zhang, Jie et al. Ethics And Governance Of Trustworthy Medical Artificial Intelligence. BMC Medical Informatics and Decision Making vol. 23,1: 7, pp. 1-15 (2023).

* cited by examiner

Patient | Published Context [SWITCH]

Analyze a Patient Summary

Include age, sex, relevant past medical history, medications, presenting symptoms, associated symptoms, descriptions of relevant studies (including labs and imaging), the illness course and any additional information you might include when counseling another physician about your patient 65 year old woman with a history of diabetes and hyperlipidemia presents with acute-onset chest pain and diaphoresis found to have hyperacute T-waves without ST elevation.

Draft differentials and plans provide information that a clinician may consider but should never replace a clinician's judgment.

Protected Identifying information should not be entered into the Platform. All patient summaries should be de-identified.

[Draft Differential Diagnosis] [Draft Clinical Plan]

*Try an example:*

● Chest pain with hyperacute T waves ● Subacute progressive dyspnea ● Generate a DDx first to create a more accurate Clinical Plan.

SYSTEMS AND METHODS FOR IMPROVING RETRIEVAL-AUGMENTED GENERATION IN CLINICAL DECISION SUPPORT

CROSS-REFERENCE TO RELATED APPLICATIONS

This application claims priority to U.S. Provisional Application No. 63/554,881, filed Feb. 16, 2024, which is incorporated by reference herein in its entirety.

BACKGROUND

Artificial Intelligence (AI) has made significant strides to improve healthcare outcomes in areas such as neurology, pediatrics, dermatology, and radiology. At the forefront of advances in AI are large language models (LLMs), which can be configured to comprehend and generate human-like text, speech, or audio. Accurately recommending appropriate modalities for treatment can be important for improving healthcare outcomes, preventing unnecessary procedures, and limiting wasteful use of healthcare dollars. However, some LLMs can be deficient at least because they may use historic or old data for training the LLMs or they may be trained using general data that is not specific to a context, e.g., the context of healthcare or medicine. Accordingly, such LLMs may make recommendations that are inaccurate and result in poor healthcare outcomes.

SUMMARY

Recognized herein is a need for large language models (LLMs) that are trained using current and specific data (e.g., context specific) and can process or augment the data using retrieval-augmented generation (RAG). Data may be associated with panels, topics, and variants in the context of healthcare or medicine. Panels can include the specific areas of healthcare, e.g., radiology for a patient seeking breast care. Topics can include specific diseases that fall under each panel, e.g., a patient with breast cancer. Variants can include presentations within each topic, e.g., age of the patient with breast cancer.

In an aspect, disclosed herein is an artificial intelligence (AI)-based clinical decision support platform, the platform comprising: a user input processing module configured to receive a clinical problem representation (CPR) based at least in part on an input provided by a user, a context matching module configured to (1) process a prompt for refining the CPR and identify a suitable context, (2) provide the CPR along with one or more relevant context topics to a first large language model (LLM), and (3) use the first LLM to generate a first output comprising a preliminary clinical diagnosis and a context match relating to the CPR; a retrieval-augmented generation (RAG) module configured to process the context match and the one or more relevant context topics from the context matching module using a physician-validated context library, to determine a context topic based on physician-validated schemas or clinical guidelines for pushing into a second LLM; and an output generation module configured to use the second LLM to process (1) the CPR, (2) the context based on the physician-validated schemas or clinical guidelines, and (3) one or more targeted prompts, to generate a second output comprising at least one of a differential diagnosis, an assessment of a health condition, or a treatment plan for the health condition. In some embodiments, the user input processing module is further configured to generate the CPR. In some embodiments, the one or more targeted prompts comprises a prompt for generating the differential diagnosis, and wherein the second output comprises the differential diagnosis. In some embodiments, the one or more targeted prompts comprises a prompt for generating the assessment and the treatment plan for the health condition, and wherein the second output comprises the assessment and the treatment plan for the health condition. In some embodiments, the one or more targeted prompts comprises a prompt for generating the answer to the CRQ, and wherein the second output comprises the answer to the CRQ. In some embodiments, the RAG module is further configured to provide or refine the one or more relevant context topics iteratively back to the context matching module for subsequent pushing into the first LLM. In some embodiments, the platform further comprising an AI-copilot module configured to generate data for a pre-visit clinical decision, and wherein the data is received by the user input processing module to further assist the platform in generating the differential diagnosis, the assessment of a health condition, or the treatment plan for the health condition. In some embodiments, the platform further comprising an AI-notebook module configured to generate data associated with clinical knowledge, and wherein the data is received by the user input processing module to further assist the platform in generating the differential diagnosis, the assessment of a health condition, or the treatment plan for the health condition. In some embodiments, the first LLM is different than the second LLM, and wherein the first LLM has been trained using a set of data that is older than a set of data used to train the second LLM. In some embodiments, the first LLM has been further trained based at least on the one or more relevant context topics to generate the second LLM. In some embodiments, the RAG module is further configured to use embedding-based matching to determine a relevance of the input provided by the user. In some embodiments, the RAG module is further configured to use one or more prompts to improve processing of the context match and the one or more relevant context topics. In some embodiments, the one or more prompts comprises chain-of-thought prompt engineering. In some embodiments, the RAG module is further configured to use N-shot learning to improve processing of the context match and the one or more relevant context topics. In some embodiments, the N-shot learning comprises at least one learning example. In some embodiments, the input provided by the user comprises a text input, a speech input, a video input, or any combination thereof. In some embodiments, the platform is configured to (i) transform the speech input or the video input into a text input and (ii) transmit the text input to the user input processing module. In some embodiments, a number of iterations is based at least on a confidence level of the differential diagnosis, the assessment of the health condition, or the treatment plan for the health condition. In some embodiments, the confidence level is at least 80%. In some embodiments, the platform further comprises a graphical user interface (GUI) configured to display one or more healthcare reports to the user or a healthcare provider based at least on the differential diagnosis, the assessment of the health condition, or the treatment plan for the health condition.

In another aspect, disclosed herein is an artificial intelligence (AI)-based clinical decision support platform, the platform comprising: a user input processing module configured to receive at least a clinical reference question (CRQ) based at least in part on an input provided by a user, a context matching module configured to (1) process a prompt for refining and understanding at least the CRQ and identify a suitable context, (2) provide at least the CRQ along with one or more relevant context topics to a first large language model (LLM), and (3) use the first LLM to generate a first output comprising a preliminary clinical diagnosis and a context match relating to a clinical problem representation (CPR); a retrieval-augmented generation (RAG) module configured to process the context match and the one or more relevant context topics from the context matching module using a physician-validated context library, to determine a context topic based on physician-validated clinical guidelines for pushing into a second LLM; and an output generation module configured to use the second LLM to process (1) the CPR. (2) the context based on the physician-validated clinical guidelines, and (3) one or more targeted prompts for answering the CRQ, to generate a second output comprising of an answer to the CRQ, wherein the answer is provided to the user through a chatbot interface. In some embodiments, the user input processing module is further configured to generate the CPR. In some embodiments, the context matching module is further configured to process another prompt for refining the CPR. In some embodiments, the context matching module is further configured to provide the CRQ and the CPR to the first LLM. In some embodiments, the RAG module is further configured to provide or refine the one or more relevant context topics iteratively back to the context matching module for subsequent pushing into the first LLM. In some embodiments, the platform further comprising an AI-copilot module configured to generate data for a pre-visit clinical decision, and wherein the data is received by the user input processing module to further assist the platform in generating the answer to the CRQ. In some embodiments, the platform further comprising an AI-notebook module configured to generate data associated with clinical knowledge, and wherein the data is received by the user input processing module to further assist the platform in generating the answer to the CRQ. In some embodiments, the first LLM is different than the second LLM, and wherein the first LLM has been trained using a set of data that is older than a set of data used to train the second LLM. In some embodiments, the first LLM has been further trained based at least on the one or more relevant context topics to generate the second LLM. In some embodiments, the RAG module is further configured to use embedding-based matching to determine a relevance of the input provided by the user. In some embodiments, the RAG module is further configured to use one or more prompts to improve processing of the context match and the one or more relevant context topics, and wherein the one or more prompts comprises chain-of-thought prompt engineering. In some embodiments, the RAG module is further configured to use N-shot learning to improve processing of the context match and the one or more relevant context topics, and w % herein the N-shot learning comprises at least one learning example.

In another aspect, disclosed herein is a computer program product for an artificial intelligence (AI)-based clinical decision support platform, the computer program product comprising at least one non-transitory computer-readable medium having computer-readable program code portions embodied therein, the computer-readable program code portions comprising: an executable user input processing portion configured to receive a clinical problem representation (CPR) based at least in part on an input provided by a user; an executable context matching portion configured to (1) process a prompt for refining the CPR and identify a suitable context, (2) provide the CPR along with one or more relevant context topics to a first large language model (LLM), and (3) use the first LLM to generate a first output comprising a preliminary clinical diagnosis and a context match relating to the CPR; an executable retrieval-augmented generation (RAG) portion configured to process the context match and the one or more relevant context topics using a physician-validated context library to determine a context topic based on physician-validated schemas or clinical guidelines for pushing into a second LLM; and an executable output generation portion configured to use the second LLM to process (1) the CPR, (2) the context based on the physician-validated schemas or clinical guidelines, and (3) one or more targeted prompts, to generate a second output comprising at least one of a differential diagnosis, an assessment of a health condition, or a treatment plan for the health condition.

In another aspect, disclosed herein is a computer program product for an artificial intelligence (AI)-based clinical decision support platform, the computer program product comprising at least one non-transitory computer-readable medium having computer-readable program code portions embodied therein, the computer-readable program code portions comprising: an executable user input processing portion configured to receive at least a clinical reference question (CRQ) based at least in part on an input provided by a user; an executable context matching portion configured to (1) process a prompt for refining and understanding at least the CRQ and identify a suitable context, (2) provide at least the CRQ along with one or more relevant context topics to a first large language model (LLM), and (3) use the first LLM to generate a first output comprising a preliminary clinical diagnosis and a context match relating to a clinical problem representation (CPR); an executable retrieval-augmented generation (RAG) portion configured to process the context match and the one or more relevant context topics using a physician-validated context library to determine a context topic based on physician-validated clinical guidelines for pushing into a second LLM; and an executable output generation portion configured to use the second LLM to process (1) the CPR, (2) the context based on the physician-validated clinical guidelines, and (3) one or more targeted prompts for answering the CRQ, to generate a second output comprising of an answer to the CRQ, wherein the answer is provided to the user through a chatbot interface.

In another aspect, disclosed herein is a system comprising at least one processor and instructions executable by the at least one processor to cause the at least one processor to perform operations comprising: (a) receiving a clinical problem representation (CPR) based at least in part on an input provided by a user; (b) using the input to (1) process a prompt for refining the CPR and identify a suitable context, (2) provide the CPR along with one or more relevant context topics to a first large language model (LLM), and (3) use the first LLM to generate a first output comprising a preliminary clinical diagnosis and a context match relating to the CPR; (c) processing the context match and the one or more relevant context using a physician-validated context library to determine a context topic based on physician-validated schemas or clinical guidelines for pushing into a second LLM; and (d) using the second LLM to process (1) the CPR, (2) the context based on the physician-validated schemas or clinical guidelines, and (3) one or more targeted prompts, to generate a second output comprising at least one of a differential diagnosis, an assessment of a health condition, or a treatment plan for the health condition.

In another aspect, disclosed herein is a computer-implemented method of providing artificial intelligence (AI)-based clinical decision support, the method comprising: (a) receiving a clinical problem representation (CPR) based at least in part on an input provided by a user; (b) using the input to (1) process a prompt for refining the CPR and identify a suitable context, (2) provide the CPR along with one or more relevant context topics to a first large language model (LLM), and (3) use the first LLM to generate a first output comprising a preliminary clinical diagnosis and a context match relating to the CPR; (c) processing the context match and the one or more relevant context using a physician-validated context library to determine a context topic based on physician-validated schemas or clinical guidelines for pushing into a second LLM; and (d) using the second LLM to process (1) the CPR, (2) the context based on the physician-validated schemas or clinical guidelines, and (3) one or more targeted prompts, to generate a second output comprising at least one of a differential diagnosis, an assessment of a health condition, or a treatment plan for the health condition.

In another aspect, disclosed herein is a system comprising at least one processor and instructions executable by the at least one processor to cause the at least one processor to perform operations comprising: (a) receiving at least a clinical reference question (CRQ) based at least in part on an input provided by a user; (b) using the input to (1) process a prompt for refining and understanding at least the CRQ and identify a suitable context, (2) provide at least the CRQ along with one or more relevant context topics to a first large language model (LLM), and (3) use the first LLM to generate a first output comprising a preliminary clinical diagnosis and a context match relating to a clinical problem representation (CPR); (c) processing the context match and the one or more relevant context topics using a physician-validated context library, to determine a context topic based on physician-validated clinical guidelines for pushing into a second LLM; and (d) using the second LLM to process (1) the CPR, (2) the context based on the physician-validated clinical guidelines, and (3) one or more targeted prompts for answering the CRQ, to generate a second output comprising of an answer to the CRQ, wherein the answer is provided to the user through a chatbot interface.

In another aspect, disclosed herein is a computer-implemented method of providing artificial intelligence (AI)-based clinical decision support, the method comprising: (a) receiving at least a clinical reference question (CRQ) based at least in part on an input provided by a user; (b) using the input to (1) process a prompt for refining and understanding at least the CRQ and identify a suitable context, (2) provide at least the CRQ along with one or more relevant context topics to a first large language model (LLM), and (3) use the first LLM to generate a first output comprising a preliminary clinical diagnosis and a context match relating to a clinical problem representation (CPR); (c) processing the context match and the one or more relevant context topics using a physician-validated context library, to determine a context topic based on physician-validated clinical guidelines for pushing into a second LLM; and (d) using the second LLM to process (1) the CPR, (2) the context based on the physician-validated clinical guidelines, and (3) one or more targeted prompts for answering the CRQ, to generate a second output comprising of an answer to the CRQ, wherein the answer is provided to the user through a chatbot interface.

Additional aspects and advantages of the present disclosure will become readily apparent from the following detailed description, wherein only illustrative embodiments of the present disclosure are shown and described. As will be realized, the present disclosure is capable of other and different embodiments, and its several details are capable of modifications in various obvious respects, all without departing from the present disclosure. Accordingly, the drawings and description are to be regarded as illustrative in nature and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the present disclosure contained in the specification, the specification is intended to supersede and/or take precedence over any such contradictory material.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 1A illustrates an example high-level system architecture for performing methods herein; FIG. 1B illustrates an example detailed system architecture for performing methods herein, which can include a differential diagnosis generator (DDx) module, an assessment and plan (A&P) module, and a consult module.

FIG. 8A illustrates improvements in pediatric panels depicting an R-value (or "r" as depicted) of 0.75; FIG. 8B illustrates improvements in neurologic panels depicting an R-value (or "r" as depicted) of 0.71; FIG. 8C illustrates improvements in vascular panels depicting an R-value (or "r" as depicted) of 0.12. FIG. 8D illustrates improvements in musculoskeletal (MSK) panels depicting an R-value (or "r" as depicted) of 0.59; FIG. 8E illustrates improvements in chest health panels depicting an R-value (or "r" as depicted) of 0.63 or 0.54 for cardiac or thoracic, respectively; FIG. 8F illustrates improvements in women's health panels depicting an R-value (or "r" as depicted) of 0.23 or 0.54 for breast or obstetrician-gynecologist (OBGYN), respectively; FIG. 8G illustrates improvements in breast panels and neurologic panels depicting an R-value (or "r" as depicted) of 0.23 or 0.71, respectively; FIG. 8H illustrates improvements in body health panels depicting an R-value (or "r" as depicted) of 0.42 or 0.32 for gastroenterology (GI) or urologic, respectively.

FIGS. 9A-9B illustrate examples of user interfaces associated with systems and methods herein, in accordance with some embodiments. FIG. 9A illustrates providing inputs (e.g., a clinical problem representation (CPR) or clinical reference question (CRQ)) to a user interface to generate a differential diagnosis (DDx) by the DDx module, an assessment and plan by the A&P module, or a consult (e.g., clinical reference) by the consult module; FIG. 9B illustrates a user interface associated with the systems and methods herein for displaying inputs and outputs associated with the CPR, the CQR, a differential diagnosis (DDx) by the DDx module, an assessment and plan (A&P) by the A&P module, a consult (e.g., clinical reference) by the consult module, the AI-copilot module, or the AI-notebook module.

FIG. 10A illustrates an example flow for receiving or generating inputs associated with generating a DDx; FIG. 10B illustrates an example flow for extracting meaning associated with generating a DDx; FIG. 10C illustrates an example flow for using retrieval-augmented generation (RAG) and context matching associated with generating a DDx; FIG. 10D illustrates an example flow for generating outputs associated with generating a DDx.

FIG. 11A illustrates an example flow for receiving or generating inputs associated with generating an A&P; FIG. 11B illustrates an example flow for extracting meaning associated with generating an A&P; FIG. 11C illustrates an example flow for using retrieval-augmented generation (RAG) and context matching associated with generating an A&P; FIG. 11D illustrates an example flow for generating outputs associated with generating an A&P.

FIG. 12A illustrates an example flow for receiving or generating inputs associated with generating a consult or clinical reference; FIG. 12B illustrates an example flow for extracting meaning associated with generating a consult or clinical reference; FIG. 12C illustrates an example flow for using retrieval-augmented generation (RAG) and context matching associated with generating a consult or clinical reference; FIG. 12D illustrates an example flow for generating outputs associated with generating a consult or clinical reference.

DETAILED DESCRIPTION

Figure 1A:
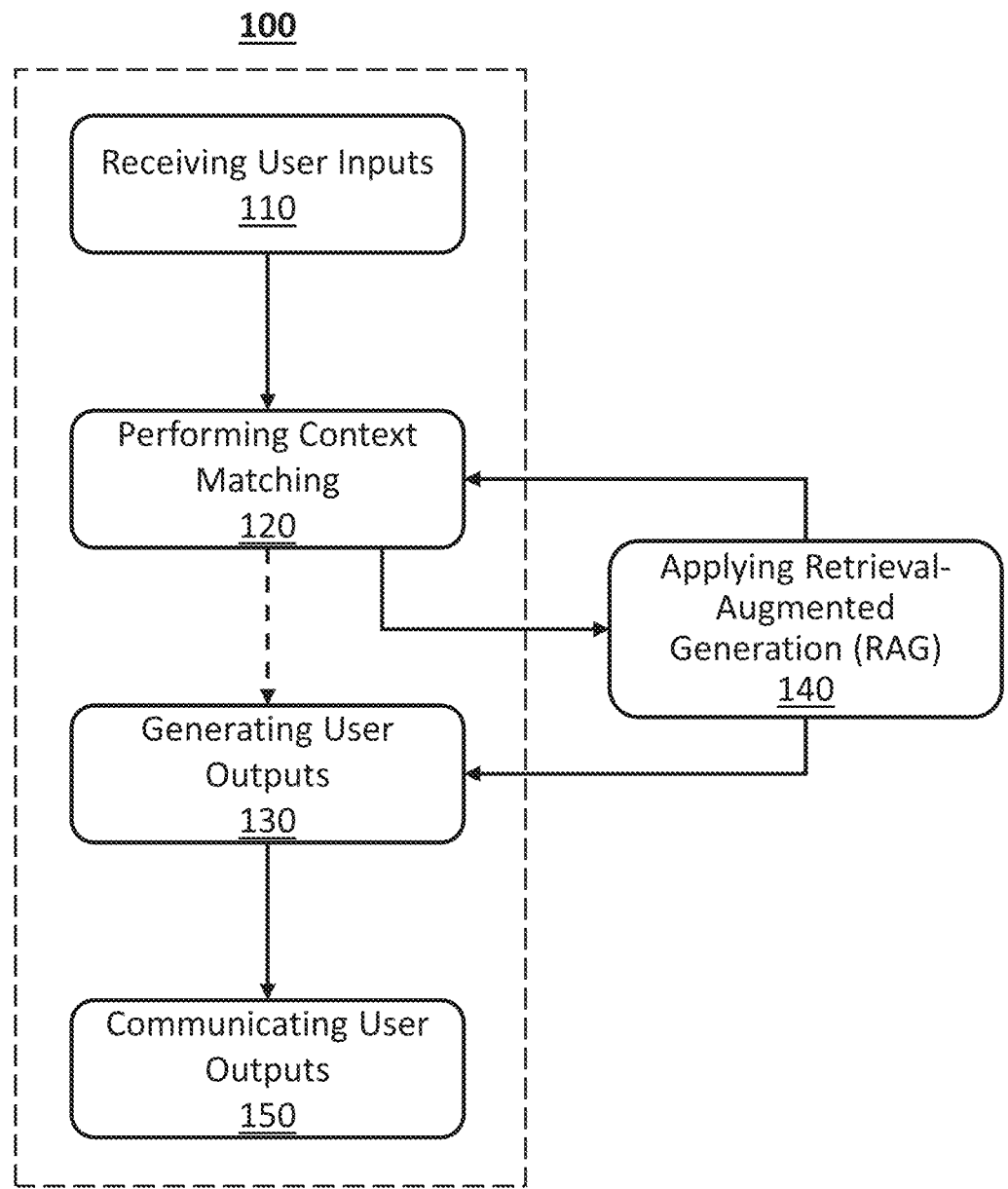
FIGS. 1A-1B illustrate example platform or system architectures for performing methods herein, in accordance with some embodiments.

While various embodiments of the present disclosure have been shown and described herein, such embodiments are provided by way of example only. Numerous variations, changes, or substitutions may occur without departing from the present disclosure. It should be understood that various alternatives to the embodiments of the present disclosure described herein may be employed.

Overview

Typical approaches for using artificial intelligence (AI), including generative AI such as large language models (LLM), in the context of healthcare or medicine can be deficient for improving healthcare outcomes for patients. For example, some approaches may use historic or old data for training the LLMs. Also, some approaches may use generalized data for training the LLMs that is not specific to the context of healthcare or medicine. Accordingly, such LLMs may make recommendations that are inaccurate and result in poor healthcare outcomes.

Further, traditional vector matching may not work for matching to context for the purpose of using that context to develop a differential diagnosis (DDx) or an assessment and plan (A&P). Some diseases may be represented or presented in text very similarly but can have very different pathophysiologies. For example, type-1 Diabetes Mellitus can be very different than type-2 Diabetes Mellitus from a pathophysiology, diagnosis, and medical treatment context. However, they can be similar when transforming the associated data into vectors for embedding match. Thus, this can make matching an AI input to the right context a challenging technical problem and can create a high risk for inappropriate matching to the wrong context. In turn, this can result in incorrect application of the context, which can degrade AI outputs and lead to AI outputs that contain inaccurate outputs.

Also, similar technical problems can arise when representing a patient summary as a vector for embedding. For example, a patient with a history of myocardial infarction who presents with subacute chest pain may be having another heart attack, may be presenting with new onset of heart failure, or may have a pulmonary embolism. The presentations for all of these diseases can be similar, and the context written about the patient can contain similar words and terms. So, vector matching can become even more technically challenging.

Accordingly, described herein, in certain embodiments, are systems and methods for AI-powered clinical decision support. Systems and methods herein can include an LLM configured with different modules to improve healthcare outcomes. For example, modules herein can be configured to assist clinicians with answering clinical reference questions, developing differential diagnoses, developing assessment and treatment plans, and drafting clinical documentation. Modules herein can be configured to assist clinicians with managing their personal clinical knowledge and accessing the knowledge databases of their health systems.

In an aspect, disclosed herein is an artificial intelligence (AI)-based clinical decision support platform. In some embodiments, the platform comprises a user input processing module configured to receive a clinical problem representation (CPR) based at least in part on an input provided by a user. In some embodiments, the platform comprises a context matching module configured to (1) process a prompt for refining the CPR and identify a suitable context, (2) provide the CPR along with one or more relevant context topics to a first large language model (LLM), and (3) use the first LLM to generate a first output comprising a preliminary clinical diagnosis and a context match relating to the CPR. In some embodiments, the platform comprises a retrieval-augmented generation (RAG) module configured to process the context match and the one or more relevant context topics from the context matching module using a physician-validated context library, to determine a context topic based on physician-validated schemas or clinical guidelines for pushing into a second LLM. In some embodiments, the platform comprises an output generation module configured to use the second LLM to process (1) the CPR, (2) the context based on the physician-validated schemas or clinical guidelines, and (3) one or more targeted prompts, to generate a second output comprising at least one of a differential diagnosis, an assessment of a health condition, or a treatment plan for the health condition.

Generally, retrieval-augmented generation (RAG) can be used to improve responses generated by generative artificial intelligence (AI) such as large language models (LLMs). In some cases, an LLM which includes RAG can be figured to implement a dual technique that merges elements of retrieval-based and LLMs to produce more accurate, sophisticated, and context-aware responses. For example, in a typical generative model, the LLM may independently generate responses based on training data. The training data may be general instead of specific to the context of the query or the training data may not be current (e.g., outdated). Augmenting the LLM with RAG can improve the generative process by retrieving context-relevant information from the training data. For example, when a query or input is received, an LLM which includes RAG can perform one or more information retrieval operations. The one or more retrieval operations may process a knowledge database for pertinent or contextual data. Retrieval-augmented generation can be configured to use a robust retrieval model to locate applicable documents, excerpts, or data units associated with the context of the query. An objective of these retrieval operations can include harnessing previously encoded knowledge and capitalizing on potential contextual clues to better answer the query. The retrieved data can then guide or inform the generative process by augmenting with contextual nuances and knowledge-specific insights. The integration of information retrieval and generative AI can allow the LLM to generate a more contextually rich and accurate response than with a standalone generative approach. Accordingly, an LLM which includes RAG can better process complex queries, generate more accurate and detailed responses, and provide information that better aligns with the original context of the query.

Figure 1B:
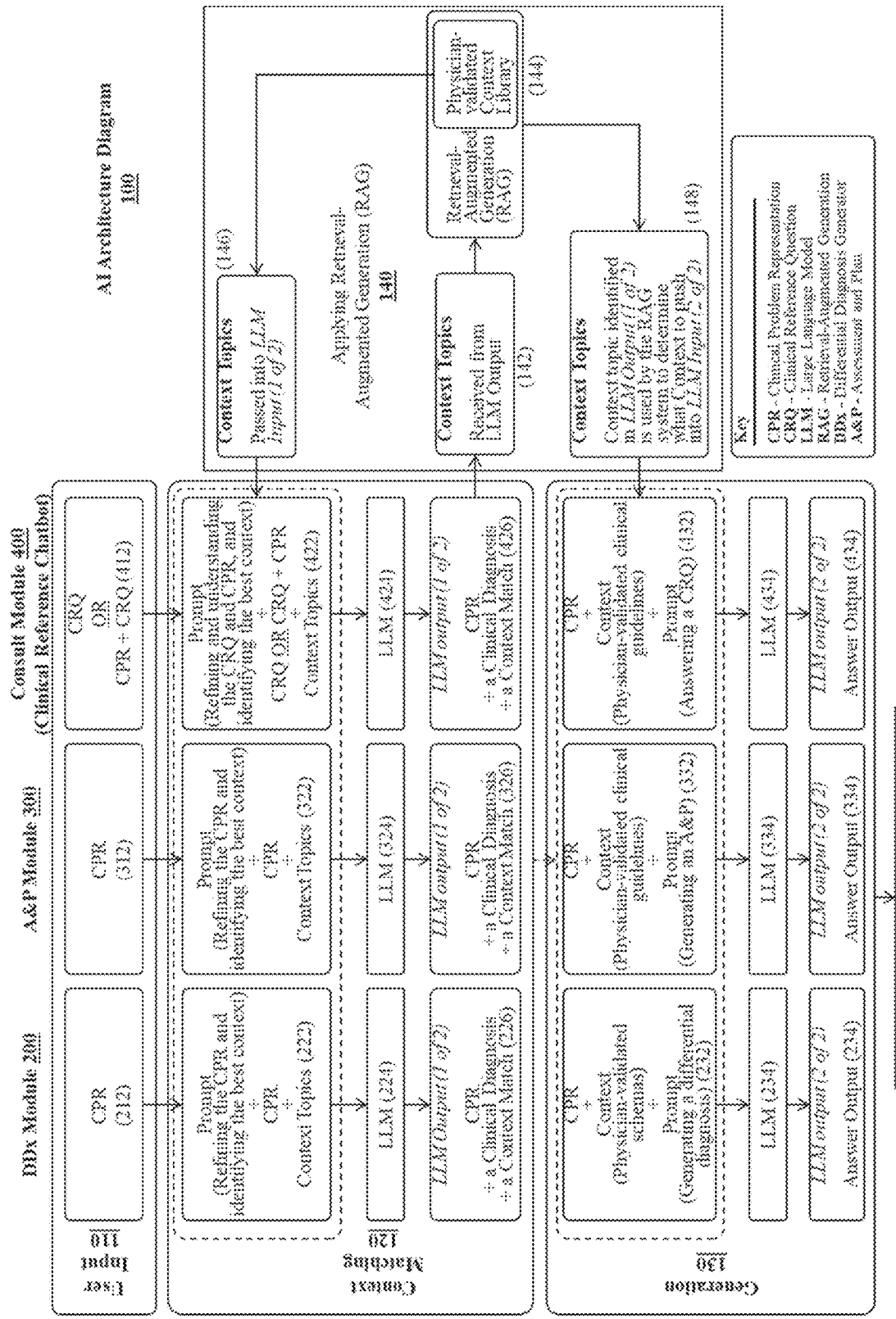

FIGS. 1A-1B illustrate example LLM platform or system architectures for performing methods herein. FIG. 1A illustrates an example high-level platform or system architecture for performing methods herein. In some cases, the system architecture can include processes for: receiving user inputs 110 from users (e.g., clinicians and patients), performing context matching 120 on user inputs 110, applying retrieval-augmented generation (RAG) 140 in a feedback manner to the context matching of 120, updating the context matching 120 based on applying the RAG 140, generating or updating user outputs 130 based on applying the RAG 140, and communicating (e.g., speech, text, or video) user outputs 150 to users to improve healthcare outcomes. In some cases, the user outputs 150 may be provided to or received by the AI-copilot module or the AI-notebook module described herein elsewhere. In some cases, data or information associated with the AI-copilot module or the AI-notebook module may be provided as inputs for inputs 110.

FIG. 1B illustrates an example detailed platform or system architecture for performing methods herein. In some cases, the LLM herein may include modules configured to perform specific functions. For example, modules described herein elsewhere can include: a module for generating a differential diagnosis (DDx) by the DDx module 200 of FIG. 2, a module for generating an assessment and plan (A&P) by the A&P module 300 of FIG. 3, a module for generating clinical references by the consult module 400 of FIG. 4. In some cases, each of the modules may be configured to use the same or similar LLM system architectures illustrated in FIGS. 1A-1B. In some cases, user outputs 150 associated with each module may be provided to or received by the AI-copilot module or the AI-notebook module described herein elsewhere. In some cases, data or information associated with the AI-copilot module or the AI-notebook module may be provided as inputs for inputs 110 associated with each module.

In some cases, the different modules described herein can be configured to receive inputs from or provide outputs to other modules associated with or external to the LLM herein. For example, other modules described herein can include the AI-copilot module and the AI-notebook module. In some cases, the different modules described herein can be accessed through a virtual platform. e.g., a cloud-based platform or a virtual store. In some cases, the different modules described herein can be accessed or purchased through a virtual store described herein elsewhere.

In some cases, the terms "system," "systems." "platform," "platforms," or "Glass AI" can be used interchangeably. In some cases, the system, platform, or Glass AI comprises the LLM with retrieval-augmented generation (RAG) described herein.

Systems and methods for generating Differential Diagnoses by the DDx Module

In some cases, the language learning model (LLM) disclosed herein can include a differential diagnosis generator (DDx) module 200 to generate an accurate or improved differential diagnosis for a patient. The DDx module 200 can be used by clinicians to expand their differential diagnosis for a patient's presentation. For example, the clinician can enter a patient summary into the DDx module 200. The patient summary can be similar to or the same as what they would communicate (e.g., speech, text, or video) when presenting a patient to another clinician for consultation. The DDx module 200 can analyze or process the patient summary and suggest a differential diagnosis that the clinician can consider. The DDx module 200 can determine, predict, or describe the various diagnostic possibilities. Also, the DDx module 200 can generate or describe the clinical reasoning, e.g., transparency of the model. Transparency of the model can make a given diagnosis more or less likely based on the clinician's input. Transparency of the model can make a given diagnosis more or less likely to be used by the clinician. The DDx module 200 can also suggest a diagnostic workup (e.g., radiology, biopsies, blood tests, and the like) that could confirm or exclude the diagnosis. The clinician may then decide whether to pursue the diagnostic workup for the various diagnoses generated by the DDx module 200. The LLM comprising the DDx module 200 can operate using an AI architecture configured to use a chain-of-thought prompt that mimics the thought processes of a master diagnostician. Also, the DDx module 200 can improve its outputs by being trained on complex diagnostic cases that can be curated for training the DDx module 200. In some cases, the curating can be performed by expert clinicians. In some cases, the curating can be performed by expert clinicians assisted by another LLM or the LLM herein.

For example, recognized herein is that a fundamental skill that a physician learns throughout their training can include forming broad and accurate differential diagnoses when encountering a patient. The ability of the physician to do this well can be important to ensure that the correct diagnostic workup and management plan will be utilized and lead to improved healthcare outcomes. For example, misdiagnosis of a patient can lead to worsening healthcare outcomes such as morbidities and mortalities. In some cases, the DDx module 200 can be trained and validated on clinical vignettes ranging from low to high complexity. In some cases, the clinical vignettes can include reports of clinical cases that provide insight into clinical practice for improving clinical practice, education, and research. In some cases, the clinical vignettes can be unstructured abstracts of 200 words or less and text of 2,000 words or less. The outputs of the DDx module 200 can be validated based on at least two metrics; precision (e.g., the correct diagnosis was its number 1 answer) and accuracy (e.g., the diagnosis was in its top 5 differential).

In some cases, the DDx module 200 can be developed using different AI architectures, depending on the use case, such as different retrieval augmentation strategies, different context databases, or different foundational models. In some cases, the improved performance of the DDx module 200 can be determined by comparison to other base LLMs using the same dataset or parameters, e.g., comparison with ChatGPT™ by OpenAI® or MedLM® by Google®.

Figure 2:
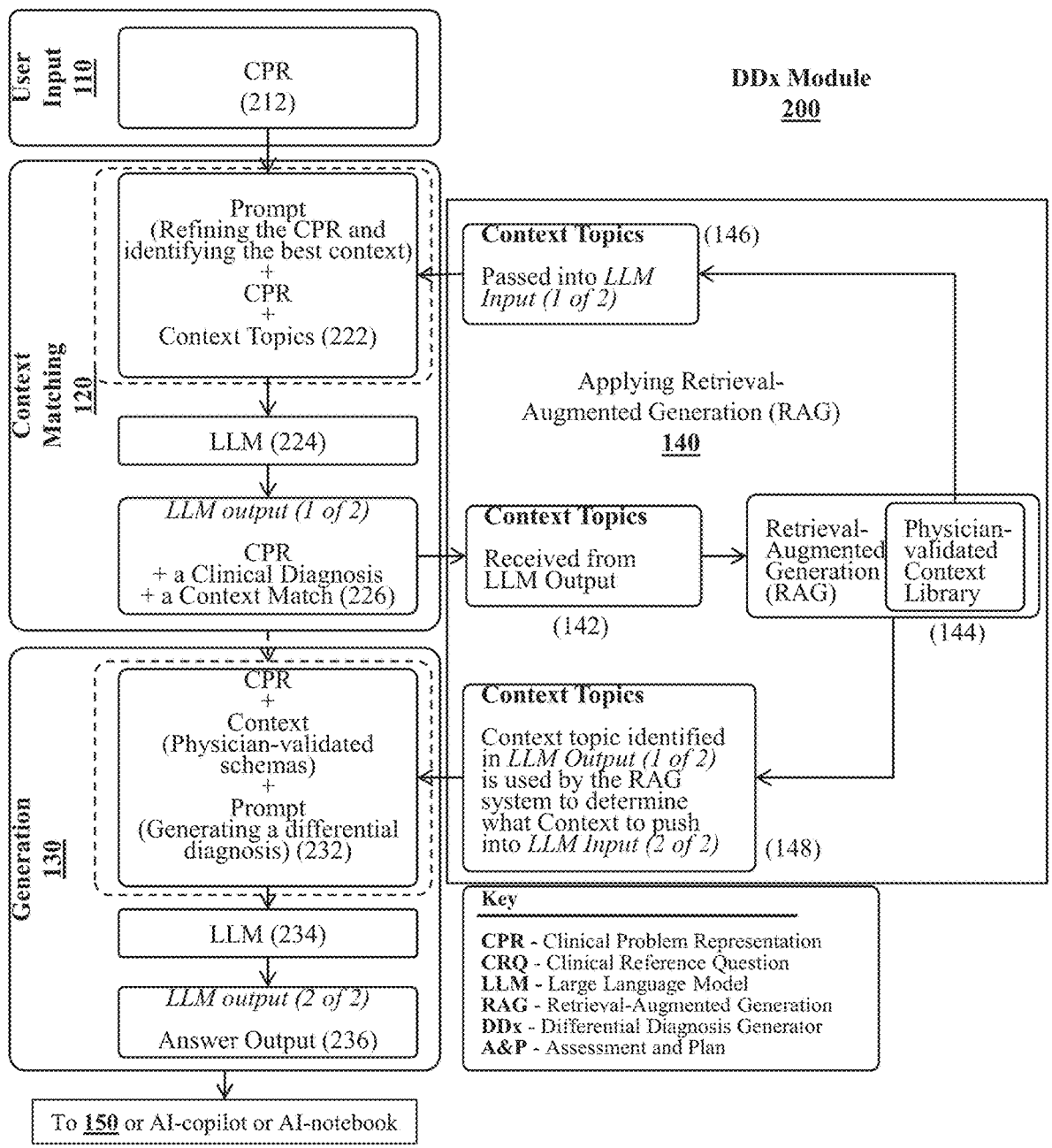
FIG. 2 illustrates an example detailed platform or system architecture for performing methods herein associated with generating a differential diagnosis (DDx) by the DDx module, in accordance with some embodiments. The DDx module can include processes for receiving user inputs, performing context matching, applying retrieval-augmented generation (RAG) in a feedback loop, generating user outputs, and communicating user outputs.

FIG. 2 illustrates an example detailed platform or system architecture for performing methods herein associated with generating a differential diagnosis (DDx) by the DDx module 200. The DDx module 200 may be configured to use the same or similar LLM system architectures illustrated in FIGS. 1A-1B but which is further configured to provide the specific functionality of the DDx module 200.

Receiving User Inputs

In some embodiments, the platform comprises a user input processing module configured to receive a clinical problem representation (CPR) based at least in part on an input provided by a user.

For example, FIG. 2 illustrates an example flow for receiving or generating user inputs 110 associated with generating a DDx by the DDx module 200. The DDx module 200 can enable users (e.g., clinicians or patients) to provide improved specific and complete inputs for questions they need answered. In some cases, the user inputs 110 can be associated with a clinical problem representation (CPR) 212. For example, a user (e.g., a clinician) may provide as user inputs 110 to the DDx module 200 that, "the patient is a 65 year old woman with a history diabetes and hyperlipidemia presenting with acute-onset chest pain and diaphoresis found to have hyperacute T-waves without ST elevation." The DDx module 200 can process the user inputs 110 to automatically generate the DDx. In some embodiments, the user input processing module is further configured to generate the CPR. The CPR may be associated with a patient presenting to a clinician with a healthcare issue. The healthcare issue may be associated with panels, topics, and variants. Panels can include, for example, the specific areas of healthcare, e.g., radiology for a patient seeking breast care. Topics can include, for example, specific diseases that fall under each panel, e.g., a patient with breast cancer. Variants can include, for example, presentations within each topic, e.g., age of the patient with breast cancer.

FIG. 9A illustrates receiving or generating user inputs 110 associated with the DDx module 200. In some cases, the user inputs 110 can be received through a graphical user interface (GUI) or device as illustrated in FIG. 9A. In some cases, a user (e.g., a clinician or a patient) can communicate the user inputs 110 to the GUI or device. In some cases, the user can communicate the user inputs 110 by text, speech, or video. In some cases, the user inputs 110 associated with the DDx module 200 may be received from or provided by the AI-copilot module or the AI-notebook module described herein elsewhere. In some cases, data or information associated with the AI-copilot module or the AI-notebook module may be received as inputs for inputs 110 associated with the DDx module 200. In some cases, the GUI or device comprises the AI-copilot module or the AI-notebook module.

FIG. 9A further illustrates an example prompt associated with the CPR or CRQ. In some cases, the prompt may instruct the user to provide specific data associated with the CPR or CRQ. For example, the prompt may instruct the user to include: age, relevant past medical history, medications, presenting symptoms, associated symptoms, descriptions of relevant studies (e.g., labs and imaging), the illness course, and any additional information a user might include when consulting another user, e.g., a clinician or physician. The GUI or device can provide functions for causing systems and methods herein to invoke execution of the DDx module 200, the A&P module 300, or the consult module 400.

Performing Context Matching from User Inputs

In some embodiments, the platform comprises a context matching module configured to (1) process a prompt for refining the CPR and identify a suitable context, (2) provide the CPR along with one or more relevant context topics to a first large language model (LLM), and (3) use the first LLM to generate a first output comprising a preliminary clinical diagnosis and a context match relating to the CPR.

For example, FIG. 2 further illustrates an example flow for performing context matching 120 associated with generating a DDx by the DDx module 200. The DDx module 200 can be configured to use prompt engineering, the CPR, context topics, and a base LLM (e.g., ChatGPT™) to perform context matching 120 from user inputs 110 and to optimize embedding for the RAG module 140.

In some cases, process 120 of the DDx module 200 can include process 222 for using prompt engineering to determine the improved, best, or optimal context for the CPR and for generating context topics or refining context topics. In some cases, process 120 of the DDx module 200 can include process 224 for providing the CPR or refined CPR, the results from the prompt engineering, and the context topics to a base LLM. In some cases, process 120 of the DDx module 200 can include process 224 for using the base LLM to process the CPR or refined CPR, the results from the prompt engineering, and the context topics to further extract meaning from the user inputs 110. In some cases, process 120 of the DDx module 200 can include process 226 for transmitting the output of the base LLM to the RAG module 140 for iteratively applying RAG. Alternatively, process 226 can transmit the output of the base LLM directly to process 130 of the DDx module 200, e.g., the RAG module 140 can be bypassed. In some cases, the output of process 226 can include the CPR or refined CPR, a clinical diagnosis, or one or more context matches. In some cases, the output of process 226 can include context topics determined by the base LLM for transmittal to the RAG module 140.

Applying Retrieval-Augmented Generation (RAG) for Context Matching

In some embodiments, the platform comprises a retrieval-augmented generation (RAG) module configured to process the context match and the one or more relevant context topics from the context matching module using a physician-validated context library, to determine a context topic based on physician-validated schemas or clinical guidelines for pushing into a second LLM. In some embodiments, the RAG module is further configured to provide or refine the one or more relevant context topics iteratively back to the context matching module for subsequent pushing into the first LLM. In some embodiments, the context matching module is further configured to process another prompt for refining the CPR.

For example, FIG. 2 further illustrates an example flow for applying retrieval-augmented generation (RAG) associated with generating a DDx by the DDx module 200. The RAG module 140 can be configured to receive the output of process 226 and to perform embedding matching with a physician-validated context library. In some cases, the physician-validated context library is generated by expert clinicians or physicians who analyze and validate data associated the CPR. In some cases, the data is provided, received, or generated in the form of panels, topics, and variants described herein elsewhere. In some cases, the output of RAG module 140 can be iteratively provided or transmitted to process 222 to update or refine the context matching 120. In some embodiments, the RAG module is further configured to use one or more prompts to improve processing of the context match and the one or more relevant context topics, and wherein the one or more prompts comprises chain-of-thought prompt engineering. In some embodiments, the RAG module is further configured to use N-shot learning to improve processing of the context match and the one or more relevant context topics, and wherein the N-shot learning comprises at least one learning example.

In some cases, process 142 of the RAG module 140 can include processes for receiving context topics from process 226 of the DDx module 200. In some embodiments, the context matching module is further configured to process another prompt for refining the CPR. In some cases, process 144 of the RAG module 140 can include processes for embedded matching (e.g., via RAG) with the physician-validated context library. In some cases, the output of process 144 can include refined context topics. In some cases, process 146 of the RAG module 140 can include processes for providing or transmitting the refined context topics to process 222 of the DDx module 200. In some cases, process 120 of the DDx module 200 can then use the refined context topics to further refine the prompt engineering, the CPR, or the context topics.

In some cases, the refinement process of processes 142, 144, and 146 of the RAG module 140 can be iteratively performed a predetermined number of times until an improved, accurate, or reliable answer is provided when generating user outputs 130. In some cases, the number of iterations is at least about 1, 10, 100, 1000, 10000, or more iterations, including increments therein. In some cases, the number of iterations is at most about 10000, 1000, 100, 10, or less iterations, including increments therein. In some cases, an accurate answer is at least about 60%, 70%, 80%, 90%, or more accurate, including increments therein. In some cases, the user (e.g., a clinician) may determine the number of iterations based on the reliability of the answers provided by the platform herein, e.g., reliability of the DDx. In some cases, the reliability may be based on a confidence of the user in the answer. In some cases, the answer is provided with a confidence of at least about 60%, 70%, 80%, 90%, or more, including increments therein.

Generating and Communicating User Outputs

In some embodiments, the platform comprises an output generation module configured to use the second LLM to process (1) the CPR, (2) the context based on the physician-validated schemas or clinical guidelines, and (3) one or more targeted prompts, to generate a second output comprising at least one of a differential diagnosis, an assessment of a health condition, or a treatment plan for the health condition.

For example, FIG. 2 further illustrates an example flow for generating user outputs 130 associated with generating a DDx by the DDx module 200. The DDx module 200 can be configured to generate accurate, high-quality, high-fidelity, clear, and tailored output for the user, e.g., a clinician or patient. In some cases, the DDx module 200 can be configured to combine user inputs, relevant context topics, and specialized meta-prompts with prompt engineering to generate improved, best, or optimal outputs for the user. In some cases, the DDx module 200 can improve the accuracy or confidence of the DDx by at least about 5%, 10%, 15%, 20%, or more, including increments therein, compared to a LLM that does not use RAG. For example, process 130 of the DDx module 200 can be configured to use the CPR or refined CPR, prompt engineering, refined context topics, and a base LLM 234 (e.g., ChatGPT™). In some cases, the base LLM 224 is different than the base LLM 234. In some cases, the base LLM 224 is the same as the base LLM 234. In some cases, the base LLM 224 is updated, e.g., by processes performed by the RAG module 140, to generate the base LLM 234.

In some cases, process 130 of the DDx module 200 can be configured to receive the outputs of process 148 of the RAG module 140. In some cases, process 232 of the DDx module 200 can include processes for refining the CPR, refining contexts comprising physician-validated schemas, or refining engineering prompts. In some cases, process 130 of the DDX module 200 can include process 234 for providing the CPR or refined CPR, the results from the prompt engineering, or the refined context topics to a base LLM. In some cases, process 130 of the DDx module 200 can include process 234 for using the base LLM to process the CPR or refined CPR, the results from the prompt engineering, or the refined context topics to generate user outputs 236. In some cases, process 130 can include process 236 for transmitting the output of the base LLM. In some cases, the output of process 236 can include an answer, e.g., the differential diagnosis. In some cases, a user (e.g., a clinician) may apply the differential diagnosis when a confidence in the diagnosis is at least about 60%, 70%, 80%, 90%, or more, including increments therein. In some cases, applying the differential diagnosis can include providing the differential diagnosis to the patient. In some cases, applying the differential diagnosis can include providing the differential diagnosis to the A&P module 300, the consult module 400, the AI-copilot module, or the AI-notebook module.

Figure 9B:
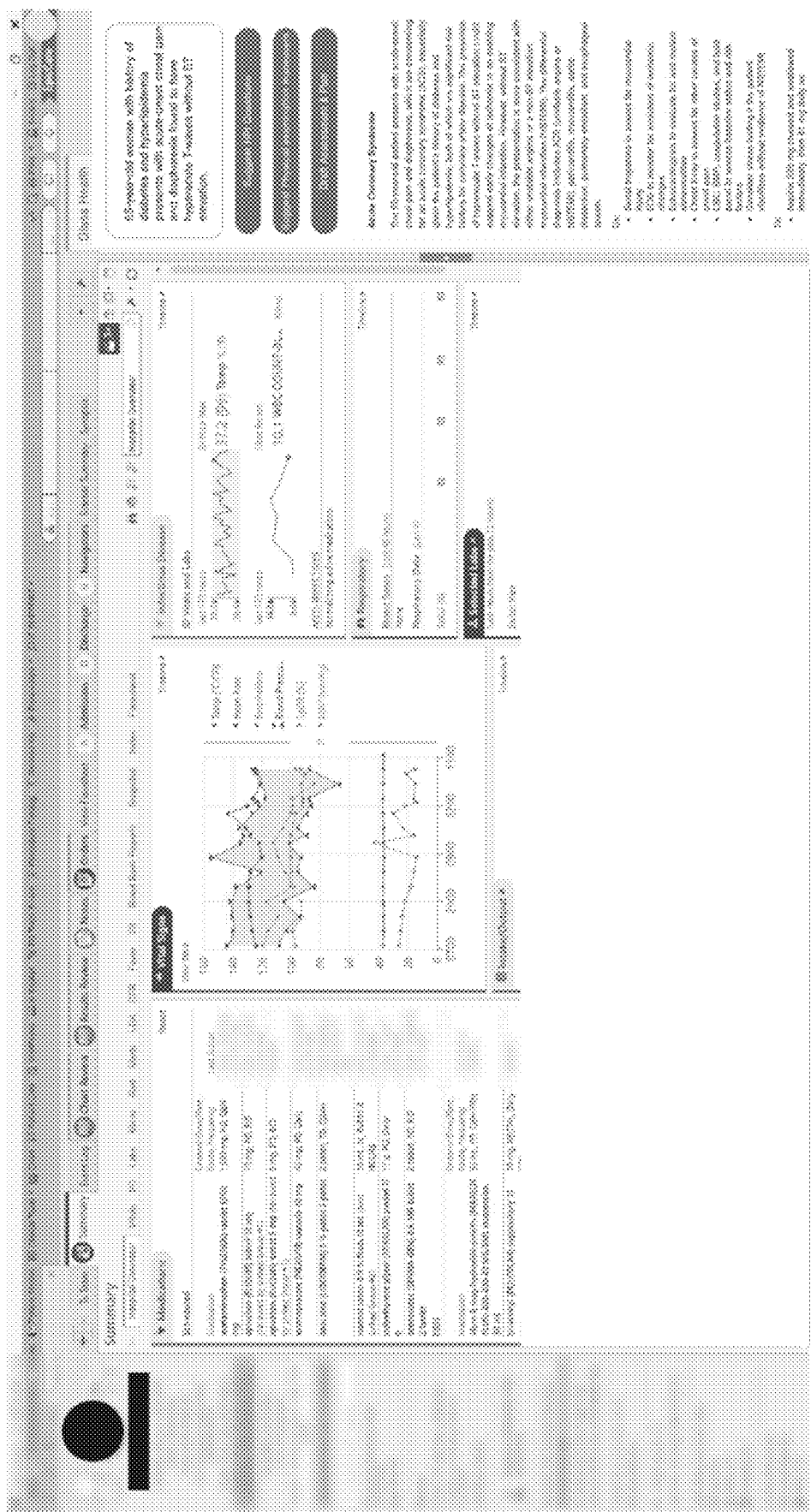
Figure 10A:
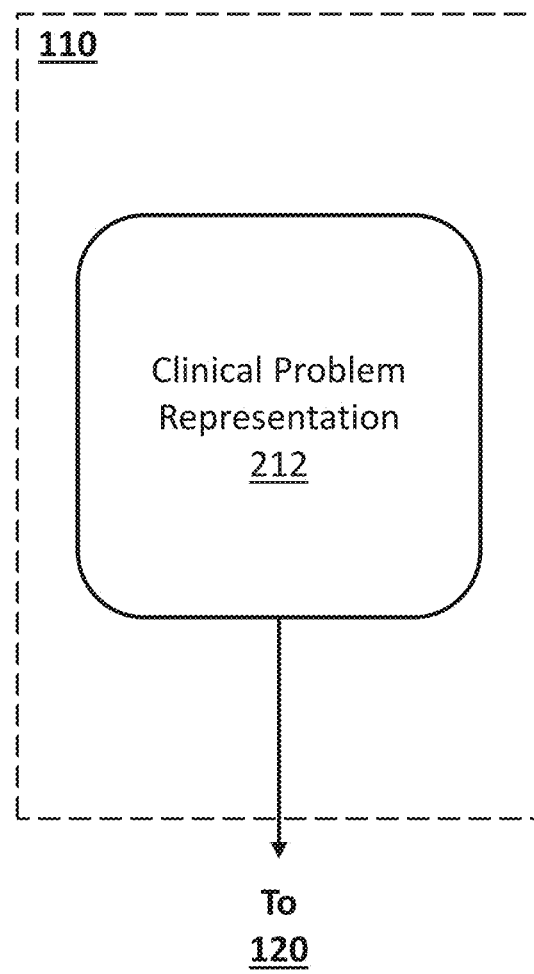
FIGS. 10A-10D illustrate alternative example detailed platform or system architectures for performing methods herein associated with generating a differential diagnosis (DDx) by the DDx module, in accordance with some embodiments. The DDx module can include processes for receiving user inputs, performing context matching, applying retrieval-augmented generation (RAG) in a feedback loop, generating user outputs, and communicating user outputs.
Figure 10B:
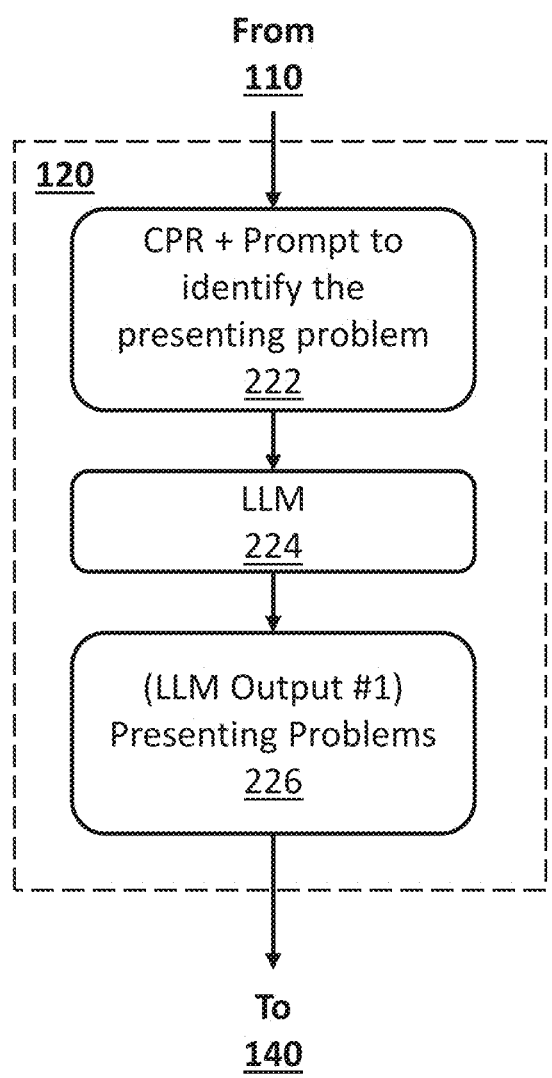
Figure 10C:
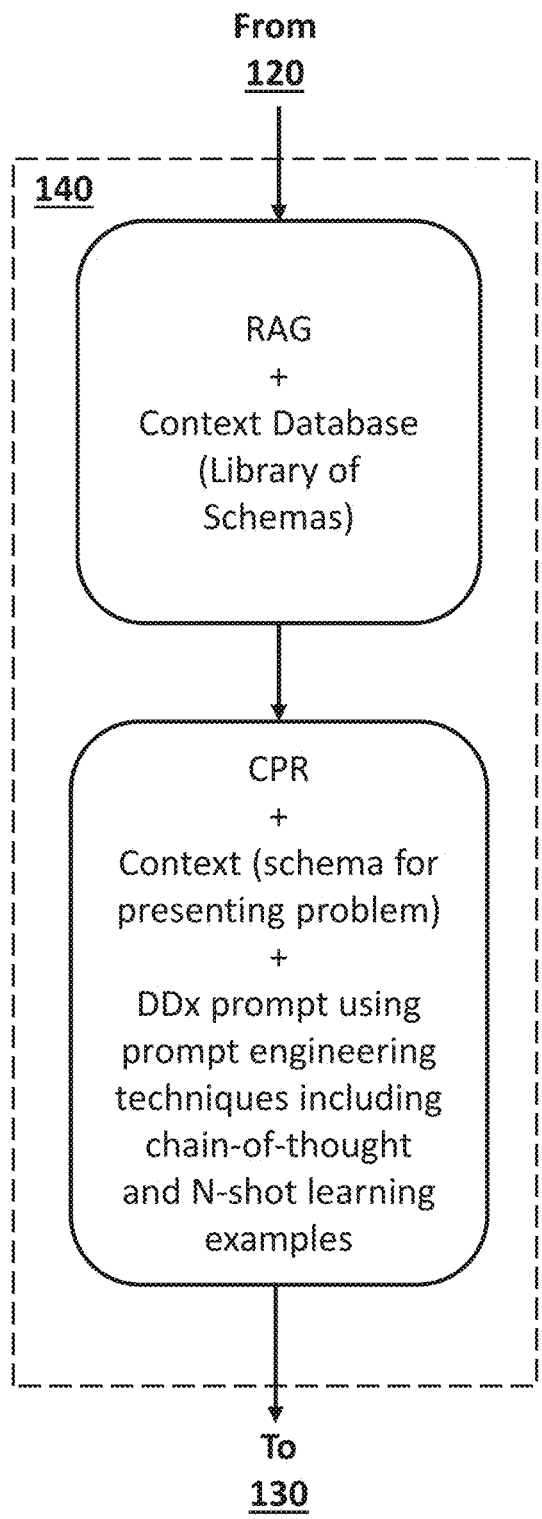
Figure 10D:
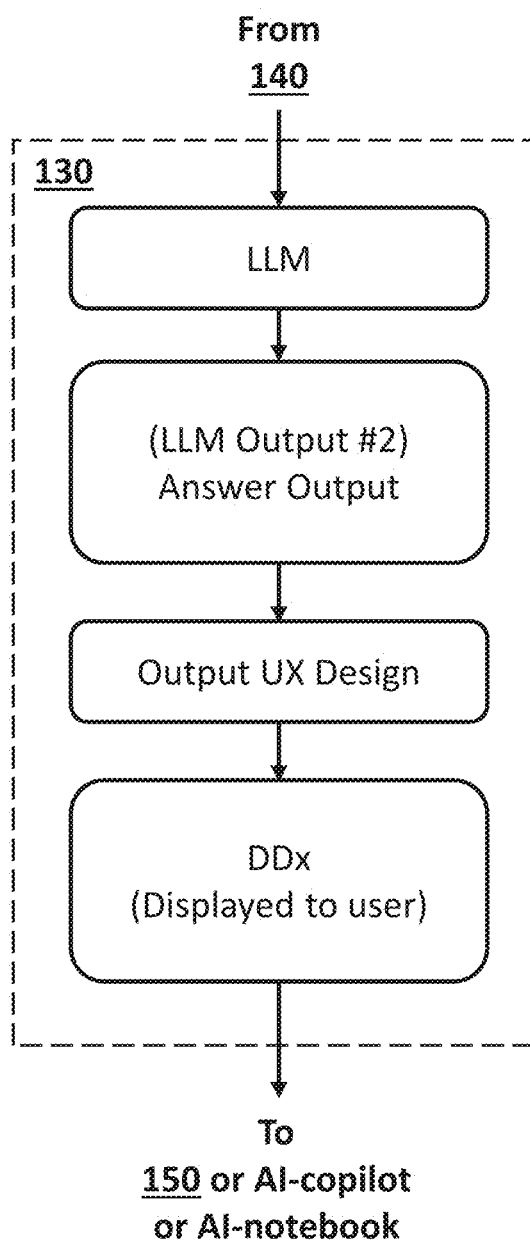
Figure 11A:
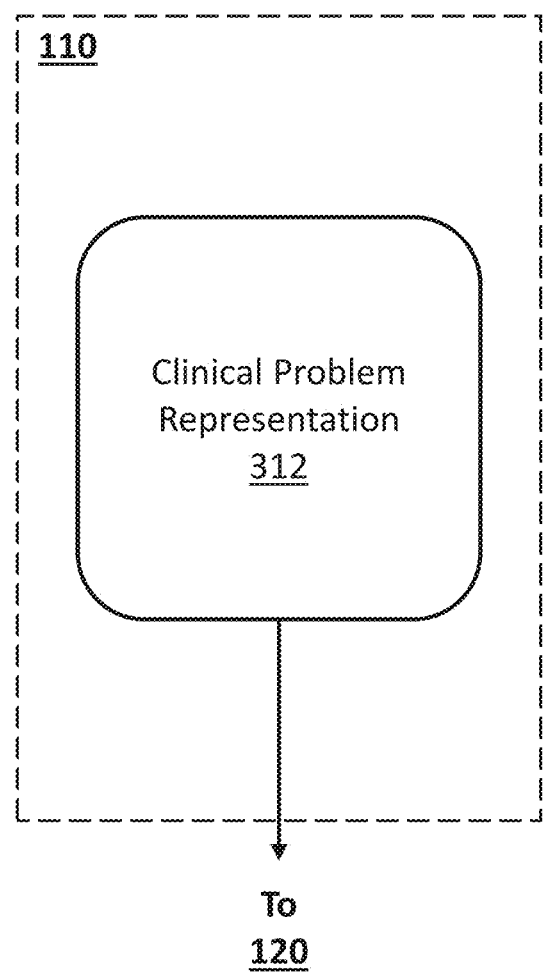
FIGS. 11A-11D illustrates alternative example detailed platform or system architectures for performing methods herein associated with generating an assessment and plan (A&P) by the A&P module, in accordance with some embodiments. The A&P module can include processes for receiving user inputs, performing context matching, applying retrieval-augmented generation (RAG) in a feedback loop, generating user outputs, and communicating user outputs.
Figure 11B:
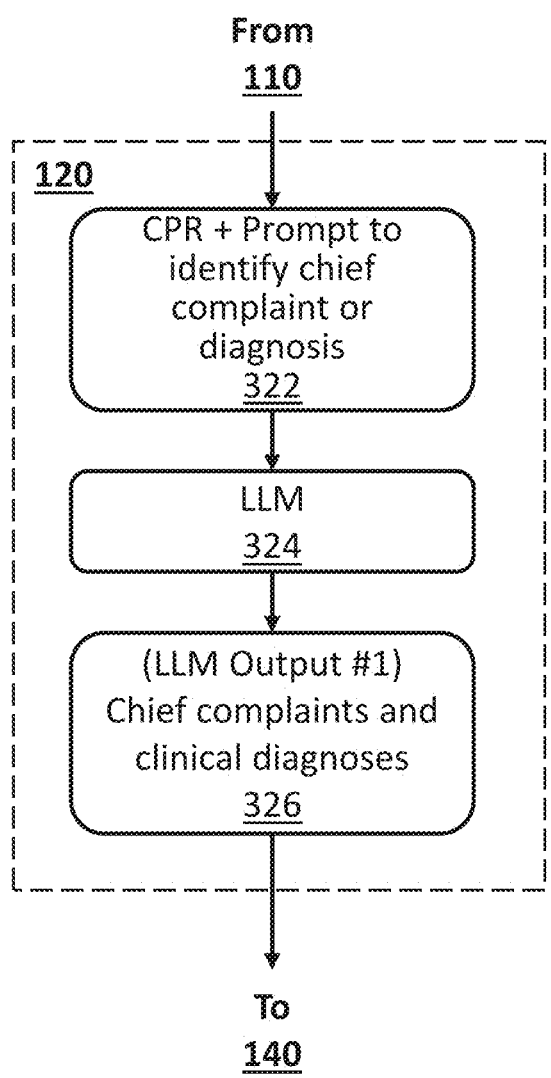
Figure 11C:
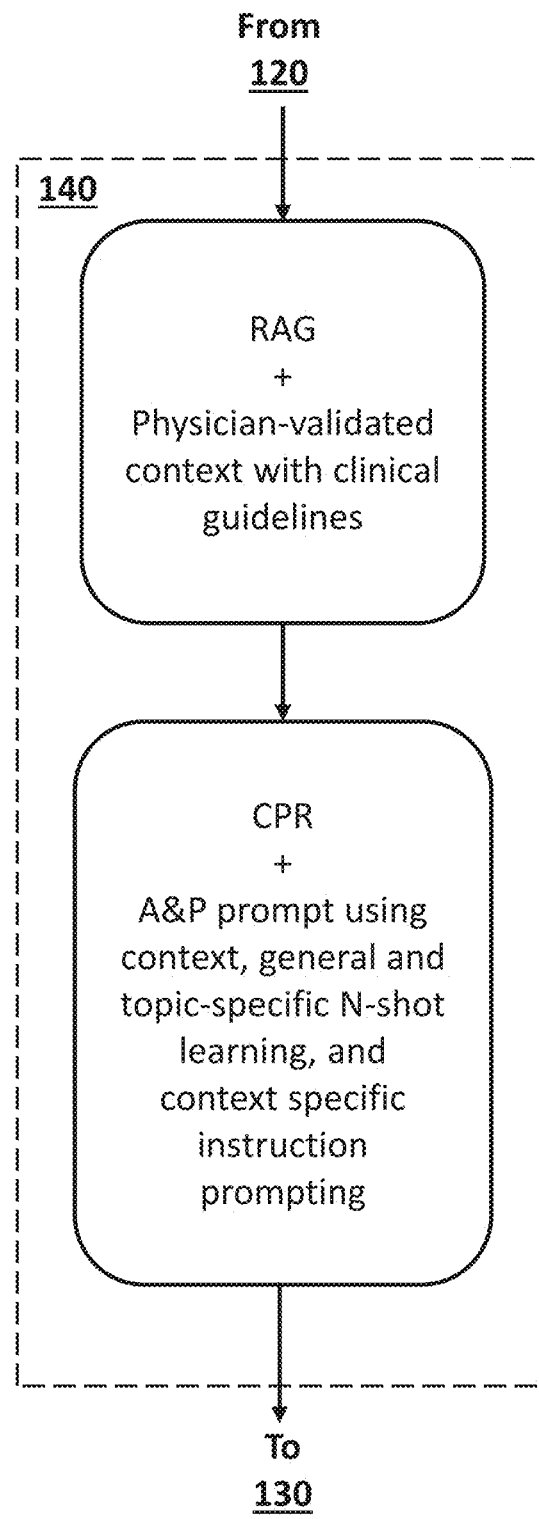
Figure 11D:
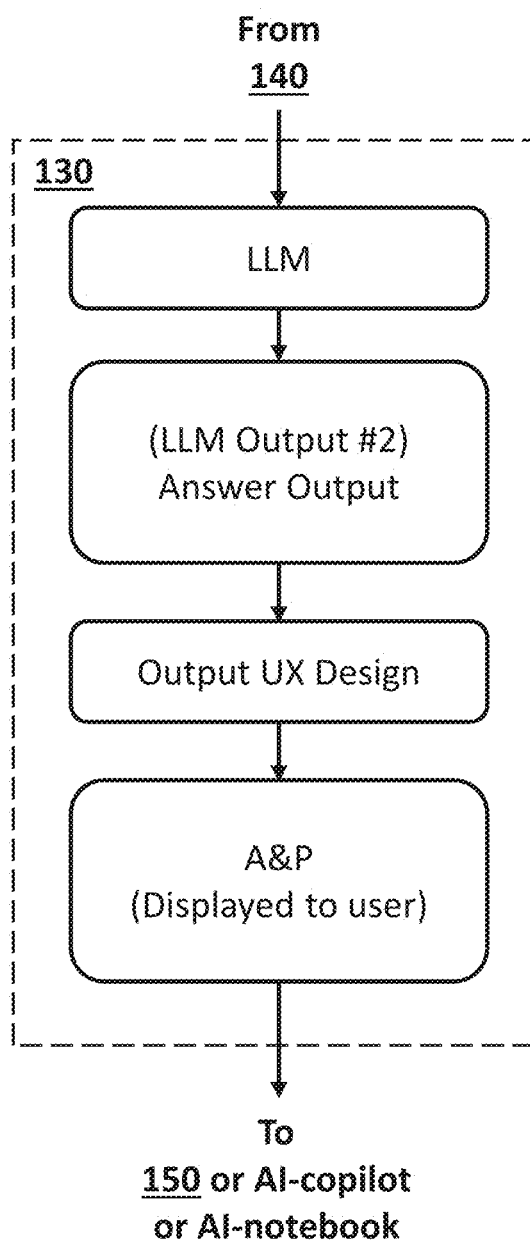
Figure 12A:
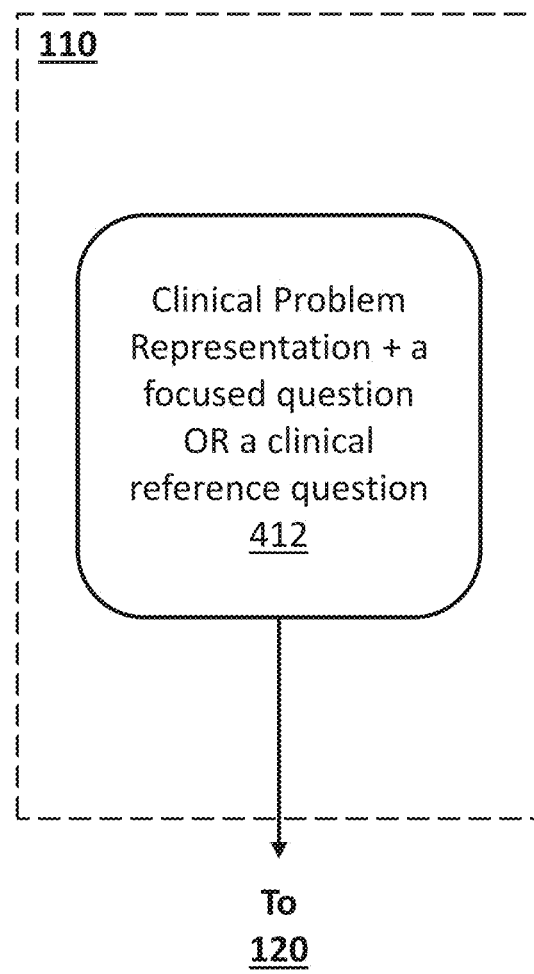
FIGS. 12A-12D illustrate alternative example detailed platform or system architectures for performing methods herein associated with generating a consult or clinical reference by the consult module, in accordance with some embodiments. The consult module can include processes for receiving user inputs, performing context matching, applying retrieval-augmented generation (RAG) in a feedback loop, generating user outputs, and communicating user outputs.
Figure 12B:
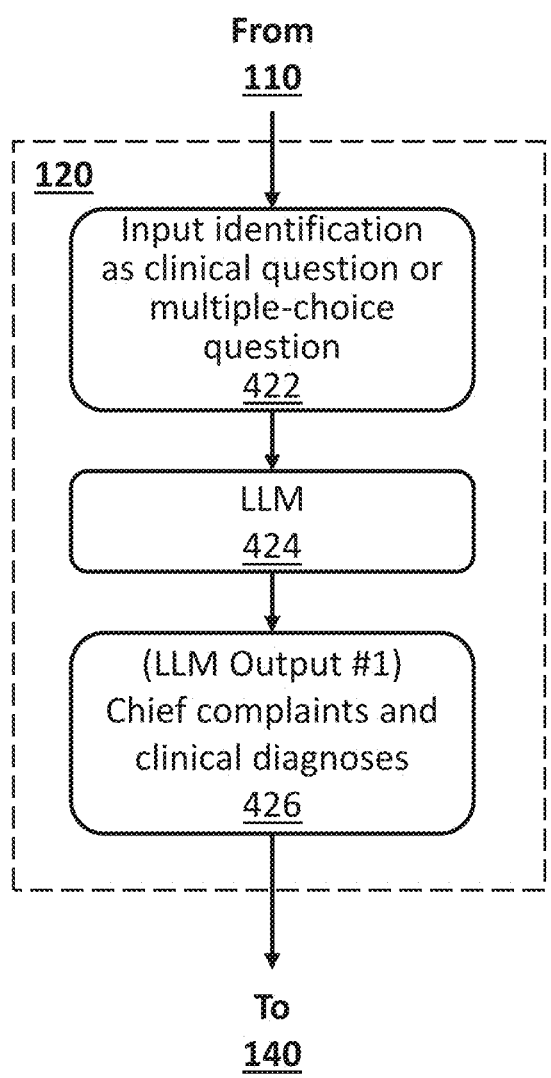
Figure 12C:
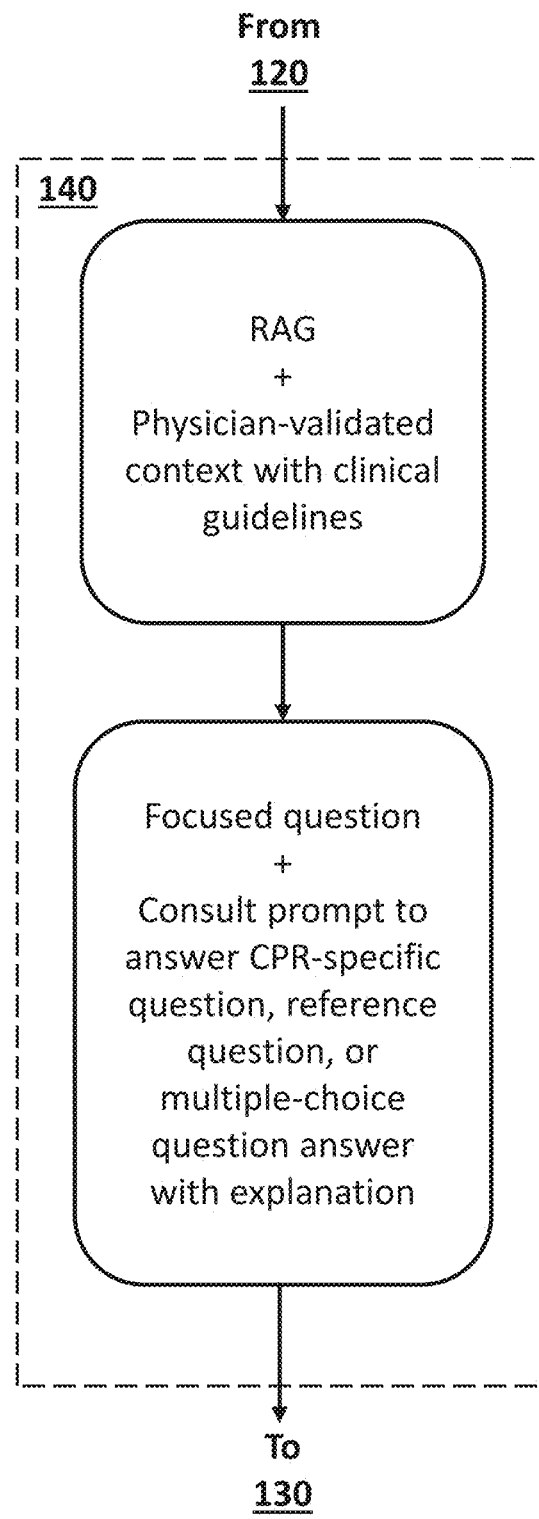
Figure 12D:
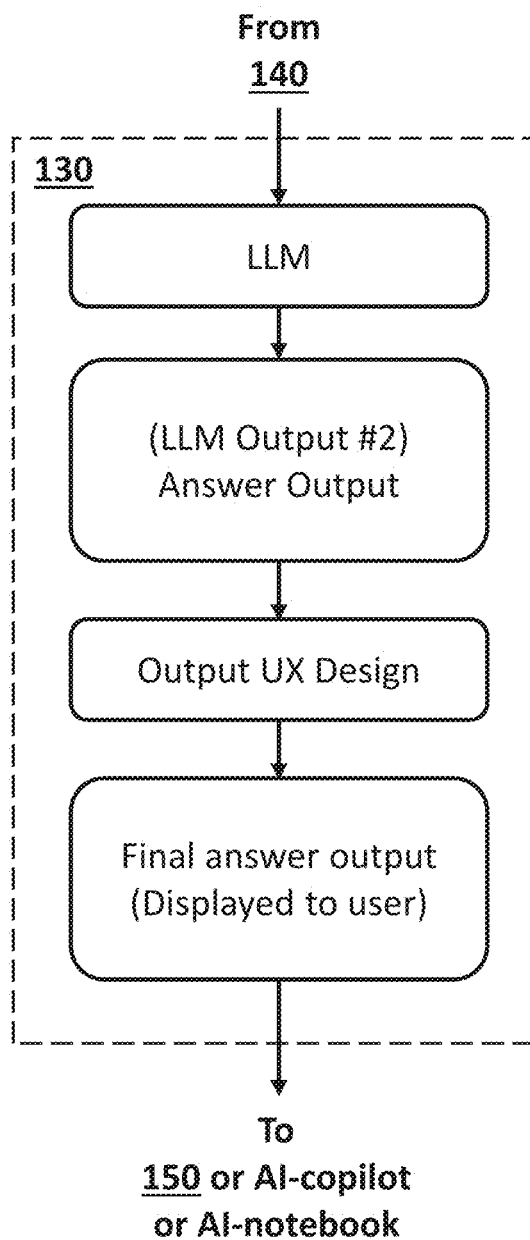
Figure 13:
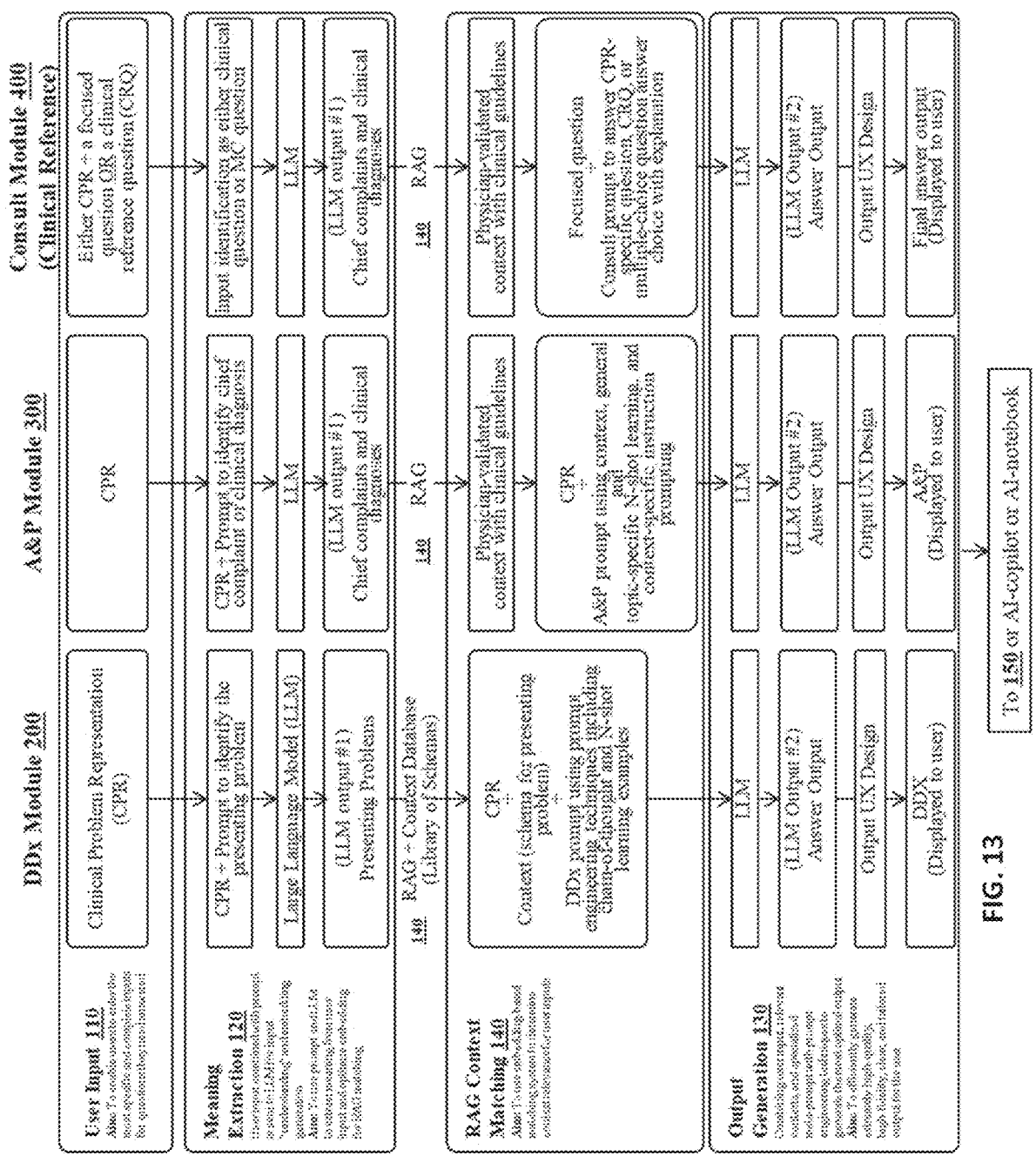
FIG. 13 illustrates alternative example detailed platform or system architectures for performing methods herein of FIGS. 10A-10D, FIGS. 11A-11D, and FIGS. 12A-12D, in accordance with some embodiments.

For example, FIG. 2 further illustrates communicating user outputs 150. In some cases, the user outputs 150 associated with the DDx module 200 may be provided to or received by the AI-copilot module or the AI-notebook module described herein elsewhere. In some cases, data or information associated with the AI-copilot module or the AI-notebook module may be provided as inputs for inputs 110 associated with the DDx module 200. In some cases, user outputs 150 are communicated to or displayed by a graphical user interface (GUI) or device as illustrated in FIG. 9B. In some cases, the GUI or device comprises the AI-copilot module or the AI-notebook module. In some cases, the user outputs 150 can be accessed or purchased through a virtual store described herein elsewhere.

FIG. 9B illustrates an example GUI or device configured to communicate the user outputs 150 associated with the DDx module 200. For example, the user outputs 150 may be communicated through the GUI or device by text, speech, or video. In some cases, the user outputs 150 may be communicated by text in the form of a report. In some cases, the GUI or device can provide functions for causing systems and methods herein to invoke sharing or archiving of the user outputs 150. In some cases, the user outputs 150 can be shared with the user, e.g., the clinician or the patient. In some cases, the user outputs 150 can be shared with the AI-copilot module or the AI-notebook module described herein elsewhere. In some cases, the user outputs may be shared with or transmitted to the A&P module 300 or the consult module 400.

FIGS. 10A-10E illustrate an alternative example detailed platform or system architecture for performing methods herein associated with generating a differential diagnosis (DDx) by the DDx module.

Systems and Methods for Generating Assessments and Plans by the a&P Module

In some cases, the language learning model (LLM) disclosed herein can include an assessment and plan (A&P) module 300 to generate an improved comprehensive and accurate assessment and plan based on a patient's presentation. For example, the clinician can enter a patient summary into the A&P module 300. The patient summary can be similar to or the same as what they would communicate (e.g., speech, text, or video) when presenting a patient to another clinician for consultation. The A&P module 300 can analyze the patient summary and determine, predict, or suggest an assessment and plan that can include an analysis (e.g., a report) of the patient presentation. In some cases, the A&P module 300 can determine, predict, or suggest diagnostic workups and next steps in terms of treatment and management. In some cases, the A&P module 300 can work using an AI architecture that involves analyzing the patient summary in a similar or same manner as the DDx module 200. In some cases, the outputs of the A&P module 300 can be provided to another module to generate the assessment and plan. For example, the A&P module 300 may consider or use a context library of physician-validated context.

For example, recognized herein is that in patient encounters, it is a role of the clinician to create a detailed assessment and plan that can serve as a roadmap that reflects the thinking of the clinicians to which pathology ails the patient and how the clinician will both confirm this assumption and subsequently manage the healthcare of the patient. In some cases, the A&P module 300 can provide high-quality and specific recommendations rather than just general clinical reference information. In some cases, the A&P module 300 can be trained and validated using a large data repository of clinical presentations. Independent evaluators, such as expert clinicians, can grade the outputs of the A&P module 300 along at least 5 parameters; 1. Accuracy (e.g., Is the assessment accurate? Is this the likely pathology affecting the patient); 2. Completeness (e.g., Is the answer complete? Are their components missing? Is there sufficient detail?); 3. Harm ratio (e.g., Could the management plan cause harm to a patient or help the patient?); 4. Reasoning (e.g., Is the reasoning of the response sound?); and 5. Citation (e.g., are the provided references correct or hallucinations?). In some cases, the improved performance of the A&P module 300 can be determined by comparison to other base LLMs, using the same dataset or parameters, e.g., comparison with ChatGPT™ by OpenAI® or MedLM® by Google®

Figure 3:
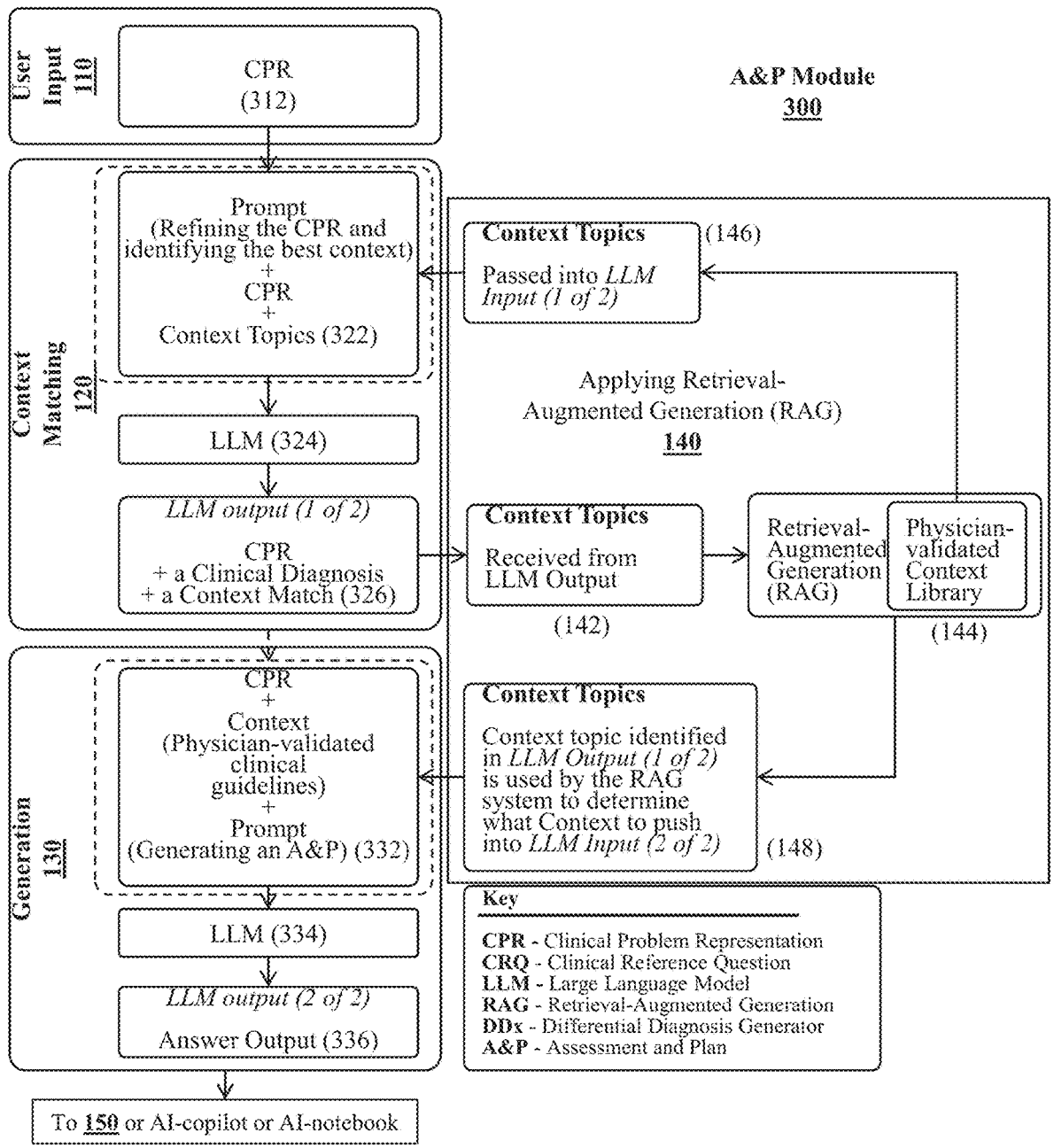
FIG. 3 illustrates an example detailed platform or system architecture for performing methods herein associated with generating an assessment and plan (A&P) by the A&P module, in accordance with some embodiments. The A&P module can include processes for receiving user inputs, performing context matching, applying retrieval-augmented generation (RAG) in a feedback loop, generating user outputs, and communicating user outputs.

FIG. 3 illustrates an example detailed system architecture for performing methods herein associated with generating an assessment and plan by the A&P module 30). The A&P module 300 may be configured to use the same or similar LLM system architectures illustrated in FIGS. 1A-1B but which is further configured to provide the specific functionality of the A&P module 300.

Receiving User Inputs

In some embodiments, the platform comprises a user input processing module configured to receive a clinical problem representation (CPR) based at least in part on an input provided by a user.

FIG. 3 illustrates an example flow for receiving or generating user inputs 110 associated with generating an assessment and plan by the A&P module 300. The A&P module 300 can enable users (e.g., clinicians or patients) to provide the most specific and complete inputs for questions they need answered. In some cases, the inputs can be associated with a clinical problem representation (CPR) 312. For example, a user (e.g., a clinician) may provide as user inputs 110 to the A&P module 300 that, "the patient is a 65 year old woman with a history diabetes and hyperlipidemia presenting with acute-onset chest pain and diaphoresis found to have hyperacute T-waves without ST elevation." The A&P module 300 can process the user inputs 110 to automatically generate the A&P In some embodiments, the user input processing module is further configured to generate the CPR. The CPR may be associated with a patient presenting to a clinician with a healthcare issue. The healthcare issue may be associated with panels, topics, and variants. Panels can include, for example, the specific areas of healthcare, e.g., radiology for a patient seeking breast care. Topics can include, for example, specific diseases that fall under each panel, e.g., a patient with breast cancer. Variants can include, for example, presentations within each topic, e.g., age of the patient with breast cancer.

FIG. 9A illustrates receiving or generating user inputs 110 associated with the A&P module 300. In some cases, the user inputs 110 are received through a graphical user interface (GUI) or device as illustrated in FIG. 9A. In some cases, a user (e.g., a clinician or a patient) can communicate the user inputs 110 to the GUI or device. In some cases, the user can communicate the user inputs 110 by text, speech, or video. In some cases, the user inputs 110 associated with the A&P module 300 may be received from or provided by the AI-copilot module or the AI-notebook module described herein elsewhere. In some cases, data or information associated with the AI-copilot module or the AI-notebook module may be received as inputs for inputs 110 associated with the A&P module 300. In some cases, the GUI or device comprises the AI-copilot module or the AI-notebook module.

FIG. 9A further illustrates an example prompt associated with the CPR or CRQ. In some cases, the prompt may instruct the user to provide specific data associated with the CPR or CRQ. For example, the prompt may instruct the user to include: age, relevant past medical history, medications, presenting symptoms, associated symptoms, descriptions of relevant studies (e.g., labs and imaging), the illness course, and any additional information a user might include when consulting another user, e.g., a clinician or physician. The GUI or device can provide functions for causing systems and methods herein to invoke execution of the DDx module 200, the A&P module 300, or the consult module 400.

Performing Context Matching from User Inputs

In some embodiments, the platform comprises a context matching module configured to (1) process a prompt for refining the CPR and identify a suitable context, (2) provide the CPR along with one or more relevant context topics to a first large language model (LLM), and (3) use the first LLM to generate a first output comprising a preliminary clinical diagnosis and a context match relating to the CPR.

For example, FIG. 3 further illustrates an example flow for performing context matching 120 associated with generating an assessment and plan by the A&P module 300. The A&P module 300 can be configured to use prompt engineering, the CPR, context topics, and a base LLM (e.g., ChatGPT™) to perform context matching 120 from user inputs 110 and to optimize embedding for the RAG module 140.

In some cases, process 120 of the A&P module 300 can include process 322 for using prompt engineering to determine the improved, best or, optimal context for the CPR and for generating context topics or refining context topics. In some cases, process 120 of the A&P module 300 can include process 324 for providing the CPR or refined CPR, the results from the prompt engineering, and the context topics to a base LLM. In some cases, process 120 of the A&P module 300 can include process 324 for using the base LLM to process the CPR or refined CPR, the results from the prompt engineering, and the context topics to further extract meaning from the user inputs 110. In some cases, process 120 of the A&P module 300 can include process 326 for transmitting the output of the base LLM to the RAG module 140 for iteratively applying RAG. Alternatively, process 326 can transmit the output of the base LLM directly to process 130 of the A&P module 300, e.g., the RAG module 140 can be bypassed. In some cases, the output of process 326 can include the CPR or refined CPR, a clinical diagnosis, or one or more context matches. In some cases, the output of process 326 can include context topics determined by the base LLM for transmittal to the RAG module 140, include.

Applying retrieval-Augmented Generation (RAG) for Context Matching

In some embodiments, the platform comprises a retrieval-augmented generation (RAG) module configured to process the context match and the one or more relevant context topics from the context matching module using a physician-validated context library, to determine a context topic based on physician-validated schemas or clinical guidelines for pushing into a second LLM. In some embodiments, the context matching module is further configured to process another prompt for refining the CPR.

For example, FIG. 3 further illustrates an example flow for applying retrieval-augmented generation (RAG) associated with generating an assessment and plan by the A&P module 300. The RAG module 140 can be configured to receive the output of process 326 and to perform embedding matching with a physician-validated context library. In some cases, the physician-validated context library is generated by expert clinicians or physicians who analyze and validate data associated the CPR. In some cases, the data is provided, received, or generated in the form of panels, topics, and variants described herein elsewhere. In some cases, the output of RAG module 140 can be iteratively provided or transmitted to process 322 to update or refine the context matching 120. In some embodiments, the RAG module is further configured to use one or more prompts to improve processing of the context match and the one or more relevant context topics, and wherein the one or more prompts comprises chain-of-thought prompt engineering. In some embodiments, the RAG module is further configured to use N-shot learning to improve processing of the context match and the one or more relevant context topics, and wherein the N-shot learning comprises at least one learning example.

In some cases, process 142 of the RAG module 140 can include processes for receiving context topics from process 326 of the A&P module 300. In some cases, process 144 of the RAG module 140 can include processes for embedded matching (e.g., via RAG) with the physician-validated context library. In some cases, the output of process 144 can include refined context topics. In some cases, process 146 of the RAG module 140 can include processes for providing or transmitting the refined context topics to process 322 of the A&P module 300. In some cases, process 120 of the A&P module 300 can then use the refined context topics to further refine the prompt engineering, the CPR, or the context topics.

In some cases, the refinement process of processes 142, 144, and 146 of the RAG module 140 can be iteratively performed a predetermined number of times until an improved, accurate, or reliable answer is provided when generating user outputs 130. In some cases, the number of iterations is at least about 1, 10, 100, 1000, 10000, or more iterations, including increments therein. In some cases, the number of iterations is at most about 10000, 1000, 100, 10, or less iterations, including increments therein. In some cases, an accurate answer is at least about 60%, 70%, 80%, 90%, or more accurate, including increments therein. In some cases, the user (e.g., a clinician) may determine the number of iterations based on the reliability of the answers provided by the platform herein, e.g., reliability of the A&P. In some cases, the reliability may be based on a confidence of the user in the answer. In some cases, the answer is provided with a confidence of at least about
60%, 70%, 80%, 90%, or more, including increments therein.

Generating and Communicating User Outputs

In some embodiments, the platform comprises an output generation module configured to use the second LLM to process (1) the CPR, (2) the context based on the physician-validated schemas or clinical guidelines, and (3) one or more targeted prompts, to generate a second output comprising at least one of a differential diagnosis, an assessment of a health condition, or a treatment plan for the health condition.

For example, FIG. 3 further illustrates an example flow for generating user outputs 130 associated with generating an assessment and plan by the A&P module 300. The A&P module 300 can be configured to generate high-quality, high-fidelity, clear, and tailored output for the user, e.g., a clinician or patient. In some cases, the A&P module 300 can be configured to combine user input, relevant contexts, and specialized meta-prompts with prompt engineering to generate optimal outputs for the user. In some cases, the A&P module 300 can improve the accuracy or confidence of the A&P by at least about 5%, 10%, 15%, 20%, or more, including increments therein, compared to a LLM that does not use RAG. For example, process 130 of the A&P module 300 can be configured to use the CPR or refined CPR, prompt engineering, refined context topics, and a base LLM 334 (e.g., ChatGPT™). In some cases, the base LLM 324 is different than the base LLM 334. In some cases, the base LLM 324 is the same as the base LLM 334. In some cases, the base LLM 324 is updated, e.g., by processes performed by the RAG module 140, to generate the base LLM 334.

In some cases, process 130 of the A&P module 300 can be configured to receive the outputs of process 148 of the RAG module 140. In some cases, process 332 of the A&P module 300 can include processes for refining the CPR, refining contexts comprising physician-validated clinical guidelines, or refining engineering prompts. In some cases, process 130 of the A&P module 300 can include process 334 for providing the CPR or refined CPR, the results from the prompt engineering, or the refined context topics to a base LLM. In some cases, process 130 of the A&P module 300 can include process 334 for using the base LLM to process the CPR or refined CPR, the results from the prompt engineering, or the refined context topics to generate user outputs 336. In some cases, process 130 can include process 336 for transmitting the output of the base LLM. In some cases, the output of process 336 can include an answer, e.g., the assessment and plan for treatment. In some cases, a user (e.g., a clinician) may apply the assessment and plan when a confidence in the assessment and plan is at least about 60%, 70%, 8(0%, 90%, or more, including increments therein. In some cases, applying the assessment and plan can include providing the assessment and plan to the patient. In some cases, applying the assessment and plan can include providing the assessment and plan to the DDx module 200, the consult module 400, the AI-copilot module, or the AI-notebook module.

For example, FIG. 3 further illustrates communicating user outputs 150. In some cases, the user outputs 150 associated with the A&P module 300 may be provided to or received by the AI-copilot module or the AI-notebook module described herein elsewhere. In some cases, data or information associated with the AI-copilot module or the AI-notebook module may be provided as inputs for inputs 110 associated with the A&P module 300. In some cases, user outputs 150 are communicated to or displayed by a graphical user interface (GUI) or device as illustrated in FIG. 9B. In some cases, the GUI or device comprises the AI-copilot module or the AI-notebook module. In some cases, the user outputs 150 can be accessed or purchased through a virtual store described herein elsewhere.

FIG. 9B illustrates an example GUI or device configured to communicate the user outputs 150 associated with the A&P module 300. For example, the user outputs 150 may be communicated through the GUI or device by text, speech, or video. In some cases, the user outputs 150 may be communicated by text in the form of a report. In some cases, the GUI or device can provide functions for causing systems and methods herein to invoke sharing or archiving of the user outputs 150. In some cases, the user outputs 150 can be shared with the user, e.g., the clinical or the patient. In some cases, the user outputs 150 can be shared with the AI-copilot module or the AI-notebook module described herein elsewhere. In some cases, the user outputs may be shared with or transmitted to the DDx module 200 or the consult module 400.

FIGS. 11A-11D illustrates an alternative example detailed platform or system architecture for performing methods herein associated with generating an assessment and plan (A&P) by the A&P module, in accordance with some embodiments.

Systems and methods for generating clinical references by the Consult Module

In another aspect, disclosed herein is an artificial intelligence (AI)-based clinical decision support platform. In some embodiments, the platform comprises a user input processing module configured to receive at least a clinical reference question (CRQ) based at least in part on an input provided by a user. In some embodiments, the platform comprises a context matching module configured to (1) process a prompt for refining and understanding at least the CRQ and identify a suitable context, (2) provide at least the CRQ along with one or more relevant context topics to a first large language model (LLM), and (3) use the first LLM to generate a first output comprising a preliminary clinical diagnosis and a context match relating to a clinical problem representation (CPR). In some embodiments, the platform comprises a retrieval-augmented generation (RAG) module configured to process the context match and the one or more relevant context topics from the context matching module using a physician-validated context library, to determine a context topic based on physician-validated clinical guidelines for pushing into a second LLM. In some embodiments, the platform comprises an output generation module configured to use the second LLM to process (1) the CPR, (2) the context based on the physician-validated clinical guidelines, and (3) one or more targeted prompts for answering the CRQ, to generate a second output comprising of an answer to the CRQ, wherein the answer is provided to the user through a chatbot interface.

In some cases, the language learning model (LLM) disclosed herein can include a consult module 400, e.g., clinical reference module. In some cases, the consult module 400 can be configured as a clinical reference chatbot. For example, clinicians can use the chatbot to received improved answers to clinical reference questions. In some cases, the chatbot can use context data or information (e.g., the data or information the LLM uses to answer the question) that can be created, peer-reviewed, and validated for being up-to-date. For example, the model can be trained to reflect accepted evidence-based standard of care. In some cases, the consult module 400 can use an AI architecture that includes prompts that mimic the thought processes of a master clinician. In some cases, the consult module 400 can be trained by using a context library of physician-validated clinical guidelines. In some cases, the consult module 400 can be validated using the US Medical Licensing Examination (USMLE).

For example, recognized herein is that the USMLE is a cornerstone for evaluating the preparedness of physicians to actively care for patients by rigorously testing medical knowledge among the domains of adult medicine, pediatrics, neurology, surgery, biostatistics, and ethics. The exam can be taken in three stages (e.g., Step 1, Step 2, and Step 3), with the first two stages taken during medical school and the third taken typically after the first year of residency. Other LLMs have used the USMLE Steps to benchmark content knowledge for medical use cases. In some cases, the consult module 400 can be trained and validated using the USMLE Step 1-3 questions from the USMLE or the MedQ® dataset of approximately 10,000 USMLE questions. The outputs of the consult module 400 can be validated based on at least: accuracy (e.g., Did the consult module get the right answer choice?) and consistency (e.g., Did the consult module consistently get the right answer choice?). In some cases, the consult module 400 be implemented using retrieval-augmented generation (RAG) to improve the outputs of the consult module 400. For example, the RAG can include physician-written contexts. In some cases, the improved performance of the consult module 400 with RAG can be compared to the performance of the consult module 400 without RAG. In some cases, the improved performance of the consult module 400 (with or without RAG) can be determined by comparison to other base LLMs, e.g., GPT-4 by OpenAI® or MedLM® by Google®, on the same dataset. For example, Table 1 depicts the performance of the LLM herein, e.g., the consult module 400, as applied to the 2023 USMLE Step 1, Step 2, Step 3 Practice Tests.

TABLE 1

| Performance | Consult Module |
|---|---|
| Average Across Exams | 90.5% |
| USMLE Step 1 | 95.4% |
| USMLE Step 2 | 88.8% |
| USMLE Step 3 | 87.2% |

In some cases, the language learning model (LLM) disclosed herein can include a consult module 400, e.g., clinical reference module. In some cases, the consult module 400 can be configured to answer specific clinical reference questions. For example, recognized herein is that contemporary clinical support tools that clinicians most commonly use fall in the line of clinical reference tools. These tools can include online repositories such as UpToDate® by Wolters Kluwer, medical calculators such as MDCalc®, and reference textbooks such as the MGH WhiteBook® or Harrison's Textbook on Internal Medicine©. Physicians can utilize these reference tools to help answer specific clinical questions regarding etiology, presentation, diagnostic workup, or management of presenting pathologies of patients. In some cases, the consult module 400 can be trained and validated using a large database of clinical reference questions typically asked about the top 200 most common pathologies. In some cases, the consult module 400 be implemented using retrieval-augmented generation (RAG) to improve the outputs of the consult module 400. In some cases, the improved performance of the consult module 400 with RAG can compared to the performance of the consult module 400 without RAG. In some cases, the outputs of the consult module 400 can be validated based at least on scoring by expert physicians and scored on a 4-axis domain: 1, factuality (e.g., Is the answer factually correct?); 2, completeness (e.g., Is the answer complete? Are components missing?Did the module go into enough detail?); 3, harm ratio (e.g., Could the answer potentially cause harm to a patient?); and 4. reasoning (e.g., Is the reasoning of the response sound?).

Figure 4:
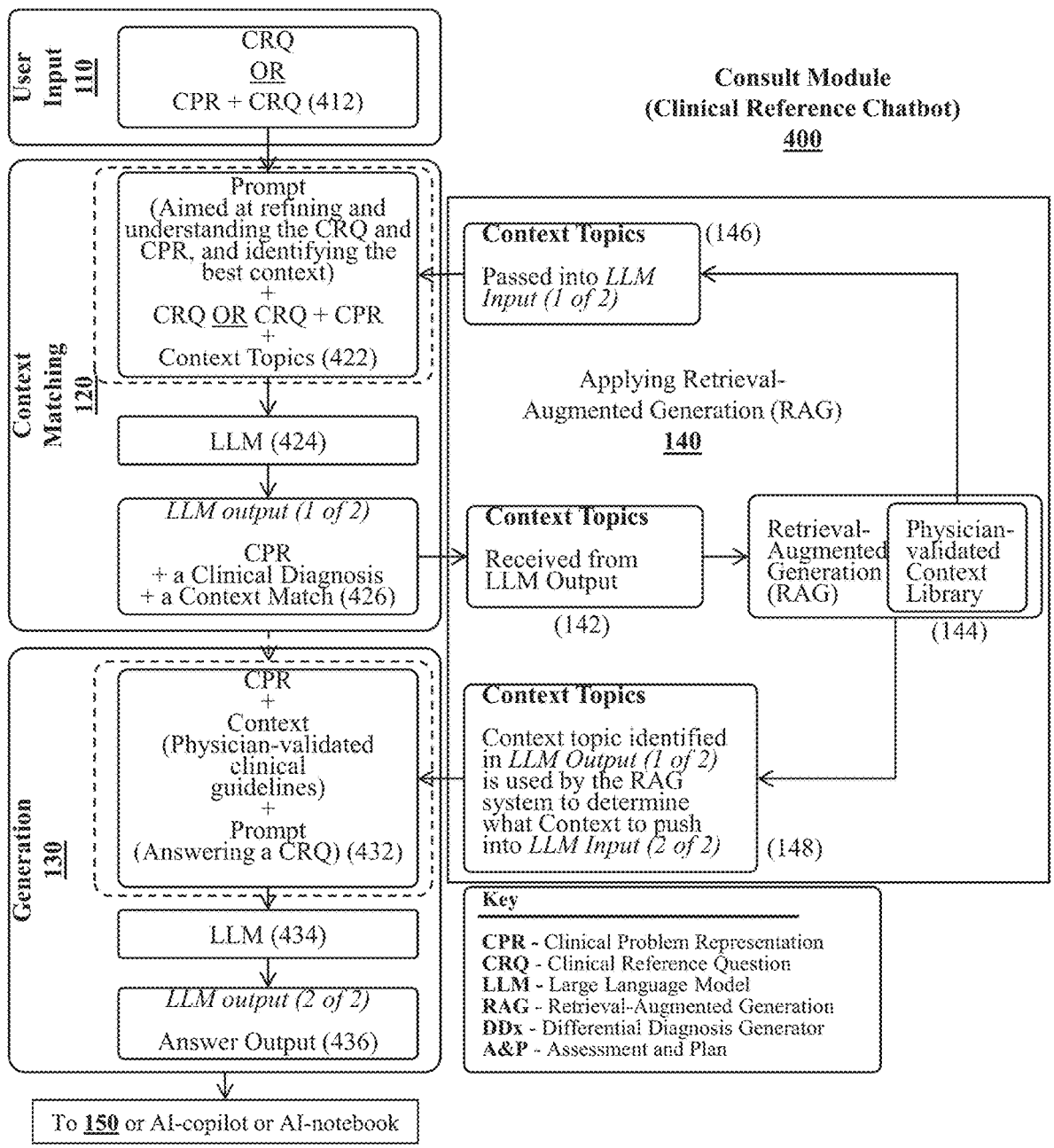
FIG. 4 illustrates an example detailed platform or system architecture for performing methods herein associated with generating a consult or clinical reference by the consult module, in accordance with some embodiments. The consult module can include processes for receiving user inputs, performing context matching, applying retrieval-augmented generation (RAG) in a feedback loop, generating user outputs, and communicating user outputs.

FIG. 4 illustrates an example detailed system architecture for performing methods herein associated with generating a consult or clinical reference (clinical reference) by the consult module 400. The consult module 400 may be configured to use the same or similar LLM system architectures illustrated in FIGS. 1A-1B but which is further configured to provide the specific functionality of the consult module 400.

Receiving User Inputs

In some embodiments, the platform comprises a user input processing module configured to receive at least a clinical reference question (CRQ) based at least in part on an input provided by a user.

For example, FIG. 4 illustrates an example flow for receiving or generating user inputs 110 associated with generating a consult or clinical reference by the consult module 400. The consult module 400 can enable users (e.g., clinicians or patients) to provide improved specific and complete inputs for questions they need answered. In some cases, the inputs 412 can be associated with a clinical problem representation (CPR). For example, a user (e.g., a clinician) may provide as user inputs 110 to the consult module 400 that, "the patient is a 65 year old woman with a history diabetes and hyperlipidemia presenting with acute-onset chest pain and diaphoresis found to have hyperacute T-waves without ST elevation." The consult module 400 can process the user inputs 110 to automatically generate a consult or clinical reference. In some embodiments, the user input processing module is further configured to generate the CPR. The CPR may be associated with a patient presenting to a clinician with a healthcare issue. In some cases, the inputs 412 can be associated with one or more clinical reference questions (CRQ). The healthcare issue may be associated with panels, topics, and variants. Panels can include, for example, the specific areas of healthcare, e.g., radiology for a patient seeking breast care. Topics can include, for example, specific diseases that fall under each panel, e.g., a patient with breast cancer. Variants can include, for example, presentations within each topic, e.g., age of the patient with breast cancer. In some cases, the inputs 412 can be associated with a CPR and a one or more focused questions. For example, the one or more focused questions can be provided by the clinician or the patient and answered or determined by chatbot herein to further improve the outputs of the consult module 400. In some cases, the inputs 412 can be associated with a CPR and a one or more CRQs. For example, the one or more CRQs can be provided by the clinician or the patient and answered or determined by chatbot herein to further improve the outputs of the consult module 400.

FIG. 9A illustrates receiving or generating user inputs 110 associated with the consult module 40. In some cases, the user inputs 110 are received through a graphical user interface (GUI) or device as illustrated in FIG. 9A. In some cases, a user (e.g., a clinician or a patient) can communicate the user inputs 110 to the GUI or device. In some cases, the user can communicate the user inputs 110 by text, speech, or video. In some cases, the user inputs 110 associated with the consult module 400 may be received from or provided by the AI-copilot module or the AI-notebook module described herein elsewhere. In some cases, data or information associated with the AI-copilot module or the AI-notebook module may be received as inputs for inputs 110 associated with the consult module 400. In some cases, the GUI or device comprises the AI-copilot module or the AI-notebook module.

FIG. 9A further illustrates an example prompt associated with the CPR or CRQ. In some cases, the prompt may instruct the user to provide specific data associated with the CPR or CRQ. For example, the prompt may instruct the user to include: age, relevant past medical history, medications, presenting symptoms, associated symptoms, descriptions of relevant studies (e.g., labs and imaging), the illness course, and any additional information a user might include when consulting another user, e.g., a clinician or physician. The GUI or device can provide functions for causing systems and methods herein to invoke execution of the DDx module 200, the A&P module 300, or the consult module 400.

FIG. 9B illustrates an example GUI or device configured to communicate the user outputs 150 associated with the consult module 400. For example, the user outputs 150 may be communicated through the GUI or device by text, speech, or video. In some cases, the user outputs 150 may be communicated by text in the form of a report. In some cases, the GUI or device can provide functions for causing systems and methods herein to invoke sharing or archiving of the user outputs 150. In some cases, the user outputs 150 can be shared with the user, e.g., the clinical or the patient. In some cases, the user outputs 150 can be shared with the AI-copilot module or the AI-notebook module described herein elsewhere. In some cases, the user outputs may be shared with or transmitted to the DDx module 200 or the A&P module 300.

Performing Context Matching from User Inputs

In some embodiments, the platform comprises a context matching module configured to (1) process a prompt for refining and understanding at least the CRQ and identify a suitable context, (2) provide at least the CRQ along with one or more relevant context topics to a first large language model (LLM), and (3) use the first LLM to generate a first output comprising a preliminary clinical diagnosis and a context match relating to a clinical problem representation (CPR)

For example, FIG. 4 further illustrates an example flow for performing context matching 120 associated with generating a consult by the consult module 400. The consult module 400 can be configured to use prompt engineering, the CPR, the CRQ, context topics, and a base LLM (e.g., ChatGPT™) to perform context matching 120 from user inputs 110 and to optimize embedding for the RAG module 140.

In some cases, process 120 of the consult module 400 can include process 422 for using prompt engineering to refine and understand the CPR and CRQ and for generating the improved, best, or optimal context. In some cases, process 120 of the consult module 400 can include process 424 for providing the CPR or CRQ or refined CPR or CRQ, the results from the prompt engineering, and the context topics to a base LLM. In some cases, process 120 of the consult module 400 can include process 424 for using the base LLM to process the CPR or CRQ or refined CPR or CRQ, the results from the prompt engineering, and the context topics to further extract meaning from the user inputs 110. In some cases, process 120 of the consult module 400 can include process 426 for transmitting the output of the base LLM to the RAG module 140 for iteratively applying RAG. Alternatively, process 426 can transmit the output of the base LLM directly to process 130 of the consult module 400, e.g., the RAG module 140 can be bypassed. In some cases, the output of process 426 can include the CPR and CRQ or refined CPR and CRQ, a clinical diagnosis, or one or more context matches. In some cases, the output of process 426 can include context topics determined by the base LLM for transmittal to the RAG module 140.

Applying Retrieval-Augmented Generation (RAG) for Context Matching

In some embodiments, the platform comprises a retrieval-augmented generation (RAG) module configured to process the context match and the one or more relevant context topics from the context matching module using a physician-validated context library, to determine a context topic based on physician-validated clinical guidelines for pushing into a second LLM. In some embodiments, the context matching module is further configured to provide the CRQ and the CPR to the first LLM For example. FIG. 4 further illustrates an example flow for applying retrieval-augmented generation (RAG) associated with generating a consult or clinical reference by the consult module 400. The RAG module 140 can be configured to receive the output of process 426 and to perform embedding matching with a physician-validated context library. In some cases, the physician-validated context library is generated by expert clinicians or physicians who analyze and validate data associated the CPR. In some cases, the data is provided, received, or generated in the form of panels, topics, and variants described herein elsewhere. In some cases, the output of RAG module 140 can be iteratively provided or transmitted to process 422 to update or refine the context matching 120. In some embodiments, the RAG module is further configured to use one or more prompts to improve processing of the context match and the one or more relevant context topics, and wherein the one or more prompts comprises chain-of-thought prompt engineering. In some embodiments, the RAG module is further configured to use N-shot learning to improve processing of the context match and the one or more relevant context topics, and wherein the N-shot learning comprises at least one learning example.

In some cases, process 142 of the RAG module 140 can include processes for receiving context topics from process 426 of the consult module 400. In some cases, process 144 of the RAG module 140 can include processes for embedded matching (e.g., via RAG) with the physician-validated context library. In some cases, the output of process 144 can include refined context topics. In some cases, process 146 of the RAG module 140 can include processes for providing or transmitting the refined context topics to process 422 of the consult module 400. In some cases, process 120 of the consult module 400 can then use the refined context topics to further refine the prompt engineering, the CPR, or the context topics.

In some cases, the refinement process of processes 142, 144, and 146 of the RAG module 140 can be iteratively performed a predetermined number of times until an improved, accurate, or reliable answer is provided when generating user outputs 130. In some cases, the number of iterations is at least about 1, 10, 100, 1000, 10000, or more iterations, including increments therein. In some cases, the number of iterations is at most about 10000, 1000, 100, 10, or less iterations, including increments therein. In some cases, an accurate answer is at least about 60%, 70%, 80%, 90%, or more accurate, including increments therein. In some cases, the user (e.g., a clinician) may determine the number of iterations based on the reliability of the answers provided by the platform herein. e.g., reliability of the clinical reference. In some cases, the reliability may be based on a confidence of the user in the answer. In some cases, the answer is provided with a confidence of at least about 60%, 70%, 80%, 90%, or more, including increments therein.

Generating and communicating User Outputs

In some embodiments, the platform comprises an output generation module configured to use the second LLM to process (1) the CPR, (2) the context based on the physician-validated clinical guidelines, and (3) one or more targeted prompts for answering the CRQ, to generate a second output comprising of an answer to the CRQ, wherein the answer is provided to the user through a chatbot interface.

For example, FIG. 4 further illustrates an example flow for generating outputs associated with generating a consult or clinical reference by the consult module 400. The consult module 400 can be configured to generate high-quality, high-fidelity, clear, and tailored output for the user, e.g., a clinician or patient. In some cases, the consult module 400 can be configured to combine user inputs, relevant context topics, and specialized meta-prompts with prompt engineering to generate optimal outputs for the user. In some cases, the consult module 400 can improve the accuracy or confidence of the clinical reference by at least about 5%, 10%, 15%, 20%, or more, including increments therein, compared to a LLM that does not use RAG. For example, process 130 of the consult module 400 can be configured to use the CPR or CRQ or refined CPR or CRQ, prompt engineering, refined context topics, and a base LLM 434 (e.g., ChatGPT™). In some cases, the base LLM 424 is different than the base LLM 434. In some cases, the base LLM 424 is the same as the base LLM 434. In some cases, the base LLM 424 is updated, e.g., by processes performed by the RAG module 140, to generate the base LLM 434.

In some cases, process 130 of the consult module 400 can be configured to receive the outputs of process 148 of the RAG module 140. In some cases, process 432 of the consult module 400 can include processes for refining the CPR, refining contexts comprising physician-validated clinical guidelines, or refining engineering prompts. In some cases, process 130 of the consult module 400 can include process 434 for providing the CPR or CRQ or refined CPR or CRQ, the results from the prompt engineering, or the refined context topics to a base LLM. In some cases, process 130 of the consult module 400 can include process 434 for using the base LLM to process the CPR or CRQ or refined CPR or CRQ, the results from the prompt engineering, or the refined context topics to generate user outputs 436. In some cases, process 130 can include process 436 for transmitting the output of the base LLM. In some cases, the output of process 436 can include an answer, e.g., an answer to a clinical reference question. In some cases, a user (e.g., a clinician) may apply the answer to a clinical reference question when a confidence in the answer is at least about 60%, 70%, 80%, 90%, or more, including increments therein. In some cases, applying the answer to a clinical reference question can include providing the answer to the patient. In some cases, applying the answer to a clinical reference question can include providing the answer to the DDx module 200, the A&P module 300, the AI-copilot module, or the AI-notebook module.

For example, FIG. 4 further illustrates communicating user outputs 150. In some cases, the user outputs 150 associated with the consult module 400 may be provided to or received by the AI-copilot module or the AI-notebook module described herein elsewhere. In some cases, data or information associated with the AI-copilot module or the AI-notebook module may be provided as inputs for inputs 110 associated with the consult module 400. In some cases, user outputs 150 are communicated to or displayed by a graphical user interface (GUI) or device as illustrated in FIG. 9B. In some cases, the GUI or device comprises the AI-copilot module or the AI-notebook module. In some cases, the user outputs 150 can be accessed or purchased through a virtual store described herein elsewhere.

FIGS. 12A-12D illustrate an alternative example detailed platform or system architecture for performing methods herein associated with generating a consult or clinical reference by the consult module, in accordance with some embodiments.

Systems and Methods for the AI-Copilot Module

In some embodiments, the platform further comprises an AI-copilot module configured to generate data for a pre-visit clinical decision. In some embodiments, the data is received by the user input processing module to further assist the platform in generating the differential diagnosis, the assessment of a health condition, or the treatment plan for the health condition. In some embodiments, the platform further comprises an AI-copilot module configured to generate data for a pre-visit clinical decision. In some embodiments, the data is received by the user input processing module to further assist the platform in generating the answer to the CRQ. In some cases, the AI-copilot module can be separate from the platform herein but can be configured to operatively use the same or similar AI-architecture or LLM herein to receive data and generate outputs. In some cases, the AI-copilot module can be integrated into the platform herein and can be configured to operatively use the same or similar AI-architecture or LLM herein to receive data and generate outputs.

In some cases, the language learning model (LLM) disclosed herein can include an AI-powered note-writer and assistant module for the patient encounter, which may be referred to as the AI-copilot module. The AI-copilot module can be configured as an electronic health record (EHR) that is integrated and enabled for speech-to-text and text-to-speech. In some cases, the speech may be a recorded speech of a clinician or a patient or a recorded speech between the clinician and the patient. In some cases, the speech may be a recorded video of a clinician or a patient or a recorded video between the clinician and the patient. In some cases, the AI-copilot module can be configured to process and transcribe the recorded speech or the recorded video into text. The LLM herein can use the processed or transcribed speech for performing functions or operations by the DDx module 200, the A&P module 300, the consult module 400, or the AI-notebook module. In some cases, the AI-copilot module can reside in and be accessible through a patient's EHR. The AI-copilot module can be configured to provide pre-visit clinical decision support. Pre-visit clinical decision support can include a differential diagnosis by the DDx module 200 herein, suggested history questions, or suggested physical exam maneuvers for the clinician that are based on the LLM's analysis of the nursing triage note and vital signs. During the patient encounter, communications (e.g., speech, text, or video) between the clinician and the patient can be recorded and processed by the AI-copilot module. After the patient encounter, the AI-copilot module can generate or provide post-encounter clinical decision support. Post-encounter clinical decision support can include a revised differential diagnosis (e.g., by the DDx module 200) based on recorded communications of the clinician, the patient, or between the clinician and the patient. Post-encounter clinical decision support can include an assessment and plan (e.g., by the A&P module 300). The clinician can review and edit the outputs of the modules (e.g., drafts of the differential diagnosis or the assessment and plan) and create a full end-to-end completed note documentation for further editing and review. In some cases, the AI-copilot module can be configured to create a pre-encounter differential diagnosis for clinical decision support, provide a post-encounter updated differential diagnosis, and draft an assessment and plan.

Systems and Methods for the AI-Notebook Module

In some embodiments, the platform further comprises an AI-notebook module configured to generate data associated with clinical knowledge. In some embodiments, the data is received by the user input processing module to further assist the platform in generating the differential diagnosis, the assessment of a health condition, or the treatment plan for the health condition. In some embodiments, the data is received by the user input processing module to further assist the platform in generating the answer to the CRQ. In some cases, the AI-notebook module can be separate from the platform herein but can be configured to operatively use the same or similar AI-architecture or LLM herein to receive data and generate outputs. In some cases, the AI-notebook module can be integrated into the platform herein and can be configured to operatively use the same or similar AI-architecture or LLM herein to receive data and generate outputs.

In some cases, the language learning model (LLM) disclosed herein can include an AI-notebook module. For example, the AI-notebook module can be configured as a clinical knowledge management system and used by individuals (e.g., clinicians) or healthcare systems to build a database of knowledge for learning or practicing medicine. In some cases, the AI-notebook module can include specific note types that are tailored for individual clinicians. For example, the specific note types can include schemas, scripts, cases, and pearls, which can allow clinicians to easily organize new data or knowledge. In some cases, other modules associated with the LLM herein (e.g., the DDx module 200, the A&P module 300, the consult module 400, and the AI-copilot module) can access the AI-notebook module and use it as context to generate outputs of each module. In some cases, data associated with the AI-notebook module can also be used to further train the other modules associated with the LLM herein.

In some cases, the AI-notebook module can be configured to allow individual users to load their own context libraries or N-shot learning examples into the platform herein. In some cases, the platform herein can use the context libraries and N-shot learning examples to execute different functions or operations using the AI architecture herein.

Systems and Methods for the Virtual Store

In some cases, the language learning model (LLM) disclosed herein may be associated with a virtual store. For example, users associated with the LLM herein can access or purchase AI-notebook and AI-copilot modules and modules associated with the LLM herein or for use by the LLM herein. In some cases, users may develop user-specific AI-notebook and AI-copilot modules and user-specific modules that can be used with the LLM herein. The users may provide any module to the virtual store for access or purchase by other users. Other users can access or purchase the user-specific AI-notebook and AI-copilot modules and modules associated with the LLM herein through the virtual store.

In some cases, the virtual store can be configured to allow users who have built models using the platform herein to sell or to provide access to their models to other users. Users can be provided access to plug in or use the models in the platform herein.

EXAMPLES

While various examples of the present disclosure have been shown and described herein, such examples are provided by way of example only. Numerous variations, changes, or substitutions may occur without departing from the present disclosure. It should be understood that various alteratives to the examples described herein may be employed.

Example 1—Systems and Methods Herein for Radiologic Decision-Making

Abstract

Large language models (LLMs) have become useful in many applications. However, the potential usefulness of LLMs in medical applications remains a challenge. Systems and methods herein using retrieval-augmented generation (RAG) were investigated to characterize their performance in predicting the most appropriate imaging study for specific clinical presentations in various subspecialty areas in radiology.

For example, the performance of systems and methods herein were compared to other LLMs, e.g., ChatGPT™ (GPT-4) by Open AI®. Testing included 1075 clinical scenarios from 11 American College of Radiology (ACR) expert panels to predict the most appropriate imaging study. Testing was benchmarked against the ACR Appropriateness Criteria. Two responses per clinical presentation were generated and averaged for the final clinical presentation score. Clinical presentation scores for each topic area were averaged as its final score. The average of the topic scores within a panel determined the final score of each panel Responses were compared on a scale of 0 to 3. Partial scores were given for non-specific answers. Pearson correlation coefficient (R-value or r) was calculated for each panel to determine a context-specific performance.

Systems and methods herein, as depicted in Table 2, scored significantly better than ChatGPT™ (2.32+/−0.67 versus 2.08+/−0.74, p=0.002). Both performed the best in the Polvtrauma, Breast, and Vascular panels, and both performed the worst in the Neurologic. Musculoskeletal, and Cardiac panels. Systems and methods herein performed better than ChatGPT™ in 10 of 11 panels. Maximum agreement between systems and methods herein and ChatGPT™ occurred in the Pediatrics, Neurologic, and Thoracic panels. The most disagreement occurred in the Vascular, Breast, and Urologic panels.

This study demonstrates that systems and methods herein can be more useful to predict imaging studies by using RAG to incorporate medical-text training in training the LLM model. Such improvement can support the utility of systems and methods herein for at least radiologic decision-making.

INTRODUCTION

Artificial Intelligence (AI) has made significant strides to improve healthcare outcomes in areas such as neurology, pediatrics, and dermatology. However, use of AI in radiology is less developed. At the forefront of these technological advancements in AI are large language models (LLMs), which can be designed to comprehend and generate human-like text. Some LLMs such as OpenAI's® ChatGPT™ may be based on the Generated Pre-trained Transformer-4 (GPT-4). Such LLMs may be trained on general text extracted from a variety of sources and can be engineered to process and generate responses to prompts. Systems and methods herein can provide an improved LLM trained with specific data via RAG to improve healthcare outcomes. For example, the LLM provided herein can be initially based on the GPT-4 architecture. However, the LLM can be fine-tuned specifically on medical texts to generate and improve diagnoses and treatment plans based on clinical input. Imaging can play a critical role in modem medicine. Recommendation of an appropriate modality or a study can be important not only for accurate diagnosis but also to prevent unnecessary procedures and to limit waste of healthcare dollars.

Recognizing this importance, the American College of Radiology (ACR) created the Appropriateness Criteria in 1993, giving physicians a centralized resource to determine the appropriateness of an imaging test for a given clinical scenario. The selection of an imaging study to answer a diagnostic question may be largely based on a physician's judgment, experience, and clinical guidelines. However, these decisions can be complex and challenging, especially in complicated clinical scenarios. As such, referring physicians may rely on radiologists for guidance. Despite the availability of resources, such as including the ACR appropriateness criteria, inappropriate utilization of imaging studies may be common. AI may possess the potential to be an additional resource to provide referring physicians with a more accurate and appropriate imaging study recommendation. With new technological developments in LLMs and the importance of imaging selection, this study aimed to explore the ability of systems and methods herein versus ChatGPT™ to recommend the most appropriate diagnostic imaging study in comparison to the ACR Appropriateness Criteria for specific patients.

Methods

Artificial intelligence. ChatGPT-4 may be based on the transformer architecture, which has been shown to be effective in many natural language processing applications from text generation to classification. The transformer may utilize attention mechanisms to weigh the importance of different words in a sentence. This study utilized ChatGPT-4, the newest model developed by Open AI®. This model has surpassed the performance of all previous Open AI® models, including GPT-3.5, on a multitude of benchmarks and real-world examinations such as the Uniform Bar Exam (UBE), the Law School Admission Test (LSAT), and the Graduate Record Examinations (GRE). As with LLMs such as ChatGPT-4, ChatGPT-4's responses may result from its training data, which may not be specific or current. For example. ChatGPT-4 has a knowledge cutoff of September 2021, which can make its responses based on information only available up to that date. The LLM herein can be built on top of GPT-4 and be further trained on data that is specific and current, e.g., medical text data. Such data can include specific and recent evidence-based guidelines, schemas, and case studies. In some cases, such data can be created by expert clinicians.

ACR Appropriateness Criteria. In this study, the American College of Radiology (ACR) Appropriateness Criteria ("Criteria") served as the benchmark for AI outputs, e.g., responses associated with healthcare treatment. The Criteria can serve as a guide for clinicians in choosing the best imaging study for a particular clinical scenario. The guidelines are updated regularly to reflect the latest developments in research, imaging technology, and field consensus. The Criteria are organized by panel, then by topic, and further subdivided into variants. Panels can include the area of radiology, e.g., breast, musculoskeletal (MSK), or thoracic. Topics can include the diseases that fall under each panel. Variants can include the presentations within each topic. The Criteria, accessed May 3, 2023, incorporate the benefits and risks of each imaging study and are classified into three groups: "Usually Appropriate." "May Be Appropriate," or "Usually Not Appropriate."

Input and Scoring. In some cases, the input and scoring strategy were adapted and modified from a previous study. See Nazario-Johnson et al, "Use of large language models to predict neuroimaging." *Journal of the American College of Radiology* 20.10 (2023): 1004-1009, which is incorporated herein by reference in its entirety. The prompts to the LLMs were created from the variant titles of the Criteria and were based on a case scenario involving a 65-year-old patient. These prompts were inputted directly into the LLM herein. The phrase "Rank the top three most appropriate radiologic imaging modalities" was added to the ChatGPT™ input. For any variant that specified age, that age was added to the prompt. Each prompt was inputted two times before being subsequently scored. If the output was not specific, the lower bound score was accepted with a penalty of 0.5. Clinical presentation scores for each topic area were averaged as the score for the specific topic. The average of the topic scores within a panel determined the final score of each panel.

Statistical Analysis. The different LLMs were first compared using the final score per panel. The Applicant utilized a Wilcoxon signed rank test to compare the performance of each LLM. Calculations were performed using Scipy. For the per-panel comparisons, a Bonferroni correction was used, making a p-value <0.005 statistically significant. To account for the high variance of the data, the Applicant further calculated Pearson's R Correlation Coefficient (R-value) for score between ChatGPT™ and the LLM herein across the topics for a given panel. These are plotted along with a line of best fit. An R-value closer to 1 indicates that the performance of ChatGPT™ and the LLM herein was similar across topics. An R-value closer to 0 indicates that one of the AIs deviated from the other. Pearson's correlation was calculated using Scipy, and figures were generated using Matplotlib by MATLAB®.

Results

Figure 5:
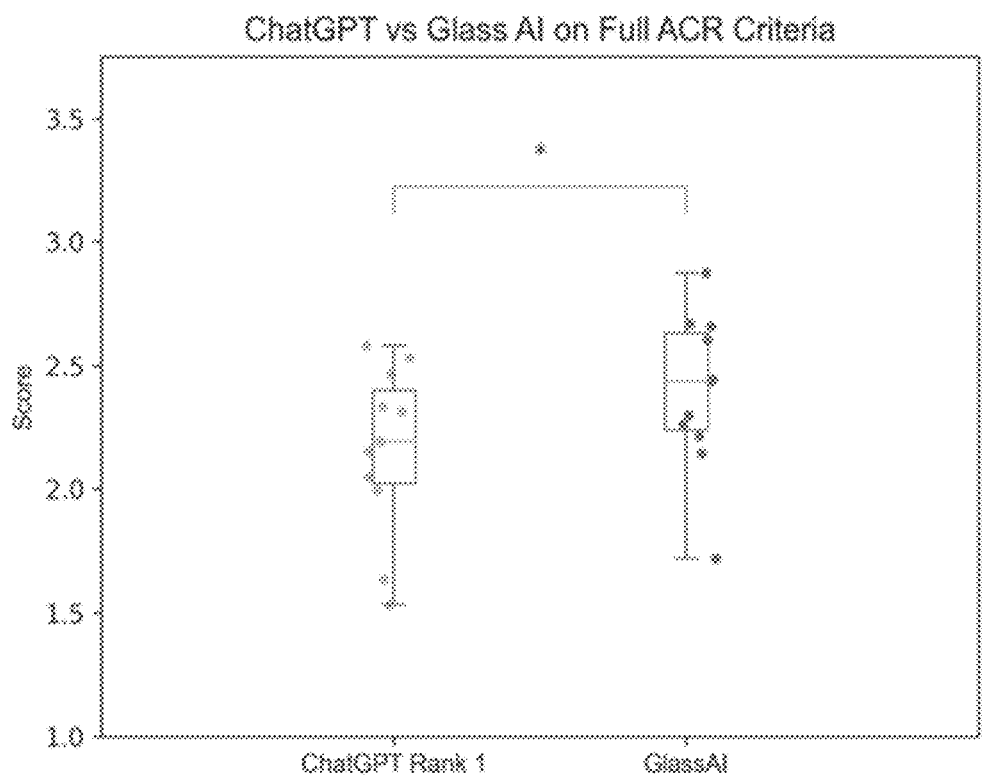
FIG. 5 illustrates an example distribution of American College of Radiology (ACR) scores for systems and methods herein versus other large language models (LLMs) such as ChatGPT™, in accordance with some embodiments. The difference between the two distributions can be statistically significant.

Performance of LLMs. FIG. 5 illustrates that ChatGPT™ and the LLM herein are both able to predict the most appropriate imaging study given a specific patient presentation. With a maximal score of 3, the mean score across all panels for ChatGPT™ and the LLM herein is 2.08+/−0.73 and 2.32+/−0.67, respectively. For both LLMs, their highest-performance panels were polytrauma, breast, and vascular. On the other hand, their worst-performance panels were neurologic, musculoskeletal (MSK), and cardiac.

Figure 6:
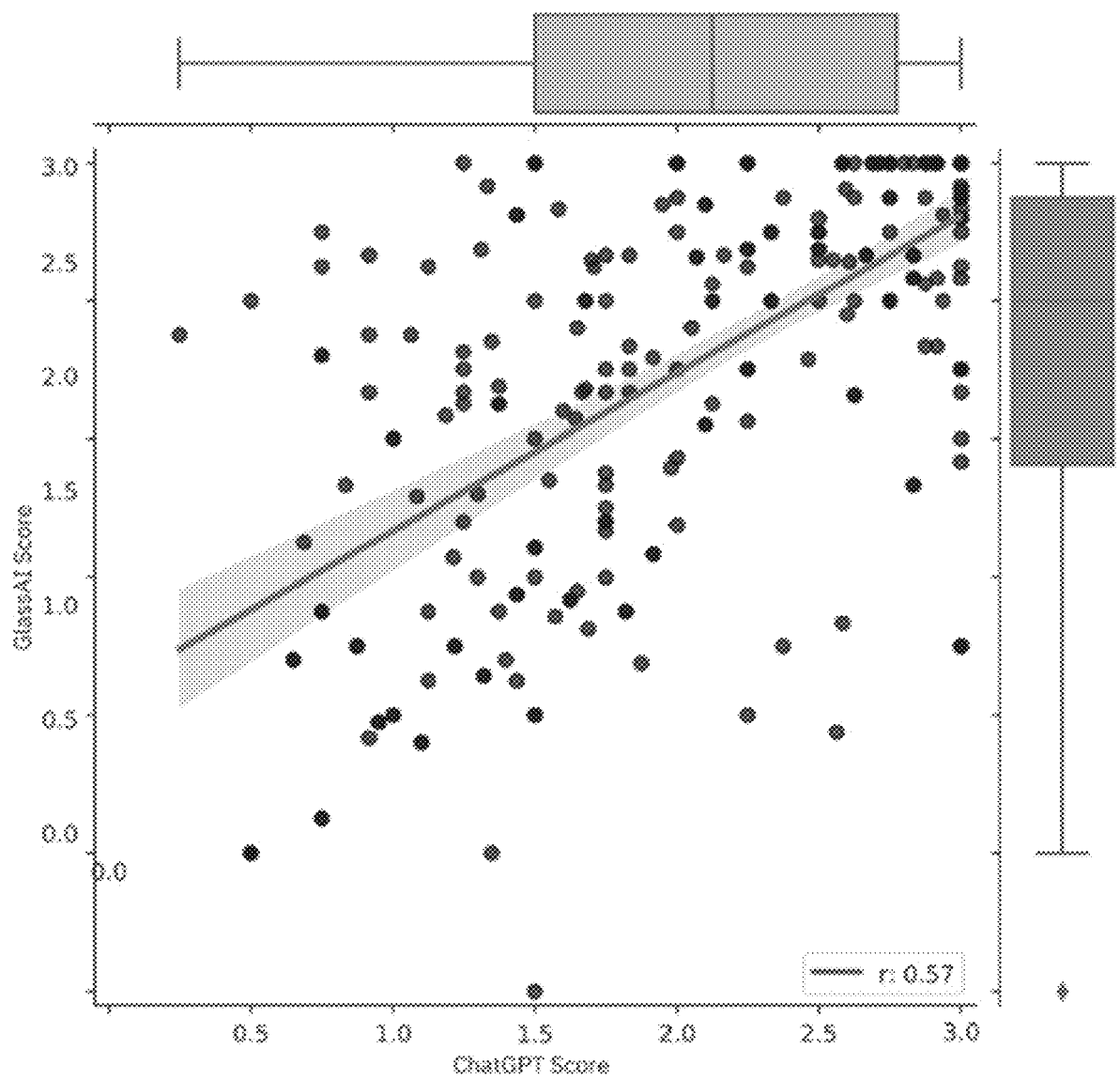
FIG. 6 illustrates an example correlation between systems and methods herein versus other large language models (LLMs) such as ChatGPT™, in accordance with some embodiments. Each point represents a panel in the appropriateness criteria. An R-value (or "r" as depicted) of 0.57 shows a moderate positive agreement between the AIs indicating a discrepancy in the performance.
Figure 7:
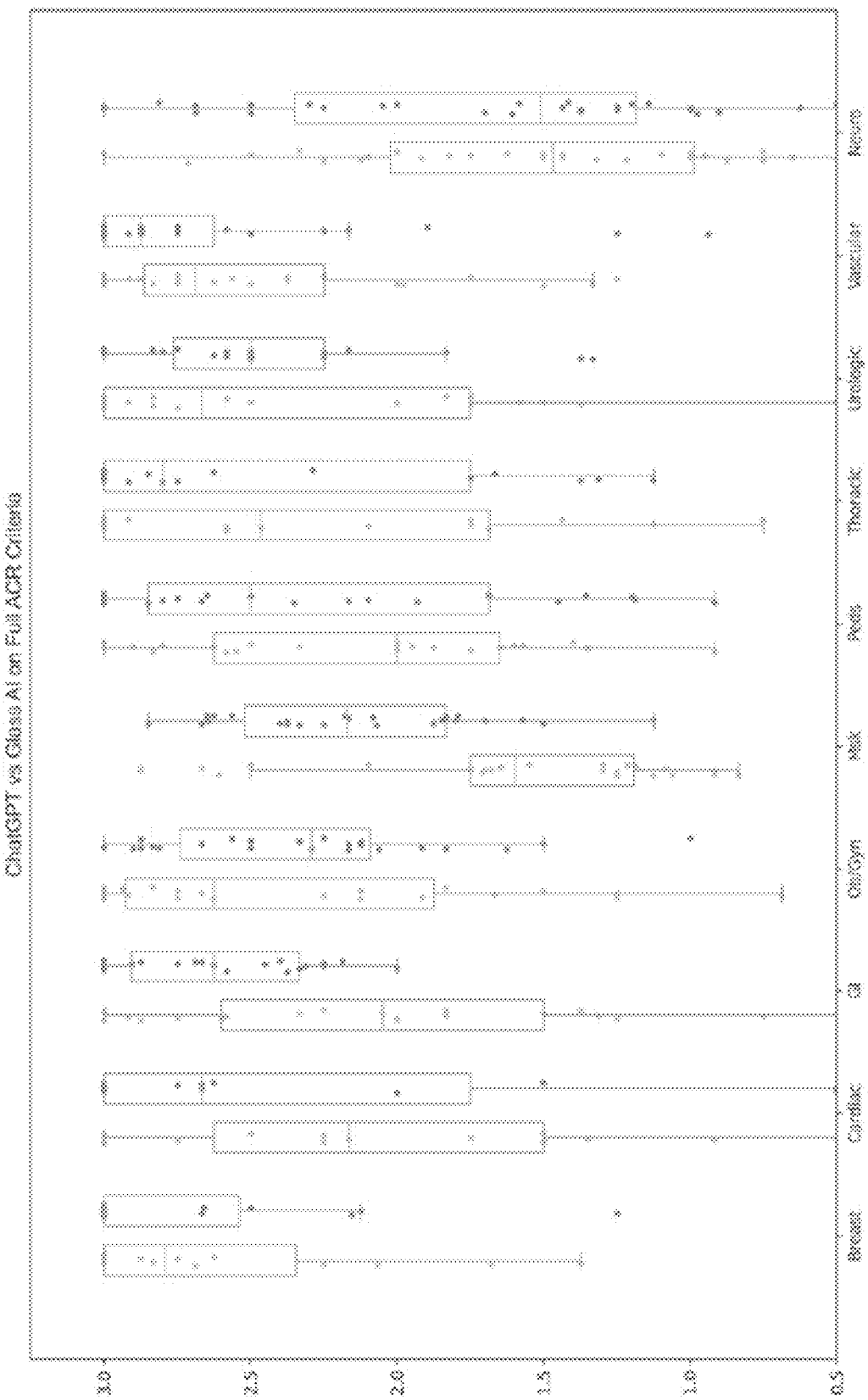
FIG. 7 illustrates an example comparison of the distributions for each panel in the criteria between systems and methods herein versus other large language models (LLMs) such as ChatGPT™, in accordance with some embodiments. Each point represents a panel in a specific topic.
Figure 8A:
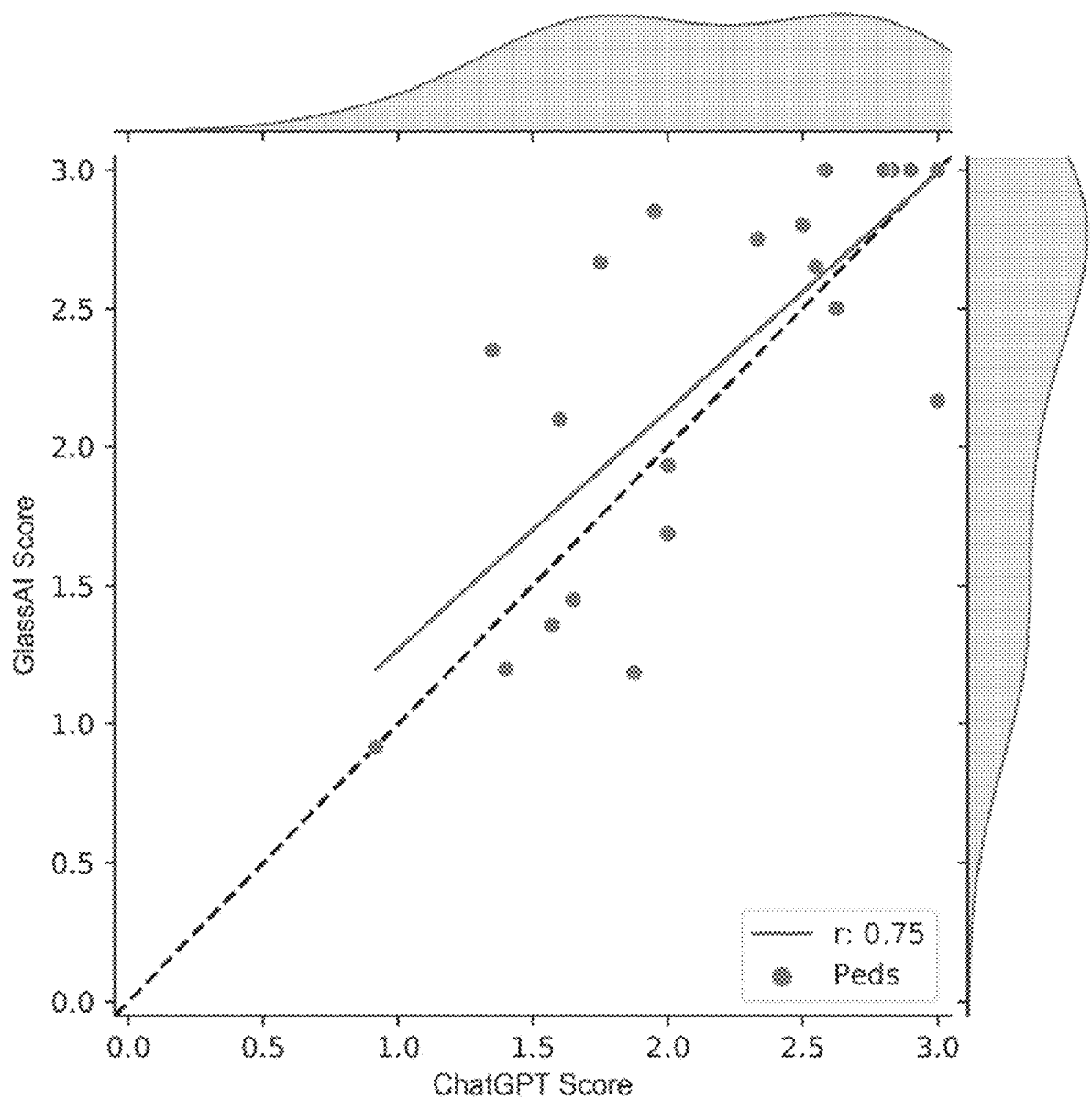
FIGS. 8A-8H illustrate example improvements of systems and methods herein in different radiologic settings over other large language models (LLMs) such as ChatGPT™, in accordance with some embodiments.
Figure 8B:
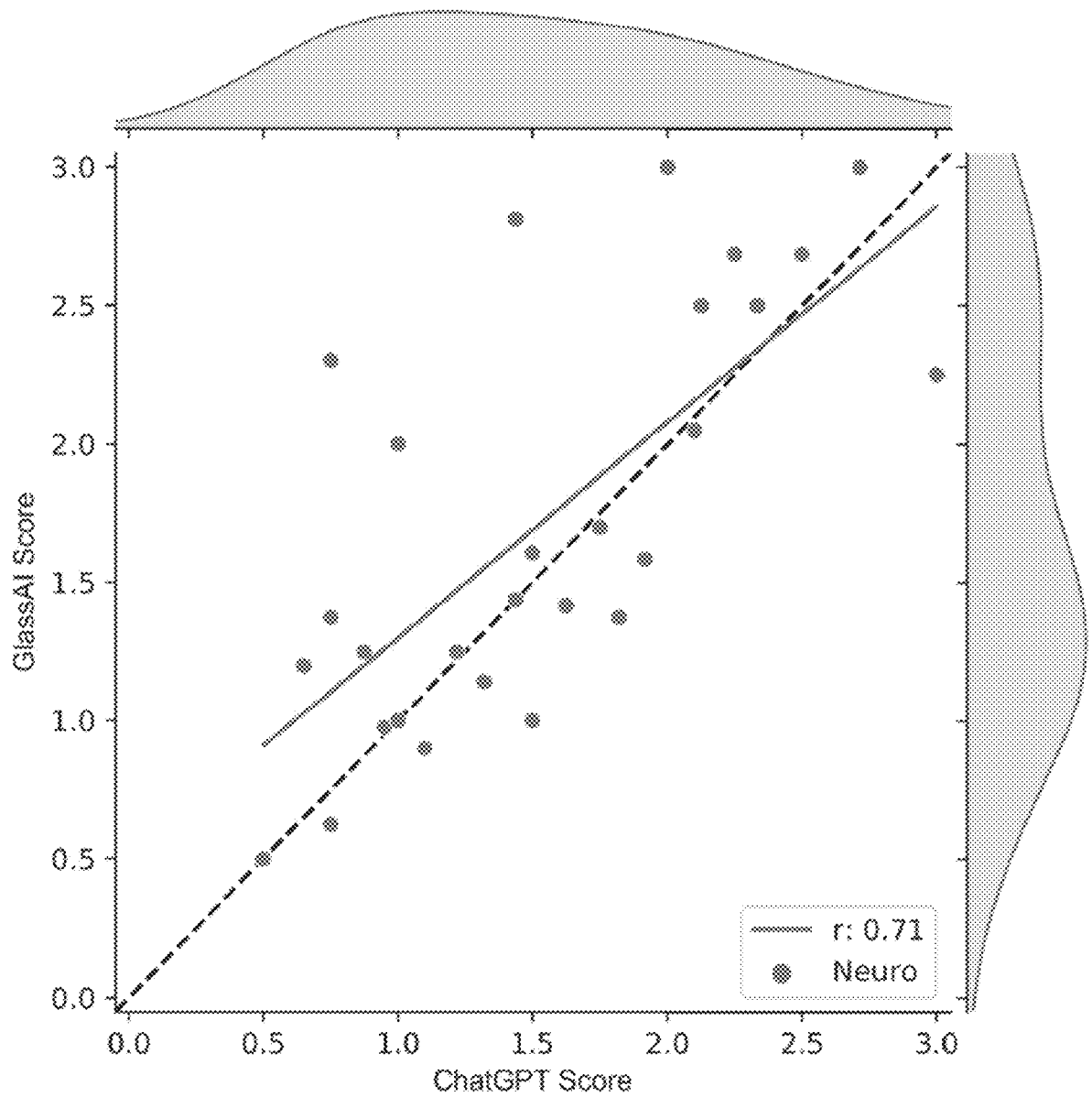
Figure 8C:
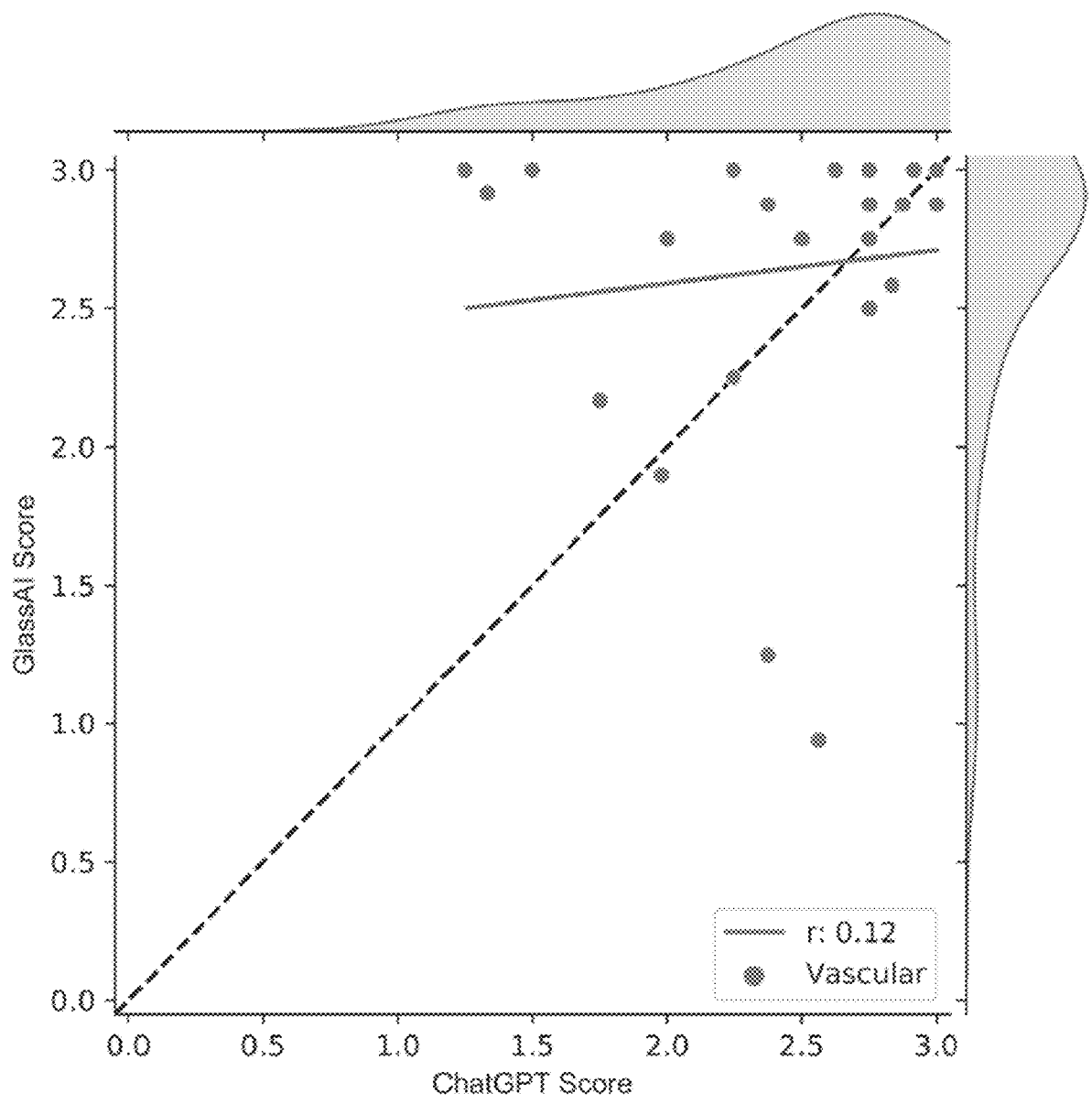
Figure 8D:
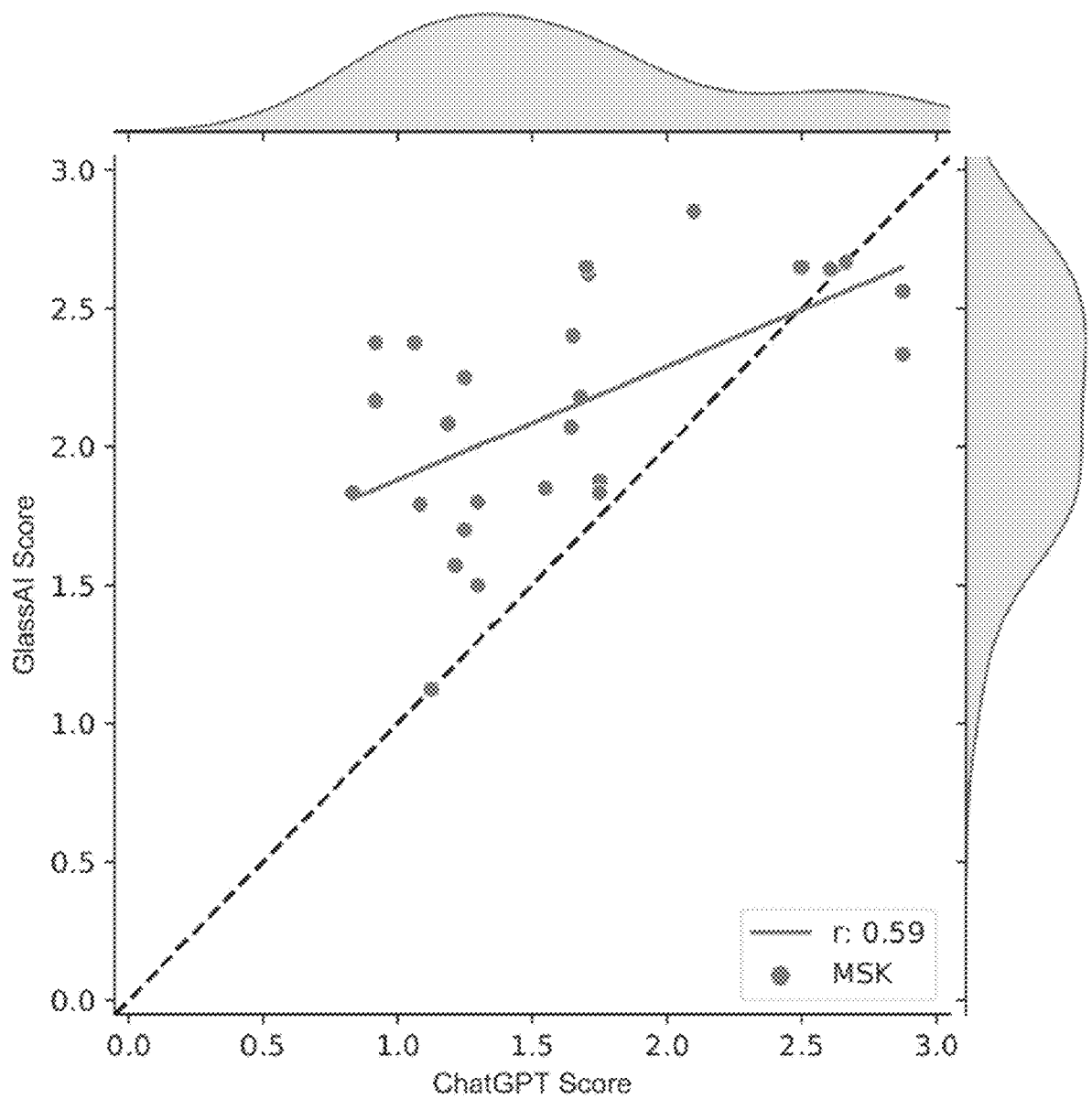
Figure 8E:
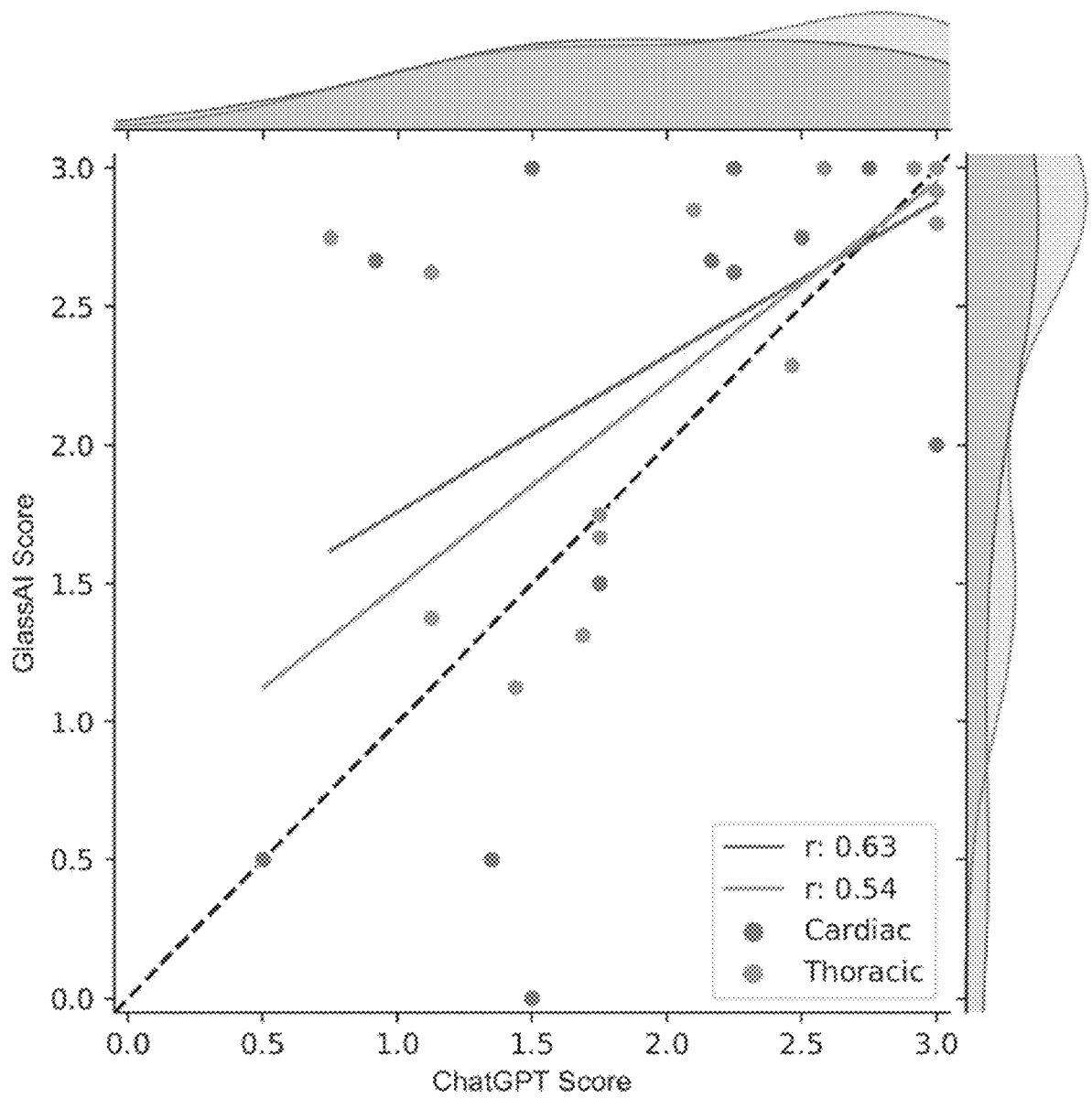
Figure 8F:
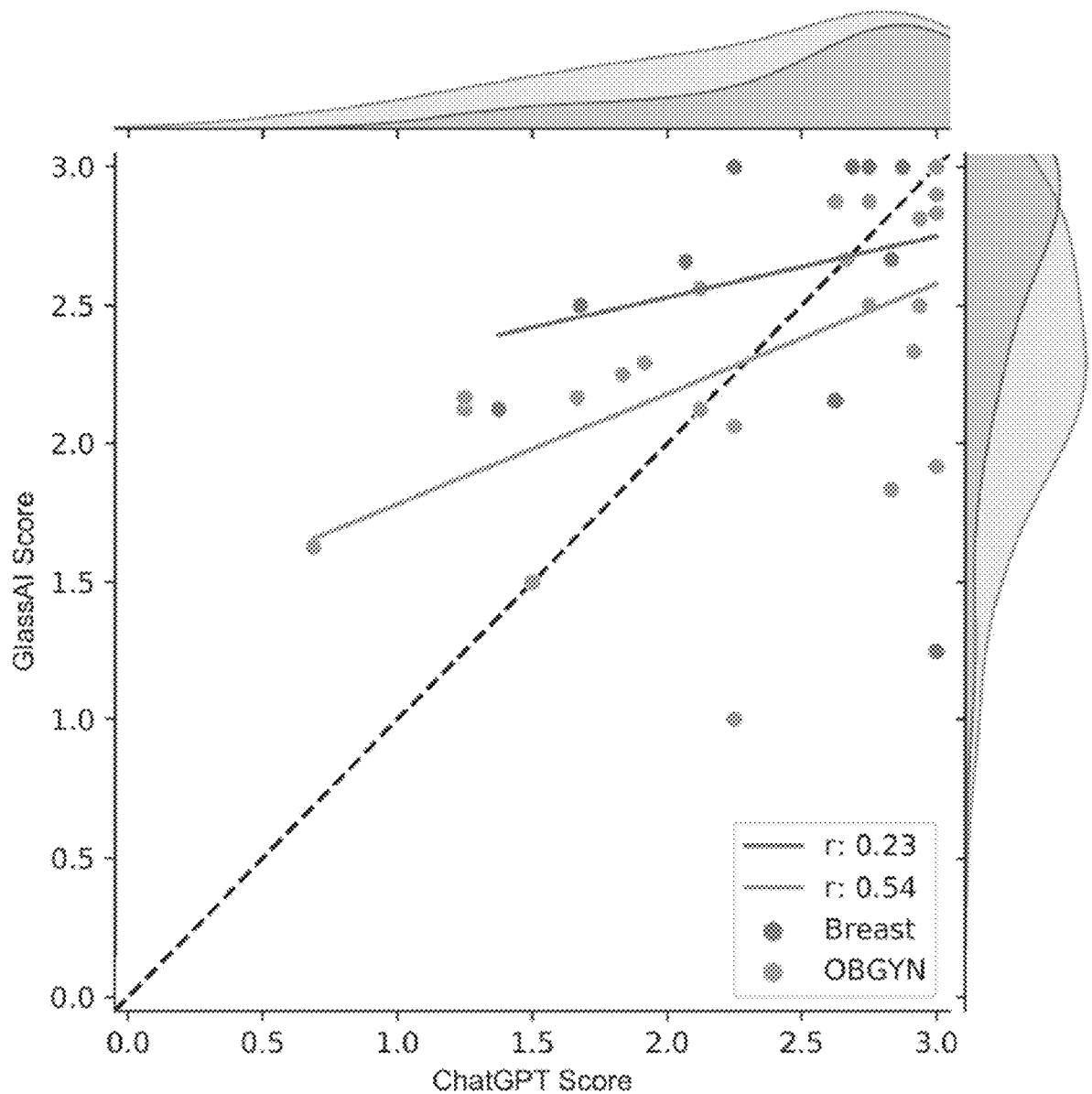
Figure 8G:
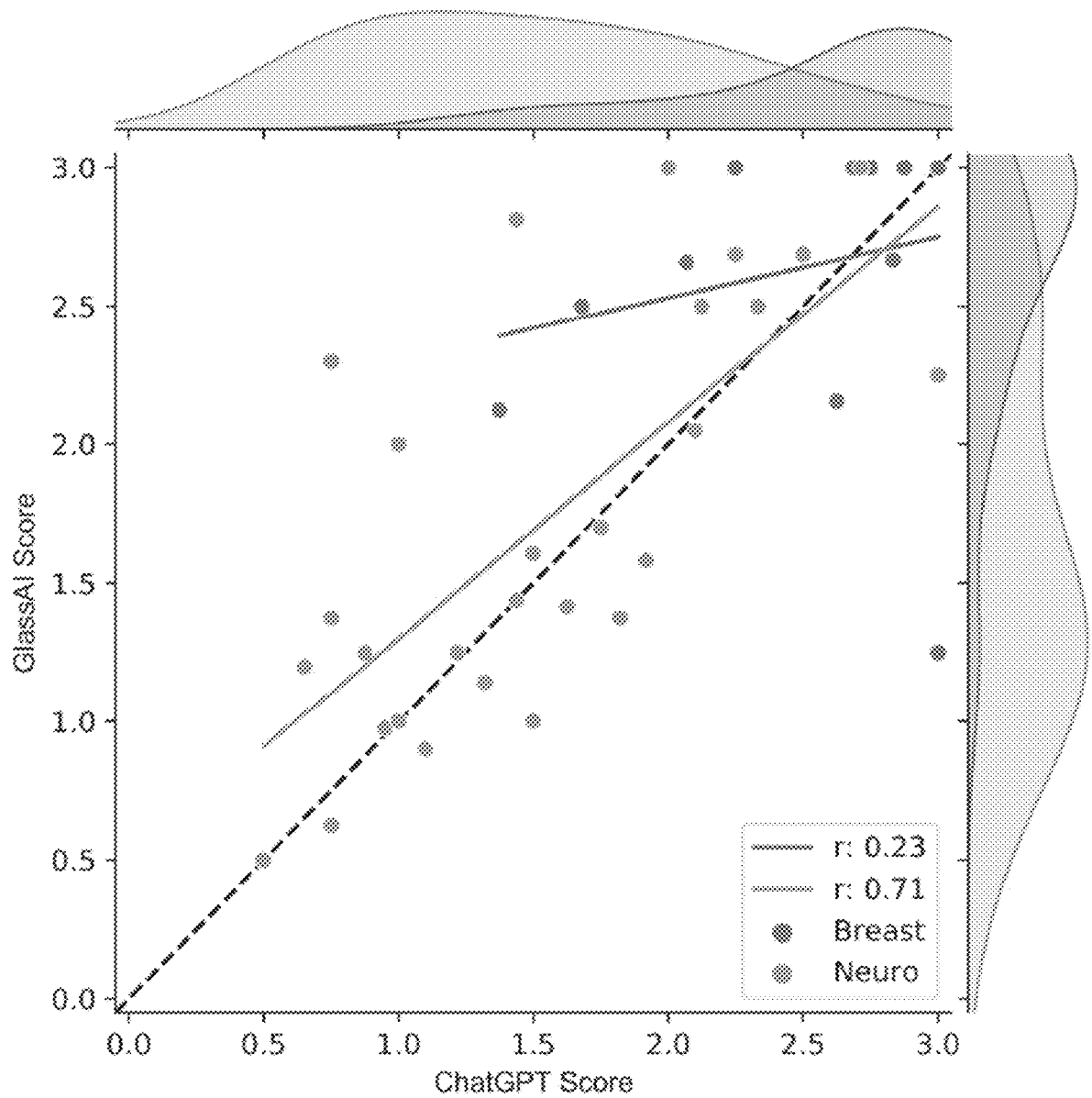
Figure 8H:
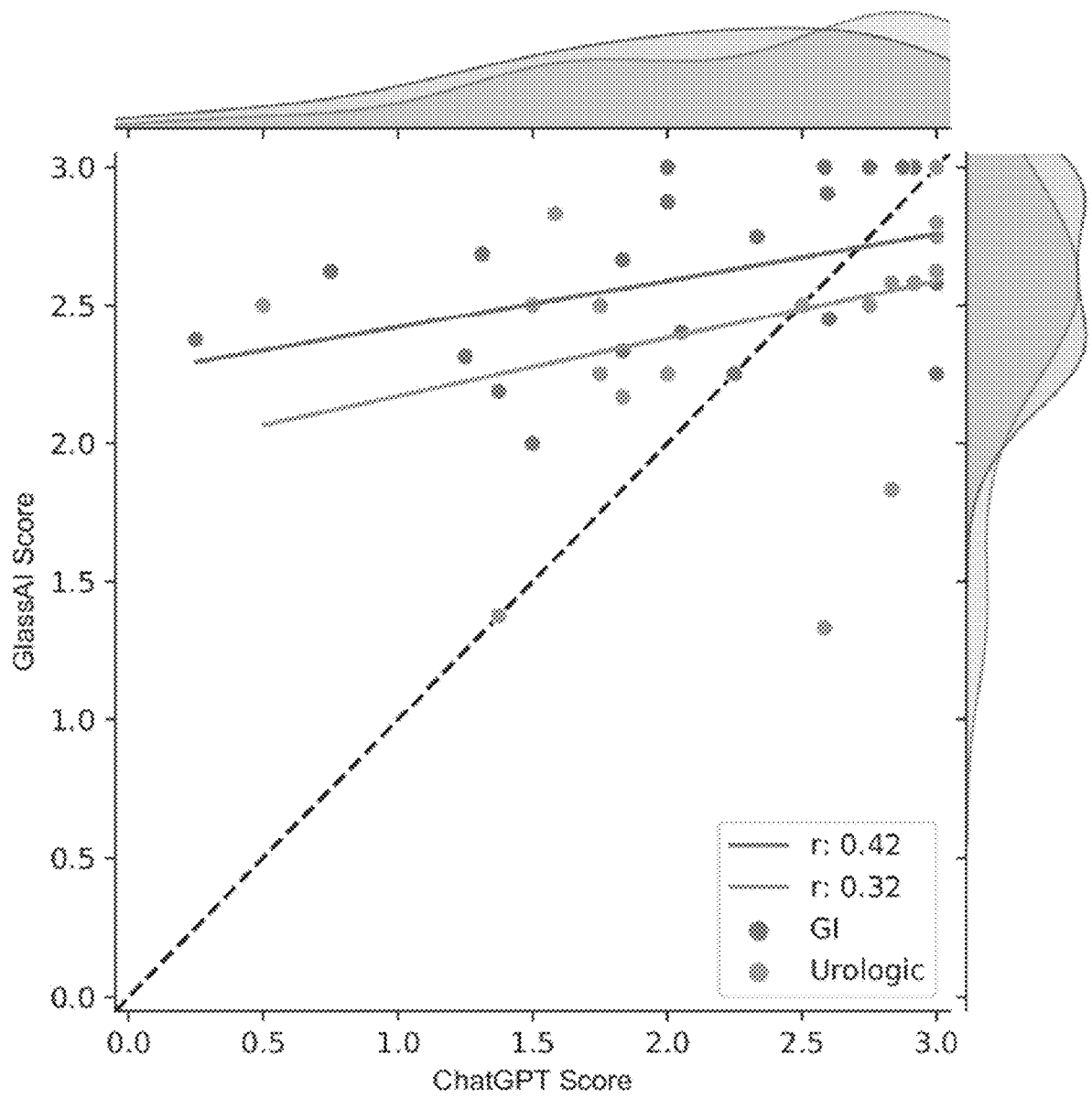

Comparison of ChatGPT™ and the LLM herein. FIG. 5 illustrates that the LLM herein significantly outperformed ChatGPT™ in predicting imaging studies (p=0.002) when averaged across all panels. FIG. 6 calculates the agreement between both LLMs for all panels (FIG. 2). The correlation coefficient is 0.57, indicating a moderately positive agreement between the two LLMs. The average scores for the LLM herein were higher than those of ChatGPT™ in 10 of 11 panels, with obstetrician gynecologist (OB/GYN) being the outlier. The LLM herein significantly outperformed ChatGPT™ in the gastroenterology (GI, p=0.002) and MSK (p<0.001) panels. FIG. 7 depicts that the LLM's herein higher performance in breast (p=0.28), cardiac (p=0.34), pediatrician (peds, p=0.30), thoracic (p=0.21), urologic (p=0.61), vascular (p=0.10), and neurologic (neuro, p=0.17) was not statistically significant. Upon qualitative analysis, ChatGPT™ would often provide rationale in its responses in which it would reference the usage of contrast, radiation safety, and imaging signs. The LLM herein, on the other hand, would output a list of imaging study choices, offering significantly less detail than ChatGPT™.

Comparison of ChatGPT™ and the LLM herein in radiologic subspecialties. FIGS. 8A-8H compare the results of ChatGPT™ and the LLM herein. For example, individual panels were compared and grouped by different radiologist subspecialties, e.g., women's health, chest, body, pediatrics, neurologic, and vascular. Both average scores and correlation coefficients were calculated. In each panel, the average score describes whether the LLM herein outperformed ChatGPT™, while the correlation coefficient describes the similarity in performance across questions. Panels with the highest R-values, which can indicate a concordance in performance between ChatGPT™ and the LLM herein, were pediatrics, neurologic, and thoracic. Panels with the lowest R-values, which can indicate a discordance in performance between ChatGPT™ and the LLM herein, were breast, urologic, and vascular. As shown in Table 2, a higher mean score in these panels indicates that the LLM herein outperformed ChatGPT™. However, the correlation compares the similarity in performance on a per-question basis and can be indicative of context-specific performance. For example, ChatGPT™ and the LLM herein can outperform each other on different sets of question topics allowing for similar average scores with lower correlations, e.g., breast, urologic, and dissimilar average scores with higher correlations. e.g., pediatrics and neurologic.

TABLE 2

| Panel | ChatGPT ™ | Platform herein | P-Value |
| --- | --- | --- | --- |
| Breast | 2.58 ± 0.54 | 2.66 ± 0.52 | 0.28 |
| Cardiac | 2.00 ± 0.78 | 2.21 ± 1.07 | 0.34 |
| GI | 2.05 ± 0.76 | 2.06 ± 0.32 | 0.002* |
| OB/GYN | 2.32 ± 0.69 | 2.30 ± 0.51 | 0.95 |
| MSK | 1.63 ± 0.62 | 2.13 ± 0.44 | <0.001* |
| Peds | 2.15 ± 0.61 | 2.26 ± 0.71 | 0.30 |
| Polytrauma | 2.53 | 2.88 | — |
| Thoracic | 2.19 ± 0.78 | 2.44 ± 0.70 | 0.21 |
| Urologic | 2.34 ± 0.74 | 2.44 ± 0.48 | 0.61 |

TABLE 2-continued

| Panel | ChatGPT ™ | Platform herein | P-Value |
| --- | --- | --- | --- |
| Vascular | 2.47 ± 0.53 | 2.66 ± 0.55 | 0.10 |
| Neuro | 1.54 ± 0.67 | 1.75 ± 0.74 | 0.17 |

Comparison of ChatGPT™ and the IIM herein to previous work. A previous study compared the performance of ChatGPT-3.5 and the LLM herein on the neurologic panel, as well as with a practicing radiologist. See Nazario-Johnson et al herein. ChatGPT™, the LLM herein, and the neuroradiologist scored 1.75, 1.83, and 2.19, respectively. On the same panel, ChatGPT-4 and the LLM herein scored 1.53 and 1.72, respectively. There was a statistically significant difference between the scores of ChatGPT-4 and ChatGPT-3.5 (p=0.003), but no difference between the outputs of the LLM herein. The scores of ChatGPT-4 and the LLM herein did not outperform the neuroradiologist.

DISCUSSION

This study shows that large language models (LLMs) which utilize RAG can more accurately predict appropriate imaging studies for patient clinical presentations than base LLMs. ChatGPT™ and the LLM herein can predict the appropriate imaging studies for variant clinical presentations in the ACR Appropriateness Criteria panels. The successful application of LLMs in this context may underscore their potential as a decision-support tool in medicine to improve healthcare outcomes. By offering radiological clinical support, LLMs may aid in faster and more accurate diagnoses and potentially improve health care outcomes. The significant difference between the average ChatGPT™ score (2.08) and the score of the LLM herein (2.32) in predicting the most appropriate imaging study across panels in the ACR criteria may indicate that medical-specific LLMs can outperform base LLMs such as ChatGPT™. As an LLM's output can be directly related to the training data, it is within reason that medical-specific training would improve the model's performance in that area. ChatGPT-4 did not outperform ChatGPT-3.5 on the neurologic criteria when compared to results published in a prior study. See Nazario-Johnson et al herein. However, ChatGPT-4 did outperform ChatGPT-3.5 on the breast screening and breast pain topics. This result may be explainable. For example, the breast panel may be less complex to predict, as demonstrated by both ChatGPT™ and the LLM herein performing the best in this panel. Additionally, neurologic presentations, due to their potentially more complex clinical presentations, may be more difficult to predict, as demonstrated by both the performance of ChatGPT-4 and the LLM herein as illustrated for breast and neuro in FIG. 8G.

While this study highlights the performance of LLMs utilizing RAG in accurately predicting imaging studies, it may also illustrate a few shortcomings. As previously mentioned, the ability of LLMs to generate text can be directly related to their training data. If the LLM is not trained on medical data, for example, then may be unable to generate text in that context. ChatGPT's™ knowledge cutoff is around September 2021, so any new research or guidelines that may have occurred after this date are not incorporated into ChatGPT's™ model. This may be mitigated by regularly updating the data with the latest literature and guidelines and could turn out to be a benefit, especially in a field like radiology where innovation and technology are at its core. As such, LLMs can help radiologists stay up-to-date with the newest research and guidelines.

This study can serve as a demonstration in the improvement of the LLM herein compared to other LLMs such as ChatGPT™ t. Future studies may, e.g., show its effectiveness in clinical practice. For example, LLMs may provide information that a physician can consider in making healthcare decisions. In some cases, the performance of LLMs can be highly dependent on the quality of the prompt. For example, the prompt can influence the output of the LLM by setting the context for the conversation. As such, poorly described or vague patient presentations can result in less accurate outputs. Prompt standardization may be useful given the context-dependent performances of the models. Because the LLM herein may have been tuned using medical data, this could bias scoring for certain prompt contexts. Even though, in some panels, where average scoring is similar for the LLM herein and ChatGPT™, yet there is a low question-to-question correlation, prompt engineering may be important for standardizing performance. This is also highlighted in the observation that older GPT-3.5-based models outperformed newer GPT-4-based models. This apparent loss of performance is also seen in recent findings where GPT-3.5 again outperformed GPT-4, albeit on a simpler task involving prime numbers. Here, degradation in performance was on the more complex task of selecting the appropriate imaging study. Although taken together these could suggest that GPT versions are becoming worse at both simple and complex tasks, it could be that this provides evidence for the sensitivity of models to prompt design. Given the identical inputs to each model, this observed behavioral drift could be corrected through a refined understanding of the context-specific prompt-output relationship of a given model and the underlying parameters and network architecture. This result also indicates the need to accelerate standardization because of the growing separation between our understanding of LLMs and their capabilities.

In some cases, LLMs can be viewed as "black boxes," which can mean they may lack interpretability of the generated output. Physicians may be reluctant to use these LLMs when delivering care to their patients if LLMs do not explain their results. Accordingly, there exists a need to build explainable AI models such as LLMs. As an example, explainability can include using heatmaps on chest X-rays to show what the model is using to generate its decision. However, even this approach may not be entirely effective. A more explainable AI may help to transition its use into clinical applications. Regardless, this study shows the utility for using LLMs to improve predicting imaging studies given patient presentations and to improve healthcare outcomes.

Computing Systems

In another aspect, disclosed herein is a computer program product for an artificial intelligence (AI)-based clinical decision support platform, the computer program product comprising at least one non-transitory computer-readable medium having computer-readable program code portions embodied therein, the computer-readable program code portions comprising: an executable user input processing portion configured to receive a clinical problem representation (CPR) based at least in part on an input provided by a user; an executable context matching portion configured to (1) process a prompt for refining the CPR and identify a suitable context, (2) provide the CPR along with one or more relevant context topics to a first large language model (LLM), and (3) use the first LLM to generate a first output comprising a preliminary clinical diagnosis and a context match relating to the CPR; an executable retrieval-augmented generation (RAG) portion configured to process the context match and the one or more relevant context topics using a physician-validated context library to determine a context topic based on physician-validated schemas or clinical guidelines for pushing into a second LLM; and an executable output generation portion configured to use the second LLM to process (1) the CPR, (2) the context based on the physician-validated schemas or clinical guidelines, and (3) one or more targeted prompts, to generate a second output comprising at least one of a differential diagnosis, an assessment of a health condition, or a treatment plan for the health condition.

In another aspect, disclosed herein is a computer program product for an artificial intelligence (AI)-based clinical decision support platform, the computer program product comprising at least one non-transitory computer-readable medium having computer-readable program code portions embodied therein, the computer-readable program code portions comprising: an executable user input processing portion configured to receive at least a clinical reference question (CRQ) based at least in part on an input provided by a user; an executable context matching portion configured to (1) process a prompt for refining and understanding at least the CRQ and identify a suitable context, (2) provide at least the CRQ along with one or more relevant context topics to a first large language model (LLM), and (3) use the first LLM to generate a first output comprising a preliminary clinical diagnosis and a context match relating to a clinical problem representation (CPR); an executable retrieval-augmented generation (RAG) portion configured to process the context match and the one or more relevant context topics using a physician-validated context library, to determine a context topic based on physician-validated clinical guidelines for pushing into a second LLM; and an executable output generation portion configured to use the second LLM to process (1) the CPR, (2) the context based on the physician-validated clinical guidelines, and (3) one or more targeted prompts for answering the CRQ, to generate a second output comprising of an answer to the CRQ, wherein the answer is provided to the user through a chatbot interface.

Figure 14:
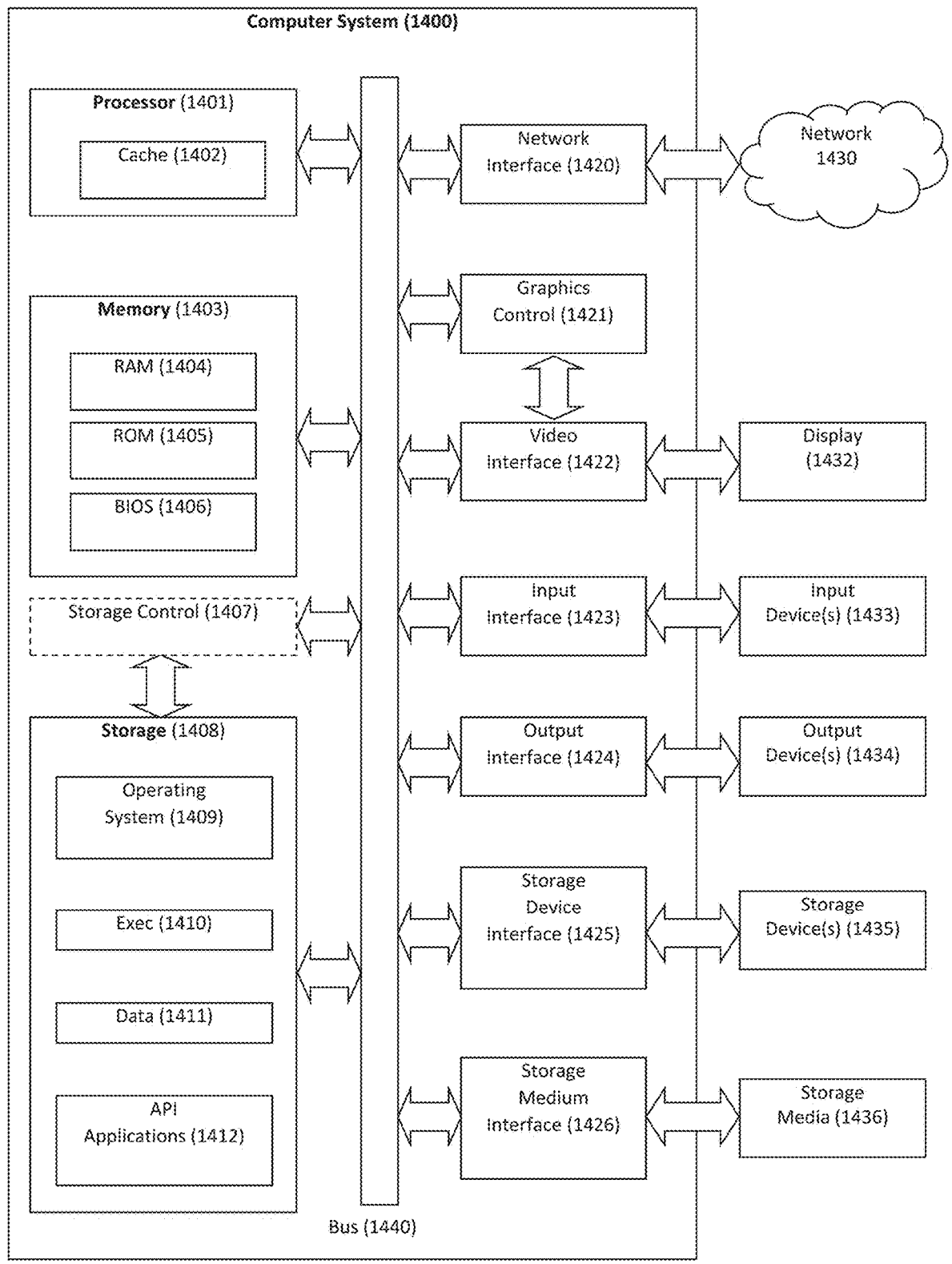
FIG. 14 illustrates an example computing device configured to perform methods herein, in accordance with some embodiments.

The systems and methods described herein may be partially or fully implemented by a special purpose computer system. In some cases, the special purpose computer system can be created by configuring a general-purpose computer to execute one or more particular functions embodied in computer programs. Referring to FIG. 14, a block diagram is shown depicting an exemplary machine that includes a computer system 1400 (e.g., a processing or computing system) within which a set of instructions can execute for causing a device to perform or execute any one or more of the aspects and methods of the present disclosure. The components in FIG. 14 are examples only and do not limit the scope of use or functionality of any hardware, software, embedded logic component, or a combination of two or more such components implementing particular embodiments.

Computer system 1400 may include one or more processors 1401, a memory 1403, and a storage 1408 that communicate with each other, and with other components, via a bus 1440. The bus 1440 may also link a display 1432, one or more input devices 1433 (which may, for example, include a keypad, a keyboard, a mouse, a stylus, etc.), one or more output devices 1434, one or more storage devices 1435, and various tangible storage media 1436. All of these elements may interface directly or via one or more interfaces or adaptors to the bus 1440. For instance, the various tangible storage media 1436 can interface with the bus 1440 via storage medium interface 1426. Computer system 1400 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 1400 includes one or more processor(s) 1401 (e.g., central processing units (CPUs) or general purpose graphics processing units (GPGPUs)) that carry out functions. Processor(s) 1401 optionally contains a cache memory unit 1402 for temporary local storage of instructions, data, or computer addresses. Processor(s) 1401 are configured to assist in execution of computer readable instructions. Computer system 1400 may provide functionality for the components depicted in FIG. 14 as a result of the processor(s) 1401 executing non-transitory, processor-executable instructions embodied in one or more tangible computer-readable storage media, such as memory 1403, storage 1408, storage devices 1435, and/or storage medium 1436. The computer-readable media may store software that implements particular embodiments, and processor(s) 1401 may execute the software. Memory 1403 may read the software from one or more other computer-readable media (such as mass storage device(s) 1435, 1436) or from one or more other sources through a suitable interface, such as network interface 1420. The software may cause processor(s) 1401 to carry out one or more processes or one or more steps of one or more processes described or illustrated herein. Carrying out such processes or steps may include defining data structures stored in memory 1403 and modifying the data structures as directed by the software.

The memory 1403 may include various components (e.g., machine readable media) including, but not limited to, a random access memory component (e.g., RAM 1404) (e.g., static RAM (SRAM), dynamic RAM (DRAM), ferroelectric random access memory (FRAM), phase-change random access memory (PRAM), etc.), a read-only memory component (e.g., ROM 1405), and any combinations thereof. ROM 1405 may act to communicate data and instructions unidirectionally to processor(s) 1401, and RAM 1404 may act to communicate data and instructions bidirectionally with processor(s) 1401. ROM 1405 and RAM 1404 may include any suitable tangible computer-readable media described below. In one example, a basic input/output system 1406 (BIOS), including basic routines that help to transfer information between elements within computer system 1400, such as during start-up, may be stored in the memory 1403.

Fixed storage 1408 is connected bidirectionally to processor(s) 1401, optionally through storage control unit 1407. Fixed storage 1408 provides additional data storage capacity and may also include any suitable tangible computer-readable media described herein. Storage 1408 may be used to store operating system 1409, executable(s) 1410, data 1411, applications 1412 (application programs), and the like. Storage 1408 can also include an optical disk drive, a solid-state memory device (e.g., flash-based systems), or a combination of any of the above. Information in storage 1408 may, in appropriate cases, be incorporated as virtual memory in memory 1403.

In one example, storage device(s) 1435 may be removably interfaced with computer system 1400 (e.g., via an external port connector (not shown)) via a storage device interface 1425. Particularly, storage device(s) 1435 and an associated machine-readable medium may provide non-volatile and/or volatile storage of machine-readable instructions, data structures, program modules, and/or other data for the computer system 1400. In one example, software may reside, completely or partially, within a machine-readable medium on storage device(s) 1435. In another example, software may reside, completely or partially, within processor(s) 1401.

Bus 1440 connects a wide variety of subsystems. Herein, reference to a bus may encompass one or more digital signal lines serving a common function, where appropriate. Bus 1440 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 1400 may also include an input device 1433. In one example, a user of computer system 1400 may enter commands and/or other information into computer system 1400 via input device(s) 1433. Examples of an input device(s) 1433 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect®, Leap Motion®, or the like. Input device(s) 1433 may be interfaced to bus 1440 via any of a variety of input interfaces 1423 (e.g., input interface 1423) including, but not limited to, serial, parallel, game port, USB, FIREWIRE, THUNDERBOLT, or any combination of the above.

In particular embodiments, when computer system 1400 is connected to network 1430, computer system 1400 may communicate with other devices, specifically mobile devices and enterprise systems, distributed computing systems, cloud storage systems, cloud computing systems, and the like, connected to network 1430. Communications to and from computer system 1400 may be sent through network interface 1420. For example, network interface 1420 may receive incoming communications (such as requests or responses from other devices) in the form of one or more packets (such as Internet Protocol (IP) packets) from network 1430, and computer system 1400 may store the incoming communications in memory 1403 for processing. Computer system 1400 may similarly store outgoing communications (such as requests or responses to other devices) in the form of one or more packets in memory 1403 and communicated to network 1430 from network interface 1420. Processor(s) 1401 may access these communication packets stored in memory 1403 for processing.

Examples of the network interface 1420 include, but are not limited to, a network interface card, a modem, and any combination thereof. Examples of a network 1430 or network segment 1430 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 1430, may employ a wired and/or a wireless mode of communication. In general, any network topology may be used.

Information and data can be displayed through a display 1432. Examples of a display 1432 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 1432 can interface to the processor(s) 1401, memory 1403, and fixed storage 1408, as well as other devices, such as input device(s) 1433, via the bus 1440. The display 1432 is linked to the bus 1440 via a video interface 1422, and transport of data between the display 1432 and the bus 1440 can be controlled via the graphics control 1421. In some embodiments, the display is a video projector. In some embodiments, the display is a head-mounted display (HMD) such as a VR headset. In further embodiments, suitable VR headsets include, by way of non-limiting examples. HTC Vive®, Oculus Rift. Samsung Gear VR®, Microsoft HoloLens®, Razer OSVR®, FOVE VR®, Zeiss VR One®. Avegant Glyph®, Freefly VR® headset, and the like. In still further embodiments, the display is a combination of devices such as those disclosed herein.

In addition to a display 1432, computer system 1400 may include one or more other peripheral output devices 1434 including, but not limited to, an audio speaker, a printer, a storage device, and any combinations thereof. Such peripheral output devices may be connected to the bus 1440 via an output interface 1424. Examples of an output interface 1424 include, but are not limited to, a serial port, a parallel connection, a USB port, a FIREWIRE port, a THUNDER-BOLT port, and any combinations thereof.

In addition or as an alternative, computer system 1400 may provide functionality as a result of logic hardwired or otherwise embodied in a circuit, which may operate in place of or together with software to execute one or more processes or one or more steps of one or more processes described or illustrated herein. Reference to software in this present disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality The various illustrative logical blocks, modules, and circuits described in connection with the embodiments disclosed herein may be implemented or performed with a general purpose processor, a digital signal processor (DSP), an application specific integrated circuit (ASIC), afield programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, sub-notebook computers, netbook computers, netpad computers, set-top computers, media streaming devices, handheld computers. Internet appliances, mobile smartphones, tablet computers, personal digital assistants, video game consoles, and vehicles. Select televisions, video players, and digital music players with optional computer network connectivity are suitable for use in the system described herein. Suitable tablet computers, in various embodiments, include those with booklet, slate, and convertible configurations.

In some embodiments, the computing device includes an operating system configured to perform executable instructions. The operating system is, for example, software, including programs and data, which manages the device's hardware and provides services for execution of applications. Suitable server operating systems include, by way of non-limiting examples, FreeBSD®, OpenBSD®, NetBSD®, Linux®, Apple® Mac OS X Server®, Oracle Solaris®, Windows Server®, and Novell NetWare®. Suitable personal computer operating systems include, by way of non-limiting examples, Microsoft Windows®, Apple Mac® OS X, UNIX®, and UNIX-like operating systems such as GNU/Linux®. In some embodiments, the operating system is provided by cloud computing. Suitable mobile smartphone operating systems include, by way of non-limiting examples, Nokia Symbian® OS, Apple® iOS, Research In Motion BlackBerry® OS, Google® Android®, Microsoft® Windows Phone® OS, Microsoft® Windows Mobile OS. Linux®, and Palm® WebOS. Suitable media streaming device operating systems include, by way of non-limiting examples, Apple TV®, Roku®, Boxee®, Google TV®, Google Chromecast®, Amazon Firex, and Samsung® HomeSync®. Suitable video game console operating systems include, by way of non-limiting examples, Sony® PS3, Sony® PS4®, Microsoft® Xbox 360®, Microsoft Xbox One®. Nintendo Wii®, Nintendo Wii U®, and Ouya®. Suitable virtual reality headset systems include, by way of non-limiting example, Meta Oculus®.

Non-Transitory Computer Readable Storage Mediums

In some embodiments, the platforms, systems, media, and methods disclosed herein include one or more non-transitory computer readable storage media encoded with a program including instructions executable by the operating system of an optionally networked computing device. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Programs

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, which perform particular tasks or implement particular abstract data types. In light of the present disclosure provided herein, a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Applications

In some embodiments, a computer program includes a web application. In light of the present disclosure provided herein, a web application, in various embodiments, utilizes one or more software frameworks and one or more database systems. In some embodiments, a web application is created upon a software framework such as Microsoft®.NET or Ruby on Rails® (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® structured query language (SQL) Server®, mySQL™, and Oracle™. A web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous JavaScript and XML® (AJAX), Flash ActionScript, Javascript®, or Silverlight®. In some embodiments, a web application is written to some extent in a server-side coding language such as Active Server Pages® (ASP), ColdFusion®, Perl®, Java, JavaServer Pages® (JSP), Hypertext Preprocessor® (PHP), Python®, Ruby®. Tcl®, Smalltalk®, WebDNA®, or Groovy®. In some embodiments, a web application is written to some extent in a database query language such as Structured Query Language (SQL). In some embodiments, a web application integrates enterprise server products such as IBM Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft Silverlight®, Java, and Unity®.

Figure 15:
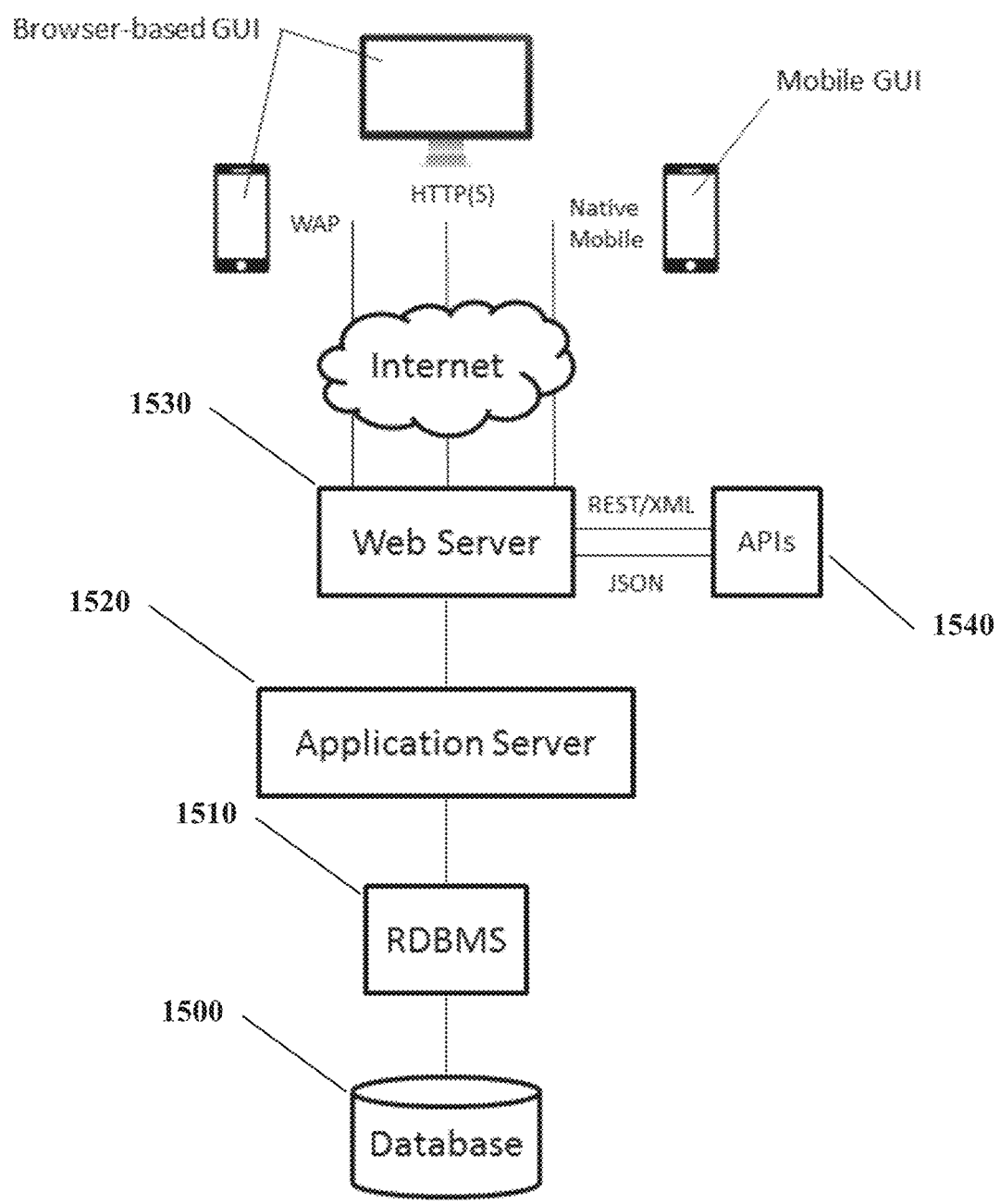
FIG. 15 illustrates an example web or mobile application provision system configured to perform methods herein, in accordance with some embodiments.

Referring to FIG. 15, in a particular embodiment, an application provision system comprises one or more databases 1500 accessed by a database management system (DBMS) 1510. Suitable DBMSs include Firebird®, MySQL®, NoSQL®, PostgreSQL®, SQLite®, Oracle Database®, Microsoft SQL Server®, IBM DB2®, IBM Informix®, SAP Sybase®, SAP Sybase®, Teradata®, PostGIS®, Apache® Hive, Apache® Impala, time-series databases, graph databases, key-value storage, and the like. In this embodiment, the application provision system further comprises one or more application severs 1520 (such as Java® servers, .NET® servers, PHP® servers, and the like) and one or more web servers 1530 (such as Apache®, IIS®, GWS® and the like). The web server(s) optionally expose one or more web services via app application programming interfaces (APIs) 1540. Via a network, such as the Internet, the system provides browser-based and/or mobile native user interfaces. In some cases, a DBMS may be a relational DBMS.

Figure 16:
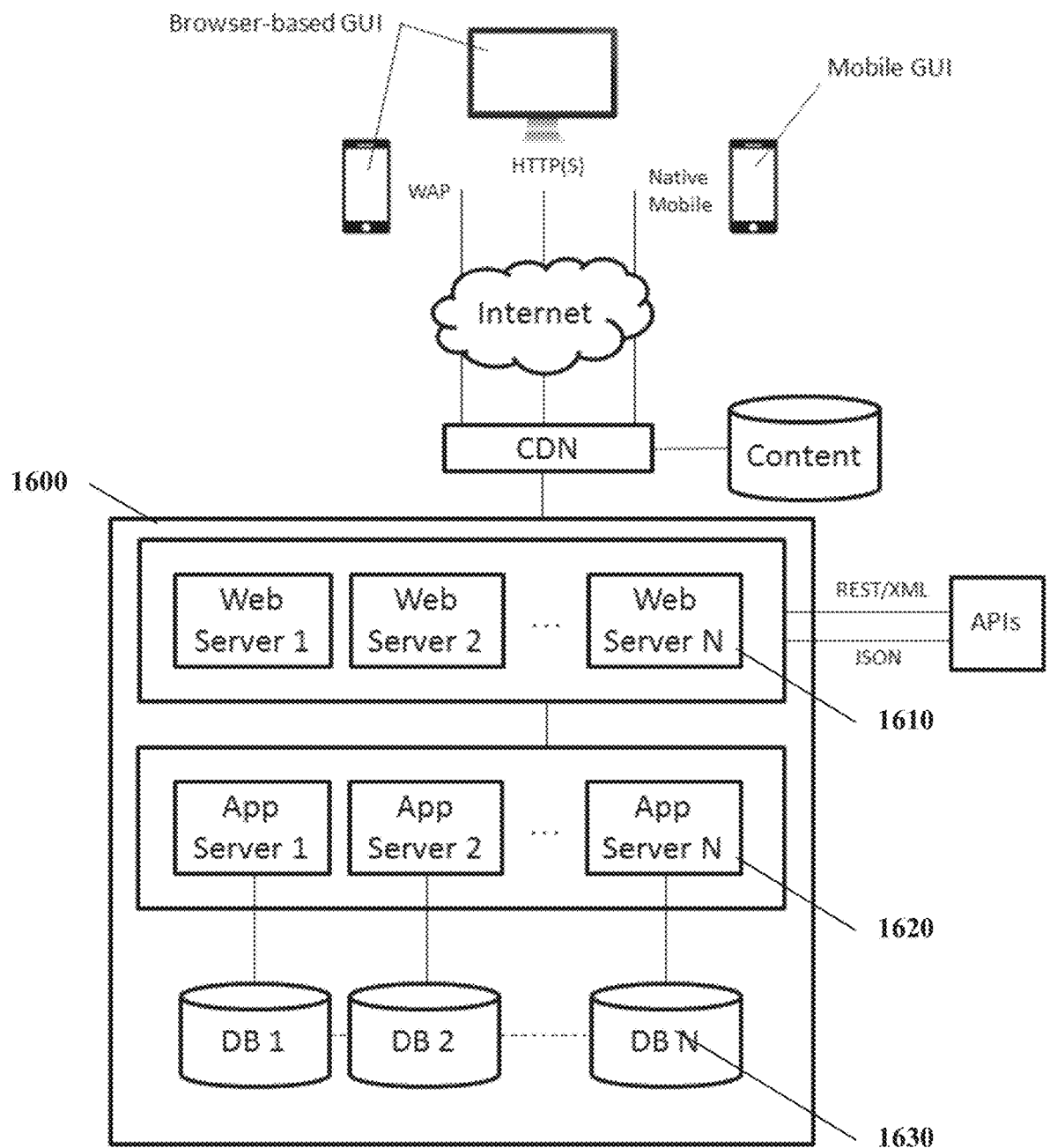
FIG. 16 illustrates an example cloud-based web or mobile application provision system configured to perform methods herein, in accordance with some embodiments.

Referring to FIG. 16, in a particular embodiment, an application provision system alternatively has a distributed, cloud-based architecture 1600 and comprises elastically load balanced, auto-scaling web server resources 1610 and application server resources 1620 as well synchronously replicated databases 1630.

Mobile Applications

In some embodiments, a computer program includes a mobile application provided to a mobile computing device. In some embodiments, the mobile application is provided to a mobile computing device at the time it is manufactured. In other embodiments, the mobile application is provided to a mobile computing device via the computer network described herein.

In view of the present disclosure provided herein, a mobile application is created by techniques using hardware, languages, and development environments. Mobile applications are written in several languages. Suitable programming languages include, by way of non-limiting examples, C, C++, C#, Objective-C, Java®, JavaScript®, Pascal®, Object Pascal®, Python™. Ruby®, VB.NET®, WML®, and XHTML/HTML with or without CSS, or combinations thereof.

Suitable mobile application development environments are available from several sources. Commercially available development environments include, by way of non-limiting examples, AirplaySDK®, alcheMo®, Appcelerator®, Celsius®, Bedrock®, Flash Lite®, .NET Compact Framework®, Rhomobile®, and WorkLight Mobile Platform®.

Other development environments are available without cost including, by way of non-limiting examples, Lazarus®, MobiFlex®, MoSync®, and PhoneGap®. Also, mobile device manufacturers distribute software developer kits including, by way of non-limiting examples, iPhone® and iPad® (iOS) SDK, Android® SDK, BlackBerry® SDK, BREW SDK, Palm® OS SDK, Symbian® SDK, webOS® SDK, and Windows® Mobile SDK.

Several commercial sources are available for distribution of mobile applications including, by way of non-limiting examples, Apple® App Store, Google® Play, Chrome® WebStore, BlackBerry® App World, App Store® for Palm devices, App Catalog® for webOS, Windows® Marketplace for Mobile, Ovi Store for Nokia® devices, Samsung® Apps, and Nintendo® DSi Shop.

Standalone Applications

In some embodiments, a computer program includes a standalone application, which is a program that is run as an independent computer process, not an add-on to an existing process, e.g., not a plug-in. Standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL®, Delphi®, Eiffel®, Javas, Lisp®, Python®. Visual Basic®, and VB .NET®, or combinations thereof. Compilation is often performed, at least in part, to create an executable program. In some embodiments, a computer program includes one or more executable compiled applications. Additionally, microservices related to Python® and JavaScript® may be used.

Web Browser Plug-Ins

In some embodiments, the computer program includes a web browser plug-in (e.g., web extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Several web browser plug-ins may include Adobe Flash Player®, Microsoft Silverlight®, and Apple QuickTime®. In some embodiments, the toolbar comprises one or more web browser extensions, add-ins, or add-ons. In some embodiments, the toolbar comprises one or more explorer bars, tool bands, or desk bands.

In view of the present disclosure provided herein, several plug-in frameworks are available that enable development of plug-ins in various programming languages, including, by way of non-limiting examples, C++, Delphi®, Java®, PHP®, Python®, and VB .NET®, or combinations thereof.

Web browsers (also called Internet browsers) are software applications, designed for use with network-connected computing devices, for retrieving, presenting, and traversing information resources on the World Wide Web. Suitable web browsers include, by way of non-limiting examples. Microsoft Internet Explorer. Mozilla Firefox®, Google Chrome®, Apple Safari®, Opera Software Opera®, and KDE Konqueror®. In some embodiments, the web browser is a mobile web browser. Mobile web browsers (also called microbrowsers, mini-browsers, and wireless browsers) are designed for use on mobile computing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google Android® browser, RIM BlackBerrv® Browser. Apple Safari®, Palm Blazer®, Palm WebOS® Browser, Mozilla Firefox® for mobile, Microsoft Internet Explorer Mobile®, Amazon Kindle Basic Web®, Nokia Browser®. Opera Software Opera Mobile®, and Sony PSP® browser.

Software Modules

In some embodiments, the platforms, systems, media, and methods disclosed herein include software, server, and/or database modules, or use of the same. In view of the present disclosure provided herein, software modules are created by techniques using machines, software, and languages. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the platforms, systems, media, and methods disclosed herein include one or more databases (DB), or use of the same. In view of the present disclosure provided herein, many databases are suitable for storage and retrieval data. In various embodiments, suitable databases include, by way of non-limiting examples, relational databases, non-relational databases, object oriented databases, object databases, entity-relationship model databases, associative databases, XML databases, time-series databases, graph databases, and the like. Further non-limiting examples include SQL, PostgreSQL®, MySQL®, Oracle®, DB2®, and Sybase. In some embodiments, a database is internet-based. In further embodiments, a database is web-based. In still further embodiments, a database is cloud computing-based. In a particular embodiment, a database is a distributed database. In other embodiments, a database is based on one or more local computer storage devices.

Terms and Definitions

Unless otherwise defined, all technical terms used herein have the same meaning as commonly understood by one of ordinary skill in the art to which this present disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one," "one or more," and "and/or" are open-ended expressions that are both conjunctive and disjunctive in operation. For example, each of the expressions "at least one of A, B and C." "at least one of A, B, or C," "one or more of A, B, and C", "one or more of A, B, or C" and "A, B, and/or C" means A alone, B alone, C alone, A and B together, A and C together, B and C together, or A, B and C together.

While preferred embodiments of the present disclosure have been shown and described herein, such embodiments are provided by way of example only. It is not intended that the present disclosure be limited by the specific examples provided within the specification. While the present disclosure has been described with reference to the aforementioned specification, the descriptions and illustrations of the embodiments herein are not meant to be construed in a limiting sense. Numerous variations, changes, and substitutions may occur without departing from the present disclosure. Furthermore, it shall be understood that all aspects of the present disclosure are not limited to the specific depictions, configurations, or relative proportions set forth herein which depend upon a variety of conditions and variables. It should be understood that various alternatives to the embodiments of the present disclosure described herein may be employed in practicing the present disclosure. It is therefore contemplated that the present disclosure shall also cover any such alternatives, modifications, variations, or equivalents. It is intended that the following claims define the scope of the present disclosure and that systems, methods and structures within the scope of these claims and their equivalents be covered thereby.

What is claimed is:

1. An artificial intelligence (AI)-based clinical decision support platform for treating a patient with a health condition, the platform comprising:
    a user input processing module configured to receive a clinical problem representation (CPR) based at least in part on an input provided by a healthcare provider (HCP) or a patient, wherein the CPR comprises a list of one or more symptoms presented or determined in real time during a patient encounter;
    a context matching module comprising a first large language model (LLM) generally trained using general or historical data, wherein the first LLM is configured to determine a clinical diagnosis of the health condition by (1) iteratively processing a first set of prompts using a plurality of healthcare context topics generated from a physician-validated context library and (2) determining, using the first set of prompts, a context match from the plurality of healthcare context topics, wherein the context match associates the health condition with at least one of the plurality of healthcare context topics with a confidence level;
    a retrieval-augmented generation (RAG) module comprising the physician-validated context library, wherein the RAG module is configured to: (1) generate the plurality of healthcare context topics for use by the context matching module and (2) identify physician-validated schemas and clinical guidelines for treating the health condition; and
    an output generation module comprising a second LLM trained using the physician-validated context library, wherein the second LLM is configured to determine a plurality of treatment plans for treating the health condition by (1) iteratively processing a second set of prompts using the context match and the physician-validated schemas and clinical guidelines and (2) determining, using the second set of prompts, at least one treatment plan of the plurality of treatment plans,
    wherein the at least one treatment plan is used to treat the patient having or suspected of having the health condition based at least on a confidence level of the clinical diagnosis.

2. The platform of claim 1, wherein the user input processing module is further configured to generate the CPR.

3. The platform of claim 1, wherein the first set of prompts comprises a prompt for use by the first LLM to generate a differential diagnosis.

4. The platform of claim 1, wherein the second set of prompts comprises a prompt for use by the second LLM to generate an assessment for the health condition.

5. The platform of claim 1, wherein the RAG module is further configured to dynamically provide the plurality of healthcare context topics iteratively back to (i) the context matching module for subsequent use by the first LLM or (ii) the output generation module for subsequent use by the second LLM.

6. The platform of claim 1, further comprising an AI-copilot module configured to generate data for a pre-visit clinical decision, wherein the data is received by the user input processing module to further assist the first LLM in generating the clinical diagnosis of the health condition or the second LLM in generating the at least one treatment plan for the health condition.

7. The platform of claim 1, further comprising an AI-notebook module configured to generate data associated with clinical knowledge, wherein the data is received by the user input processing module to further assist the first LLM in generating the clinical diagnosis of the health condition or the second LLM in generating the at least one treatment plan for the health condition.

8. The platform of claim 1, wherein the RAG module is further configured to use embedding-based matching to determine a relevance of the input provided by the HCP or the patient.

9. The platform of claim 1, wherein the RAG module is further configured to use one or more prompts to improve association of the context match to the plurality of healthcare context topics.

10. The platform of claim 9, wherein the first set of prompts, the second set of prompts, or the one or more prompts comprises chain-of-thought prompt engineering.

11. The platform of claim 1, wherein the RAG module is further configured to use N-shot learning to improve association of the context match to the plurality of healthcare context topics.

12. The platform of claim 11, wherein the N-shot learning comprises at least one learning example.

13. The platform of claim 1, wherein the input provided by the HCP or the patient comprises a text input, a speech input, a video input, or any combination thereof.

14. The platform of claim 13, wherein the platform is configured to (i) transform the speech input or the video input into a text input and (ii) transmit the text input to the user input processing module.

15. The platform of claim 5, wherein a number of iterations is based at least on a confidence level of the clinical diagnosis of the health condition or the at least one treatment plan for treating the health condition.

16. The platform of claim 15 wherein the confidence level is at least 80%.

17. The platform of claim 1, wherein the platform further comprises a graphical user interface (GUI) configured to display one or more structured healthcare reports to the HCP or the patient, and wherein the reports are structured into categories comprising the CPR, an assessment of the health condition, the clinical diagnosis of the health condition, and the at least one treatment plan for the health condition.

18. The platform of claim 1, wherein the CPR further comprises age, medical history, medications, associated symptoms, lab tests, or a course of the health condition.

19. The platform of claim 1, wherein the physician-validated context library is dynamically updated in real time for use by the context matching module.

20. A system comprising at least one processor and instructions executable by the at least one processor to cause the at least one processor to perform operations comprising:
  (a) receiving a clinical problem representation (CPR) based at least in part on an input provided by a healthcare provider (HCP) or a patient, wherein the CPR comprises a list of one or more symptoms presented or determined in real time during a patient encounter;
  (b) determining a clinical diagnosis by using the input to (1) iteratively process a first set of prompts using a plurality of healthcare context topics generated from a physician-validated context library and (2) determine, by a first large language model (LLM) using the first set of prompts, a context match from the plurality of healthcare context topics, wherein the context match associates the health condition with at least one of the plurality of healthcare context topics with a confidence level, and wherein the first LLM is generally trained using general or historical data;
  (c) using retrieval augmented generation (RAG) to (1) generate the plurality of healthcare context topics for use in determining the clinical diagnosis in (b) and (2) identify physician-validated schemas and clinical guidelines for treating the health condition; and
  (d) determining a plurality of treatment plans by using the physician-validated context library to (1) iteratively process a second set of prompts using the context match and the physician-validated schemas and clinical guidelines and (2) determine, by a second LLM using the second set of prompts, at least one treatment plan of the plurality of treatment plans, wherein the second LLM is trained using the physician-validated context library,
  wherein the at least one treatment plan is used to treat the patient having or suspected of having the health condition based at least on a confidence level of the clinical diagnosis.

21. A computer-implemented method of providing artificial intelligence (AI)-based clinical decision support for treating a patient with a health condition, the method comprising:
  (a) receiving a clinical problem representation (CPR) based at least in part on an input provided by a healthcare provider (HCP) or a patient, wherein the CPR comprises a list of one or more symptoms presented or determined in real time during a patient encounter;
  (b) determining a clinical diagnosis by using the input to (1) iteratively process a first set of prompts using a plurality of healthcare context topics generated from a physician-validated context library and (2) determine, by a first large language model (LLM) using the first set of prompts, a context match from the plurality of healthcare context topics, wherein the context match associates the health condition with at least one of the plurality of healthcare context topics with a confidence level, and wherein the first LLM is generally trained using general or historical data;
  (c) using retrieval augmented generation (RAG) to (1) generate the plurality of healthcare context topics for use in determining the clinical diagnosis in (b) and (2) identify physician-validated schemas and clinical guidelines for treating the health condition; and
  (d) determining a plurality of treatment plans by using the physician-validated context library to (1) iteratively process a second set of prompts using the context match and the physician-validated schemas and clinical guidelines and (2) determine, by a second LLM using the second set of prompts, at least one treatment plan of the plurality of treatment plans, wherein the second LLM is trained using the physician-validated context library,
  wherein the at least one treatment plan is used to treat the patient having or suspected of having the health condition based at least on a confidence level of the clinical diagnosis.

* * * * *